(12) United States Patent
Yamasaki et al.

(10) Patent No.: US 11,254,783 B2
(45) Date of Patent: *Feb. 22, 2022

(54) XYLYLENEDIISOCYANATE COMPOSITION, XYLYLENEDIISOCYANATE-MODIFIED COMPOSITION, TWO-COMPONENT RESIN MATERIAL, AND RESIN

(71) Applicant: MITSUI CHEMICALS, INC., Tokyo (JP)

(72) Inventors: Satoshi Yamasaki, Chiba (JP); Daisuke Hasegawa, Yokohama (JP); Hirokazu Morita, Chiba (JP); Hideaki Otsuka, Chiba (JP); Tatsuya Nakashima, Shizuoka (JP); Chitoshi Shimakawa, Arao (JP); Shigetoshi Kuma, Kurume (JP); Masaaki Sasaki, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 86 days.

This patent is subject to a terminal disclaimer.

(21) Appl. No.: 16/800,676

(22) Filed: Feb. 25, 2020

(65) Prior Publication Data
US 2020/0190249 A1 Jun. 18, 2020

Related U.S. Application Data

(63) Continuation of application No. 16/301,257, filed as application No. PCT/JP2018/014896 on Apr. 9, 2018, now Pat. No. 10,640,605.

(30) Foreign Application Priority Data

Apr. 10, 2017 (JP) .............................. JP2017-077618

(51) Int. Cl.
*G02B 1/04* (2006.01)
*C08G 18/76* (2006.01)
(Continued)

(52) U.S. Cl.
CPC ........ *C08G 18/7642* (2013.01); *C07C 265/14* (2013.01); *C08G 18/3203* (2013.01);
(Continued)

(58) Field of Classification Search
CPC ........................... C08G 18/7642; G02B 1/041
See application file for complete search history.

(56) References Cited

U.S. PATENT DOCUMENTS 3,549,504 A   12/1970 Adica
3,658,656 A   4/1972 Adica
(Continued)

FOREIGN PATENT DOCUMENTS

CN   101072805 A   11/2007
CN   102070491 A   5/2011
(Continued)

OTHER PUBLICATIONS

International Search Report dated May 22, 2018 filed in PCT/JP2018/014896.
(Continued)

*Primary Examiner* — Michael L Leonard
(74) *Attorney, Agent, or Firm* — Rankin, Hill & Clark LLP

(57) ABSTRACT

A xylylenediisocyanate composition including xylylenediisocyanate and a compound represented by Chemical Formula (1) below, wherein 0.6 ppm or more and 60 ppm or less
(Continued)

of the compound represented by Chemical Formula (1) below is contained:

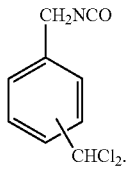

Chemical Formula (1)

3 Claims, 6 Drawing Sheets

(51) Int. Cl.
    *C08G 18/32*     (2006.01)
    *C08G 18/38*     (2006.01)
    *C08G 18/71*     (2006.01)
    *C07C 265/14*     (2006.01)

(52) U.S. Cl.
    CPC ..... *C08G 18/3225* (2013.01); *C08G 18/3876* (2013.01); *C08G 18/712* (2013.01); *C08G 18/714* (2013.01); *C08G 18/76* (2013.01); *G02B 1/041* (2013.01)

(56) References Cited

U.S. PATENT DOCUMENTS

| | | | |
|---|---|---|---|
| 3,829,460 A * | 8/1974 | Buttner et al. | C07C 265/12 560/349 |
| 4,419,295 A | 12/1983 | Hennig et al. | |
| 4,422,976 A | 12/1983 | Yamamoto et al. | |
| 5,302,749 A | 4/1994 | Nagata | |
| 5,576,412 A | 11/1996 | Hirata | |
| 2009/0124785 A1 | 5/2009 | Shimakawa | |
| 2009/0292098 A1 | 11/2009 | Wagner | |
| 2011/0275854 A1 | 11/2011 | Daussin et al. | |
| 2017/0029552 A1 | 2/2017 | Maleika | |
| 2017/0121449 A1 | 5/2017 | Maleika | |
| 2017/0210702 A1 | 7/2017 | Halpaap | |
| 2018/0171065 A1 | 6/2018 | Nakagawa | |

FOREIGN PATENT DOCUMENTS

| | | |
|---|---|---|
| CN | 104945283 A | 9/2015 |
| CN | 106496073 A | 3/2017 |
| EP | 0384463 A1 | 8/1990 |
| GB | 1086782 A | 10/1967 |
| JP | S44002984 B | 2/1969 |
| JP | S45017434 B | 6/1970 |
| JP | S45022735 B | 7/1970 |
| JP | H03007253 A | 1/1991 |
| JP | H07033851 A | 2/1995 |
| JP | H07233137 | 9/1995 |
| JP | 2006273717 A | 10/2006 |
| JP | 2014-234429 A | 12/2014 |
| JP | 2014-234430 A | 12/2014 |
| JP | 2017517487 A | 6/2017 |
| WO | 2007010996 A1 | 1/2007 |
| WO | 2015155366 A1 | 10/2015 |
| WO | 2016199795 A1 | 12/2016 |
| WO | 2017179575 A1 | 10/2017 |

OTHER PUBLICATIONS

PCT First Notice Informing the Applicant of the Communication of the International Application (to Designated Offices Which do not Apply the 30 Month Time Limit Under Article 22(1) (Form PCT/IB/308) filed in PCT/JP2018/014896 dated Nov. 15, 2018.

PCT Second and Supplementary Notice Informing the Applicant of the Communication of the International Application (to Designated Offices Which Apply the 30 Month Time Limit Under Article 22(1) (Form PCT/IB/308) filed in PCT/JP2018/014896 dated Aug. 15, 2019.

PCT International Preliminary Reporton Patentability (Form PCT/IB/373) filed in PCT/JP2018/014896, with PCT Notification Concerning Transmittal of International Preliminary Report on Patentability (Form PCT/IB/326) dated Oct. 24, 2019.

PCT International Preliminary Reporton Patentability (Form PCT/IB/373) filed in PCT/JP2018/014896, with PCT Notification of Transmittal of Translation of the International Preliminary Report on Patentability (Form PCT/B/338) dated Oct. 24, 2019.

* cited by examiner

XYLYLENEDIISOCYANATE COMPOSITION, XYLYLENEDIISOCYANATE-MODIFIED COMPOSITION, TWO-COMPONENT RESIN MATERIAL, AND RESIN

TECHNICAL FIELD

The present invention relates to a xylylenediisocyanate composition, a xylylenediisocyanate-modified composition, a two-component resin material, and resin.

BACKGROUND ART

Conventionally, xylylenediisocyanate has been known as an ingredient of polyurethane resin used for various industrial products.

Such xylylenediisocyanate is produced by allowing xylylenediamine to react with carbonyl chloride, and it has been known that chlorinated product is by-produced at the time of reaction (for example, see Patent Document 1).

Patent Document 1 discloses xylylenediisocyanate containing 0.1 wt % of chloromethyl benzyl isocyanate as the by-produced chlorinated product.

CITATION LIST

Patent Document

Patent Document 1 WO2007/010996A1

SUMMARY OF THE INVENTION

Problem to be Solved by the Invention

Excellent resistance to discoloration is required for polyurethane resin depending on its purpose and use. However, the polyurethane resin produced from the xylylenediisocyanate described in Patent Document 1 may not secure sufficient resistance to discoloration.

The present invention provides a xylylenediisocyanate composition that is capable of stably producing resin with excellent resistance to discoloration, a xylylenediisocyanate-modified composition, and a two-component resin material.

Means for Solving the Problem

The present invention [1] includes a xylylenediisocyanate composition including xylylenediisocyanate and a compound represented by Chemical Formula (1) below, wherein 0.6 ppm or more and 60 ppm or less of the compound represented by formula (1) below is contained.

[Chemical Formula 1]

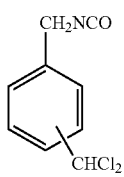

Chemical Formula (1)

The present invention [2] includes the xylylenediisocyanate composition described in [1] above, further including chloromethyl benzyl isocyanate, wherein the chloromethyl benzyl isocyanate content is 0.2 ppm or more and 3000 ppm or less.

The present invention [3] includes the xylylenediisocyanate composition described in [2] above, wherein the chloromethyl benzyl isocyanate content is 0.2 ppm or more and 1600 ppm or less.

The present invention [4] includes a xylylenediisocyanate-modified composition, in which the xylylenediisocyanate composition described in any one of the above-described [1] to [3] is modified, wherein the xylylenediisocyanate-modified composition contains at least one of the functional group of (a) to (i) below:
(a) isocyanurate group,
(b) allophanate group,
(c) biuret group,
(d) urethane group,
(e) urea group,
(f) iminooxadiazinedione group,
(g) uretdione group,
(h) uretonimine group, and
(i) carbodiimide group.

The present invention [5] includes resin, wherein the resin is a reaction product of an isocyanate component containing the xylylenediisocyanate composition described in any one of the above-described [1] to [3] and/or the xylylenediisocyanate-modified composition described in [4] above, and an active hydrogen group-containing component.

The present invention [6] includes the resin described in [5] above, wherein the resin is an optical material.

The present invention [7] includes the resin described in [6] above, wherein the resin is an optical lens.

The present invention [8] includes a two-component resin material, including the xylylenediisocyanate composition described in any one of the above-described [1] to [3] and/or the isocyanate component containing the xylylenediisocyanate-modified composition described in [4] above, and an active hydrogen group-containing component.

The present invention [9] includes the two-component resin material described in [8] above, which is a coating material.

The present invention [10] includes a method for producing a xylylenediisocyanate composition, the method including: a hydrochloride-producing step of mixing xylylenediamine with hydrogen chloride to produce xylylenediamine hydrochloride; an isocyanate-formation step, in which xylylenediamine hydrochloride and carbonyl chloride are subjected to isocyanate-formation reaction to produce xylylenediisocyanate, and to produce a compound represented by Chemical Formula (1) below to prepare a reaction mass containing xylylenediisocyanate and the compound represented by Chemical Formula (1) below; and a purification step, in which the reaction mass is purified to prepare a xylylenediisocyanate composition; wherein the xylylenediisocyanate composition contains 0.6 ppm or more and 60 ppm or less of the compound represented by Chemical Formula (1) below.

[Chemical Formula 1]

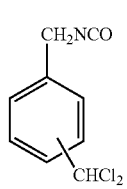

Chemical Formula (1)

The present invention [11] includes the method for producing a xylylenediisocyanate composition described in [10] above, wherein in the step of preparing the reaction mass, the reaction pressure (gauge pressure) is more than atmospheric pressure.

The present invention [12] includes the method for producing a xylylenediisocyanate composition described in [10] or [11] above, wherein the hydrochloride-producing step and the isocyanate-formation step are continuously carried out.

Effects of the Invention

The xylylenediisocyanate composition of the present invention includes xylylenediisocyanate and the compound represented by the above-described Chemical Formula (1), wherein 0.6 ppm or more and 60 ppm or less of the compound represented by the above-described Chemical Formula (1) is contained.

Therefore, the xylylenediisocyanate composition of the present invention, and the resin produced from the resin material containing the xylylenediisocyanate composition of the present invention have excellent resistance to discoloration.

DESCRIPTION OF THE EMBODIMENTS

1. Xylylenediisocyanate Composition

Figure 1:
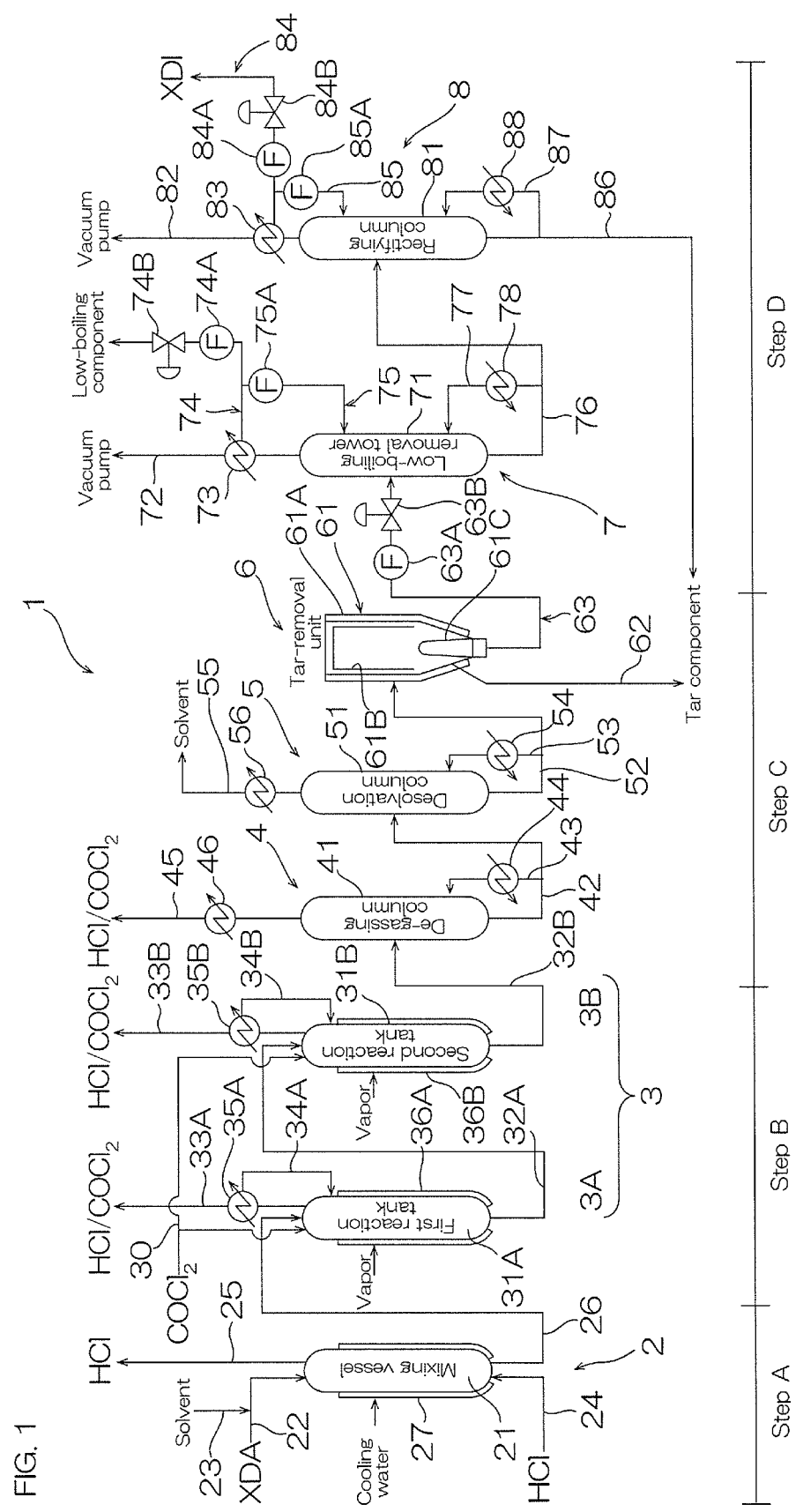
FIG. 1 is a schematic diagram illustrating the configuration of an embodiment of the plant in which the xylylenediisocyanate composition of the present invention is produced.

The xylylenediisocyanate composition of the present invention is a substantially single compound (that is, xylylenediisocyanate) mainly composed of, i.e., 99 mass % or more, xylylenediisocyanate. However, the xylylenediisocyanate composition of the present invention contains the compound represented by Chemical Formula (1) below as a sub component, and therefore defined as the "xylylenediisocyanate composition".

That is, the xylylenediisocyanate composition of the present invention contains xylylenediisocyanate and the compound represented by Chemical Formula (1) below as essential components. In the following, the xylylenediisocyanate composition is referred to as "XDI composition", xylylenediisocyanate is referred to as "XDI", and the compound represented by Chemical Formula (1) below (dichloromethyl benzyl isocyanate) is referred to as "DCI".

[Chemical Formula 1]

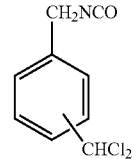

Chemical Formula (1)

XDI include structural isomers of 1,2-XDI (o-XDI), 1,3-XDI (m-XDI), and 1,4-XDI (p-XDI). These structural isomers of XDI can be used singly, or can be used in combination of two or more.

For the XDI, preferably, 1,3-XDI and 1,4-XDI are used, more preferably 1,3-XDI is used.

The XDI content (purity) relative to a total mass of the XDI composition is, for example, 99.50 mass % or more, preferably 99.70 mass % or more, more preferably 99.90 mass % or more, and for example, 99.999 mass % or less, preferably 99.990 mass % or less. The XDI content can be measured in accordance with the method described in Examples described later.

DCI is a chlorine compound by-produced in production of XDI described later. DCI includes structural isomers of o-DCI, m-DCI, and p-DCI. One of these structural isomers of DCI, or two or more of these structural isomers of DCI can be contained in the XDI composition.

The structural isomers of DCI by-produced in production of XDI are in correspondence with the structural isomers of the produced XDI. Therefore, the XDI composition contains DCI in correspondence with the structural isomers of the above-described XDI. That is, in the XDI composition, when o-XDI is contained, o-DCI is contained; when m-XDI is contained, m-DCI is contained; and when p-XDI is contained, p-DCI is contained.

For the DCI, preferably, m-DCI and p-DCI are contained, more preferably, m-DCI is contained.

The DCI content relative to a total mass of the XDI composition is 0.6 ppm or more and 60 ppm or less. The DCI content can be measured by gas chromatograph analysis in accordance with the method described in Examples described later. The suitable range of the DCI content in accordance with the use of the XDI composition is described in detail later.

When the DCI content is within the above-described range, yellowing and/or cloudiness of the resin produced from the XDI composition can be suppressed.

The XDI composition may further contain chloromethyl benzyl isocyanate (monochloromethyl benzyl isocyanate) represented by Chemical Formula (2) below. In the following, chloromethyl benzyl isocyanate is referred to as CBI.

[Chemical Formula 2]

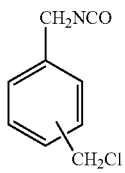

Chemical Formula (2)

CBI is a chlorine compound by-produced in production of XDI described later. That is, in the production of XDI, DCI and CBI may be by-produced. CBI includes structural isomers of o-CBI, m-CBI, and p-CBI. One of these structural isomers of CBI, or two or more of these structural isomers of CBI may be included in the XDI composition. The structural isomers of CBI by-produced in production of XDI are in correspondence with the structural isomers of the produced XDI, as in the case of DCI.

The CBI content relative to a total mass of the XDI composition is, for example, 0.2 ppm or more, preferably 6 ppm or more, more preferably 100 ppm or more, and for example, 5000 ppm or less, preferably 4000 ppm or less, more preferably 3000 ppm or less, particularly preferably 1600 ppm or less, especially preferably 1000 ppm or less. The CBI content can be measured in accordance with the method described in Examples described later.

The CBI content is, for example, 2 or more times, preferably 10 or more times, more preferably 20 or more times the DCI content, and for example, 800 or less times, preferably 300 or less times, more preferably 50 or less times the DCI content.

When the CBI content is within the above-described range, yellowing of the resin produced from the XDI composition can be reliably suppressed. Particularly, when the CBI content is the above-described upper limit or less, yellowing of the resin produced from the XDI composition can be reliably suppressed, and urethane-forming reaction at the time of resin production can be smoothly progressed, which reliably allows for improvement in mechanical properties of resin.

The XDI composition may further contain other by-products such as dichloromethaneimino-methylbenzylisocyanate, xylylenedichloride (XDC), and cyanobenzylisocyanate (MCN) represented by Chemical Formula (3) below.

[Chemical Formula 3]

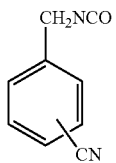

Chemical Formula (3)

Meanwhile, when the XDI composition is produced by the method for producing XDI composition described later (that is, liquid phase method), the XDI composition does not substantially contain cyanobenzylisocyanate (MCN) represented by the above-described Chemical Formula (3).

To be specific, the cyanobenzylisocyanate (MCN) represented by the above-described Chemical Formula (3) is contained in an amount of, relative to a total mass of the XDI composition, for example, 500 ppm or less, preferably less than 300 ppm, more preferably less than 100 ppm, and for example, 0 ppm or more. The MCN content can be measured in accordance with the method described in Examples described later.

When the MCN content is the above-described upper limit or less, the resin produced from the XDI composition can be more reliably prevented from coloring (yellowing).

The XDI composition has a hydrolysable chlorine concentration (HC) of, for example, 10 ppm or more, preferably 20 ppm or more, and for example, 1500 ppm or less, preferably 1000 ppm or less. The hydrolysable chlorine concentration (HC concentration) is measured in accordance with hydrolysable chlorine determination described in JIS K-1603-3 (2007).

The hydrolysable chlorine concentration includes the above-described DCI, CBI, and other by-products. Therefore, the hydrolysable chlorine concentration of the XDI composition does not correlate with the DCI content in the XDI composition, as is clear from Examples described later. Thus, the DCI content in the XDI composition cannot be calculated from the hydrolysable chlorine concentration in the XDI composition.

2. Method for Producing XDI Composition

Next, description is given below of a method for producing a XDI composition.

To produce the XDI composition, for example, xylylenediamine, i.e., material, is subjected to isocyanate-formation to produce a reaction mass containing XDI and DCI (composition before purification), and then thereafter the reaction mass is purified.

In the following, xylylenediamine is referred to as XDA. XDA includes structural isomers of 1,2-XDA (o-XDA), 1,3-XDA (m-XDA), and 1,4-XDA (p-XDA).

(2-1) Production Step of Reaction Mass (Steps A to C)

To produce the reaction mass, for example, XDA is mixed with hydrogen chloride to form XDA hydrochloride, and then hydrochloride is allowed to react with carbonyl chloride (phosgene) (amine hydrochloride phosgenation method). That is, the reaction mass production step includes a hydrochloride-producing step (step A), in which XDA is mixed with hydrogen chloride to form XDA hydrochloride, and an isocyanate-formation step (step B), in which XDA hydrochloride is allowed to react with carbonyl chloride to subject XDA hydrochloride to isocyanate-formation (phosgenation). The hydrochloride-producing step (step A) and the isocyanate-formation step (step B) are the liquid phase method.

In the hydrochloride-producing step (step A), for example, XDA is mixed with hydrogen chloride in the presence of an inert solvent to produce XDA hydrochloride (salt-forming).

Examples of the inert solvent include aromatic hydrocarbons such as benzene, toluene, and xylene; aliphatic hydrocarbons such as octane and decane; alicyclic hydrocarbons such as cyclohexane, methylcyclohexane, and ethylcyclohexane; halogenated aromatic hydrocarbons such as chlorotoluene, chlorobenzene, dichlorobenzene, dibromobenzene, and trichlorobenzene; nitrogen-containing compounds such as nitrobenzene, N,N-dimethylformamide, N,N-dimethylacetamide, and N,N'-dimethylimidazolidinone; ethers such as dibutylether, ethylene glycoldimethylether, and ethyleneglycoldiethylether; ketones such as heptanone, diisobutylketone, methylisobutylketone, and methylethylketone; fatty acid esters such as ethyl acetate, butyl acetate, amyl acetate, and ethoxyethyl acetate; and aromatic carboxylic acid esters such as salicylic acidmethyl, phthalic aciddimethyl, phthalic aciddibutyl, and benzoic acidmethyl. The inert solvent can be used singly, or can be used in combination of two or more.

Of these inert solvents, preferably, halogenated aromatic hydrocarbons are used, more preferably, chlorobenzene and dichlorobenzene are used.

Then, hydrogen chloride gas is fed to the inert solvent, and an amine solution in which XDA is dissolved in the inert solvent is fed. Thereafter, hydrogen chloride gas and amine solution are stirred and mixed.

The XDA content in the amine solution is not particularly limited, and for example, 3.0 mass % or more, preferably 5.0 mass % or more, and for example, 30 mass % or less, preferably 20 mass % or less.

Relative to a total mass of XDA and the inert solvent, the mass of XDA fed (total amine concentration) is, for example, 3 mass % or more, preferably 5 mass % or more, and for example, 30 mass % or less, preferably 20 mass % or less, more preferably 15 mass % or less.

Hydrogen chloride is fed in an amount of (in mol), relative to 1 mol of XDA, for example, 2 or more times, and for example, 10 or less times, preferably 6 or less times, more preferably 4 or less times.

The salt-forming temperature in the hydrochloride-producing step is, for example, 30° C. or more, preferably 50° C. or more, more preferably 60° C. or more, and for example, 160° C. or less, preferably 150° C. or less, more preferably 140° C. or less.

The salt-forming pressure (gauge pressure) in the hydrochloride-producing step is, for example, atmospheric pressure (0 MPaG) or more, preferably 0.01 MPaG or more, more preferably 0.02 MPaG or more, and for example, 1.0 MPaG or less, preferably 0.5 MPaG or less, more preferably 0.4 MPaG or less.

In this manner, XDA hydrochloride is produced from XDA and hydrogen chloride (hydrochloride-formation reaction), and a slurry containing XDA hydrochloride is produced.

Then, in the isocyanate-formation step (step B), the slurry containing XDA hydrochloride is fed with carbonyl chloride, to allow XDA hydrochloride to react with carbonyl chloride (isocyanate-formation reaction, phosgenation).

Carbonyl chloride is fed in an amount of (in mol), relative to 1 mol of XDA hydrochloride, for example, 4 or more times, preferably 5 or more times, more preferably 6 or more times, and for example, 50 or less times, preferably 40 or less times, more preferably 30 or less times.

The amount of carbonyl chloride fed affects reaction velocity/rate of the isocyanate-formation reaction and production of by-produced DCI. By adjusting the amount of carbonyl chloride fed within the above-described range, the amount of DCI produced can be adjusted. To be specific, when the amount of carbonyl chloride fed is increased, the amount of DCI produced can be increased, and when the amount of carbonyl chloride fed is decreased, production amount of DCI can be decreased.

The reaction time in the isocyanate-formation step is, for example, 4 hr or more, preferably 6 hr or more, and for example, 25 hr or less, preferably 20 hr or less, more preferably 15 hr or less.

By adjusting the reaction time of the isocyanate-formation step within the above-described range, production amounts of CBI and DCI can be adjusted. To be specific, by increasing the reaction time in the isocyanate-formation step, XDA hydrochloride can be allowed to react with carbonyl chloride reliably, and the production amounts of CBI and DCI can be increased, and by decreasing the reaction time in the isocyanate-formation step, the amount of the by-produced tar component can be decreased, and the amounts of CBI and DCI produced can be decreased.

The reaction temperature in the isocyanate-formation step is, for example, 90° C. or more, preferably 100° C. or more, more preferably 110° C. or more, and for example, 190° C. or less, preferably 180° C. or less, more preferably 160° C. or less.

When the temperature in the isocyanate-formation step is the above-described lower limit or more, the reaction velocity/rate can be improved, and can be carried out industrially suitably. When the temperature in the isocyanate-formation step is the above-described upper limit or less, excessive production of by-products (CBI and DCI, etc.) can be suppressed, and the XDI composition can be produced by simple purification.

Examples of the reaction pressure in the isocyanate-formation step (gauge pressure) include more than atmospheric pressure (0 MPaG), preferably 0.0005 MPaG or more, more preferably 0.001 MPaG or more, even more preferably 0.003 MPaG or more, particularly preferably 0.01 MPaG (10 kPaG) or more, especially preferably 0.02 MPaG (20 kPaG) or more, most preferably 0.03 MPaG (30 kPaG) or more, and for example, 0.6 MPaG or less, preferably 0.4 MPaG or less, more preferably 0.2 MPaG or less.

However, when the reaction pressure in the isocyanate-formation step is atmospheric pressure or less (that is, under reduced pressure or atmospheric pressure), DCI cannot be produced sufficiently in the isocyanate-formation step.

Meanwhile, when the reaction pressure in the isocyanate-formation step is the above-described lower limit or more, in the isocyanate-formation step, DCI can be reliably produced.

By adjusting the reaction pressure in the isocyanate-formation step within the above-described range, production amounts of CBI and DCI can be adjusted. To be specific, by increasing the reaction pressure in the isocyanate-formation step, excessive carbonyl chloride can be collected by a condenser, compared with the case where a refrigerator is necessary for collection of carbonyl chloride, energy efficiency can be improved, and the amount of CBI and DCI produced can be increased.

By decreasing the reaction pressure in the isocyanate-formation step, decomposition reaction from intermediate carbamoylchloride to isocyanate can be efficiently progressed, and reaction time can be decreased, and the production amounts of CBI and DCI can be decreased.

The isocyanate-formation step can be performed by any of batch method and continuous method, but preferably it is performed continuously. That is, preferably, a slurry (XDA hydrochloride) produced in a mixing vessel is continuously fed from the mixing vessel to a reaction tank that is different from the mixing vessel, and continuously taking the reaction solution (reaction mass) from the reaction tank while allowing XDA hydrochloride to react with carbonyl chloride in the reaction tank.

By performing the isocyanate-formation step by batch, XDA hydrochloride may not react with high temperature and excessive carbonyl chloride for a long period of time, and DCI may not be produced. In the isocyanate-formation step by batch, in the initial period of reaction in which the XDA hydrochloride concentration is high, homogeneous mixing may be difficult, which necessitates a high output mixer, and the size of the reaction tank may be increased. Furthermore, in the isocyanate-formation step by batch, a large amount of carbonyl chloride is necessary because in the initial reaction period, a slurry with a relatively high XDA hydrochloride concentration is reacted with carbonyl chloride, and a large size carbonyl chloride collection device and a large size by-produced hydrogen chloride gas treatment device are necessary.

Meanwhile, when the isocyanate-formation step is performed continuously, the residence time in the reaction tank is average value, and a portion of the reaction solution stays in the reaction tank for a long time, and as a result, XDA hydrochloride is allowed to react with carbonyl chloride for a long time, and therefore DCI is produced. Furthermore, in the continuous isocyanate-formation step, along with progress of the isocyanate-formation reaction, liquid XDI is produced, and the XDA hydrochloride concentration in the slurry decreases, which allows for smooth stirring with a simple stirring device. Furthermore, in the continuous isocyanate-formation step, the amount of carbonyl chloride fed and the amount of the by-produced hydrogen chloride gas can be made constant, and the carbonyl chloride collection device and the hydrogen chloride gas treatment device can be made smaller, and also stable operation can be achieved. Thus, the continuous isocyanate-formation step is suitable compared with the batch isocyanate-formation step, in view of auto operation for mass production of XDI.

That is, in mass production scale, preferably, the isocyanate-formation step is continuous reaction.

The isocyanate-formation step is preferably performed in multiple stages in view of volumetric efficiency of the reaction tank. The stages in the isocyanate-formation step are, for example, 2 or more stages and 5 or less stages.

For example, when the isocyanate-formation step is performed in 2 stages, the range in the residence time in total in the 2-stage isocyanate-formation step is the same as the range in the above-described reaction time, and the range of the amount of the carbonyl chloride fed in the 2-stage isocyanate-formation step is the same as the range of the above-described amount of the carbonyl chloride fed.

XDA hydrochloride is allowed to react with carbonyl chloride to produce a main component, XDI, in the above-described manner. Also, DCI is produced as a by-product, and furthermore, CBI may also be produced as a by-product.

Then, as necessary, the reaction solution (reaction mixture) is subjected to de-gassing, desolvation, and a tar-removal step (step C). In the de-gassing, gas such as excessive carbonyl chloride and by-produced hydrogen chloride is removed from the reaction solution (reaction mixture) with a known de-gassing column. In the desolvation, the inert solvent is distilled off from the reaction solution with a known distillation column. In the tar-removal step, the tar component is removed from the reaction solution with a known tar-remover. The reaction mass from which the tar component is removed by the tar-removal step is referred to as a tar-removed mass.

In the above-described manner, the reaction mass containing XDI and DCI (preferably, tar-removed mass) is produced.

The reaction mass has a XDI content of, for example, 80.0 mass % or more, preferably 90.0 mass % or more, more preferably 95.0 mass % or more, and for example, 99.0 mass % or less, preferably 98.5 mass % or less, more preferably 98.0 mass % or less.

The reaction mass has a DCI content of, for example, 1 ppm or more, preferably 2 ppm or more, more preferably 5 ppm or more, and for example, 80 ppm or less, preferably 70 ppm or less, more preferably 50 ppm or less.

When the reaction mass contains CBI, the reaction mass has a CBI content of, for example, 0.1 mass % or more, preferably 0.3 mass % or more, more preferably 0.5 mass % or more, and for example, 3.0 mass % or less, preferably 1.5 mass % or less, more preferably 1.0 mass % or less.

When the reaction mass contains the inert solvent, the reaction mass has an inert solvent content of, for example, 0.1 mass % or more, preferably 0.3 mass % or more, more preferably 0.5 mass % or more, even more preferably 1.0 mass % or more, and for example, 5.0 mass % or less, preferably 3.0 mass % or less.

(2-2) Reaction Mass Purification Step (Step D)

Then, the reaction mass (composition before purification) is purified to adjust the DCI content to the above-described range.

The reaction mass can be purified by an industrial separation method such as crystallization and distillation, and preferably, distillation is used. To purify the reaction mass by distillation, for example, a low-boiling component is distilled off by distillation from the reaction mass, and then a low-boiling removed mass, i.e., reaction mass after low-boiling removal, is rectified. That is, the reaction mass purification step includes a low-boiling removal step, in which the low-boiling component is distilled off from the reaction mass, and a rectification step, in which the low-boiling removed mass is rectified.

In the low-boiling removal step, for example, the reaction mass (preferably, tar-removed mass) is distilled with a low-boiling removal tower to distill off the low-boiling component.

Examples of the low-boiling removal tower include a plate column and a packed column, and preferably, a packed column is used. The low-boiling removal tower has theoretical plate number of, for example, 3 or more, preferably 5 or more, more preferably 7 or more, and for example, 40 or less, preferably 20 or less, more preferably 15 or less.

The low-boiling removal tower has a column-bottom temperature of, for example, 130° C. or more, preferably 140° C. or more, more preferably 150° C. or more, and for example, 200° C. or less, preferably 190° C. or less, more preferably 180° C. or less.

The low-boiling removal tower has a column-top temperature of, for example, 90° C. or more, preferably 100° C. or more, more preferably 110° C. or more, and for example, 160° C. or less, preferably 150° C. or less, more preferably 140° C. or less.

The low-boiling removal tower has a column-top pressure of, for example, 0.05 kPa or more, preferably 0.1 kPa or more, more preferably 0.2 kPa or more, and for example, 3.0 kPa or less, preferably 2.0 kPa or less, more preferably 1.0 kPa or less.

The low-boiling removal tower has a column-top reflux ratio of, for example, 1 or more, preferably 5 or more, more preferably 10 or more, and for example, 80 or less, preferably 60 or less, more preferably 50 or less.

The low-boiling removal tower has a residence time of, for example, 0.1 hours or more, preferably 0.2 hours or more, more preferably 0.3 hours or more, and for example, 10 hours or less, preferably 5 hours or less, more preferably 3 hours or less.

In this manner, the low-boiling component is distilled off, and the low-boiling removed mass is obtained as bottoms, which is a tar-removed mass after low-boiling removal.

Then, in the rectification step, for example, the low-boiling removed mass is distilled with a rectifying column, and the XDI composition is taken out as a fraction.

Examples of the rectifying column include a plate column and a packed column, and preferably, the packed column is used. The rectifying column has a theoretical plate number of, for example, 1 or more, and for example, 20 or less, preferably 10 or less, more preferably 5 or less.

The rectifying column has a column-bottom temperature of, for example, 120° C. or more, preferably 130° C. or more, more preferably 140° C. or more, and for example, 190° C. or less, preferably 180° C. or less, more preferably 170° C. or less.

The rectifying column has a column-top temperature of, for example, 90° C. or more, preferably 110° C. or more, more preferably 130° C. or more, and for example, 180° C. or less, preferably 170° C. or less, more preferably 160° C. or less.

The rectifying column has a column-top pressure of, for example, 0.05 kPa or more, preferably 0.1 kPa or more, more preferably 0.2 kPa or more, and for example, 3.0 kPa or less, preferably 2.0 kPa or less, more preferably 1.0 kPa or less.

The rectifying column has a column-top reflux ratio of, for example, 0.1 or more, preferably 0.2 or more, more preferably 0.3 or more, and for example, 50 or less, preferably 20 or less, more preferably 10 or less.

The rectifying column has a residence time of, for example, 0.2 hours or more, preferably 0.5 hours or more, more preferably 1.0 hour or more, and for example, 20 hours or less, preferably 10 hours or less.

In the above-described manner, the DCI content in the XDI composition can be adjusted, and the XDI composition is taken out as a fraction. By adding DCI to the XDI composition, the DCI content in the XDI composition can also be adjusted.

3. Plant (3-1) Plant Configuration

The above-described method for producing a XDI composition is performed in, for example, a plant 1 shown in FIG. 1. As shown in FIG. 1, in the plant 1, the 2-stage continuous isocyanate-formation step is performed in an isocyanate-formation unit 3 described later, and by adjusting the above-described amount of carbonyl chloride fed, reaction temperature, reaction pressure, and average residence time suitably, the amounts of XDI and DCI produced are adjusted. Then, in a low-boiling removal unit 7 described later, the low-boiling removal step is performed, and by adjusting the above-described column-top reflux ratio suitably, the DCI content in the XDI composition is adjusted.

As shown in FIG. 1, the plant 1 is a system for producing a XDI composition. The plant 1 includes a salt-forming unit 2, an isocyanate-formation unit 3, a de-gassing unit 4, a desolvation unit 5, a tar-removal unit 6, a low-boiling removal unit 7, and a rectification unit 8.

The salt-forming unit 2 is a XDA hydrochloride production system, which is capable of performing the above-described hydrochloride-producing step (step A), and produces XDA hydrochloride from XDA and hydrogen chloride. The salt-forming unit 2 includes a mixing vessel 21, a hydrogen chloride feed line 24, an amine feed line 22, a solvent feed line 23, a purge line 25, and a hydrochloride feed line 26.

The mixing vessel 21 is composed of, for example, a heat-resistant and pressure-resistant vessel capable of controlling temperature and pressure.

Inside the mixing vessel 21, an impeller (not shown) for stirring and mixing XDA and hydrogen chloride is provided. Examples of the impeller include, in view of efficiently dispersing hydrogen chloride gas and XDA hydrochloride, for example, puddle blade, pitched paddle blade, turbine blade, three-blade retreat impeller, TWINSTIR blade, FULLZONE blade, MAXBLEND blade, and multiple-stage impeller in which these blades are combined is used.

The mixing vessel 21 is also provided with a cooler 27, which is capable of cooling inside the mixing vessel 21. For the cooler 27, for example, a jacket capable of feeding a refrigerant, cooling coil, or external circulating condenser are used. In FIG. 1, an example is shown where the cooler 27 is a jacket capable of feeding cooling water (refrigerant).

The hydrogen chloride feed line 24 feeds hydrogen chloride (HCl) gas to the mixing vessel 21. The downstream-end portion of the hydrogen chloride feed line 24 is connected to a bottom portion of the mixing vessel 21. The upstream-end portion of the hydrogen chloride feed line 24 is connected to a tank, which is not shown, in which hydrogen chloride is stored.

The amine feed line 22 feeds XDA to the mixing vessel 21. The downstream-end portion of the amine feed line 22 is connected to a top portion of the mixing vessel 21. The upstream-end portion of the amine feed line 22 is connected to a tank, which is not shown, in which XDA is stored.

The solvent feed line 23 feeds the above-described inert solvent to the amine feed line 22. The downstream-end portion of the solvent feed line 23 is connected along the amine feed line 22. The upstream-end portion of the solvent feed line 23 is connected to a tank, which is not shown, in which the inert solvent is stored.

The purge line 25 discharges hydrogen chloride gas that is excessive in the hydrochloride-producing step from the mixing vessel 21. The upstream-end portion of the purge line 25 is connected to the top portion of the mixing vessel 21. The downstream-end portion of the purge line 25 is connected to a hydrogen chloride gas collection device, which is not shown.

The hydrochloride feed line 26 feeds the slurry containing XDA hydrochloride from the mixing vessel 21 to the isocyanate-formation unit 3. The upstream-end portion of the hydrochloride feed line 26 is connected to the mixing vessel 21. In FIG. 1, the upstream-end portion of the hydrochloride feed line 26 is connected to the bottom portion of the mixing vessel 21, but depending on restrictions such as layout, it can be connected to the top portion or side portion of the mixing vessel 21 suitably. The downstream-end portion of the hydrochloride feed line 26 is connected to the reaction tank 31A described later. In FIG. 1, the downstream-end portion of the hydrochloride feed line 26 is connected to the top portion of the reaction tank 31A, but it can be connected to the side portion or bottom portion of the reaction tank 31A to allow feeding in the liquid. Although not shown, a known slurry pump for feeding the slurry, for example, gear pump, non-seal pump, mechanical seal pump, and magnet pump is provided along the hydrochloride feed line 26. The slurry can be fed by the pressure difference between the mixing vessel 21 and the reaction tank 31A. Furthermore, the reaction tank 31A and the reaction tank 31B can also be provided with the above-described slurry pump for feeding the slurry, or the slurry can be fed by pressure difference between the reaction tank 31A and the reaction tank 31B.

The isocyanate-formation unit 3 is a XDI production system, which is capable of performing the above-described isocyanate-formation step (step B), and produces XDI by allowing XDA hydrochloride to react with carbonyl chloride. To be specific, the isocyanate-formation unit 3 is capable of performing the 2-stage continuous isocyanate-formation step, and includes the first isocyanate-formation unit 3A, second isocyanate-formation unit 3B, and carbonyl chloride feed line 30.

The first isocyanate-formation unit 3A and the second isocyanate-formation unit 3B have the same configuration except for the connection portion of the reaction mass feed line, described later. Therefore, the configuration of the first isocyanate-formation unit 3A is described in detail, and description of the second isocyanate-formation unit 3B is omitted.

The first isocyanate-formation unit 3A includes a reaction tank 31A, a purge line 33A, a condenser 35A, a reflux line 34A, and a reaction mass feed line 32A. The reaction tank, purge line, condenser, reflux line, and reaction mass feed line included in the second isocyanate-formation unit 3B is referred to as a reaction tank 31B, purge line 33B, condenser 35B, reflux line 34B, and reaction mass feed line 32B.

The reaction tank 31A is composed of, for example, a heat-resistant and pressure-resistant vessel capable of controlling temperature and pressure. To the reaction tank 31A, the downstream-end portion of the hydrochloride feed line 26 is connected. In FIG. 1, the downstream-end portion of the hydrochloride feed line 26 is connected to the top portion of the reaction tank 31A, but depending on restrictions such as layout, it can be suitably connected to the side portion or bottom portion of the reaction tank 31A.

An impeller (not shown) for stirring and mixing the slurry and carbonyl chloride is provided inside the reaction tank 31A. For the impeller, for example, the above-described impeller is used.

A heater 36A capable of heating inside the reaction tank 31A is provided in the reaction tank 31A. For the heater 36A, for example, a jacket capable of feeding a heating medium, a steam coil, and an external circulation heater are used. In FIG. 1, the case where the heater 36A is a jacket capable of feeding vapor (heating medium) is shown.

The purge line 33A discharges a gas component including the excessive carbonyl chloride, by-produced hydrogen chloride gas, and inert solvent from the reaction tank 31A. The upstream-end portion of the purge line 33A is connected to the top portion of the reaction tank 31A. The downstream-end portion of the purge line 33A, which is not shown, is connected to the carbonyl chloride collector.

The condenser 35A is provided along the purge line 33A. The condenser 35A cools the gas component that passes the purge line 33A to condense a portion of the inert solvent and carbonyl chloride in the gas component. In this manner, a purge gas containing carbonyl chloride gas and hydrogen chloride gas is separated from a reflux solution containing the inert solvent and liquefied carbonyl chloride. Although not shown, a known regulating valve for regulating the internal pressure of reaction tank 31A is provided at the downstream side of the condenser 35A in the purge line 33A.

The reflux line 34A returns the reflux solution separated in the condenser 35A to the reaction tank 31A. The upstream-end portion of the reflux line 34A is connected to the condenser 35A. The downstream-end portion of the reflux line 34A is connected to the top portion of the reaction tank 31A.

The reaction mass feed line 32A of the first isocyanate-formation unit 3A feeds the reaction mass (primary reaction mass) in the isocyanate-formation step of the 1 stages from the reaction tank 31A to the reaction tank 31B of the second isocyanate-formation unit 3B. The upstream-end portion of the reaction mass feed line 32A is connected to the reaction tank 31A. In FIG. 1, the upstream-end portion of the reaction mass feed line 32A is connected to the bottom portion of the reaction tank 31A, but it can be connected to the side portion of the reaction tank 31A to feed by overflow process. The downstream-end portion of the reaction mass feed line 32A is connected to the reaction tank 31B. In FIG. 1, the downstream-end portion of the reaction mass feed line 32A is connected to the top portion of the reaction tank 31B, but it can also be suitably connected to the side portion or bottom portion of the reaction tank 31B depending on restrictions such as layout. Although not shown, a known feed pump such as a gear pump, non-seal pump, mechanical seal pump, and magnet pump for feeding the reaction mass (primary reaction mass) is provided along the reaction mass feed line 32A.

The reaction mass feed line 32B of the second isocyanate-formation unit 3B feeds the reaction mass (secondary reaction mass) of the 2nd stage isocyanate-formation step from the reaction tank 31B to the de-gassing unit 4. The upstream-end portion of the reaction mass feed line 32B is connected to the reaction tank 31B. In FIG. 1, the upstream-end portion of the reaction mass feed line 32B is connected to the bottom portion of the reaction tank 31B, but it can be connected to the side portion of the reaction tank 31A. The downstream-end portion of the reaction mass feed line 32B is connected to a substantially center in up-down direction of the de-gassing column 41 described later. Although not shown, the above-described feed pump for feeding the reaction mass (secondary reaction mass) is provided along the reaction mass feed line 32B.

The carbonyl chloride feed line 30 feeds carbonyl chloride to the reaction tank 31A and the reaction tank 31B. The downstream-end portion of the carbonyl chloride feed line 30 splits and is connected to the reaction tank 31A and the reaction tank 31B. In FIG. 1, the downstream-end portion of the carbonyl chloride feed line 30 is connected to the top portion of the reaction tank 31A and the reaction tank 31B, but it can be connected to the top portion or the bottom portion of the reaction tank 31A and the reaction tank 31B to feed in the liquid, or it can be connected to the bottom portion of the reaction tank 31A and the reaction tank 31B. The upstream-end portion of the carbonyl chloride feed line 30 is connected to a tank storing the liquefied carbonyl chloride, although not shown.

The de-gassing unit 4 is capable of performing the above-described de-gassing. The de-gassing unit 4 includes a de-gassing column 41, a purge line 45, a condenser 46, a de-gassing mass feed line 42, a circulation line 43, and a reboiler 44.

The de-gassing column 41 separates gas including carbonyl chloride and hydrogen chloride from the reaction mass. The de-gassing column 41 is composed of a known fractionating column such as a tray column, a packed column, and a structured packed column. The downstream-end portion of the reaction mass feed line 32B is connected to a substantially center in up-down direction of the de-gassing column 41.

The purge line 45 is connected to the condenser 46, and separates the solvent contained in the separated gas in the de-gassing column 41 by the condenser 46, and then discharges the gas. The upstream-end portion of the purge line 45 for the gas separated in the de-gassing column 41 is connected to the column-top portion of the de-gassing column 41. Although not shown, the downstream-end portion of the purge line 45 is connected to the carbonyl chloride collector.

The condenser 46 is provided along the purge line 45. The condenser 46 cools and condenses the solvent contained in the gas separated in the de-gassing column 41.

The de-gassing mass feed line 42 feeds the reaction mass after the de-gassing (de-gassed mass) from the de-gassing column 41 to the desolvation unit 5. The upstream-end portion of the de-gassing mass feed line 42 is connected to the column-bottom portion of the de-gassing column 41. The downstream-end portion of the de-gassing mass feed line 42 is connected to a substantially center in up-down direction of the desolvation column 51 described later.

The circulation line 43 returns a portion of the de-gassed mass fed to the de-gassing mass feed line 42 to the de-gassing column 41. The upstream-end portion of the circulation line 43 is connected along the de-gassing mass feed line 42. The downstream-end portion of the circulation line 43 is connected to the column-bottom portion of the de-gassing column 41. Although not shown, the downstream side or the upstream of the connection portion of the circulation line 43 in the de-gassing mass feed line 42 is provided with the above-described feed pump for feeding the de-gassed mass.

The reboiler 44 is provided along the circulation line 43. The reboiler 44 heats the de-gassed mass passing through the circulation line 43. In this manner, the reboiler 44 regulates the internal temperature of the de-gassing column 41. For the reboiler 44, a known heat exchanger, for example, a thermo-syphon system reboiler, a forced circulation reboiler, or a thin-film reboiler can be used.

The desolvation unit 5 is capable of performing the above-described desolvation. The desolvation unit 5 includes a desolvation column 51, a solvent discharge line 55, a condenser 56, a desolvated mass feed line 52, a circulation line 53, and a reboiler 54.

The desolvation column 51 removes the inert solvent from the de-gassed mass. The desolvation column 51 is composed of a known distillation column such as a tray column, a packed column, and a structured packed column, and distills off the inert solvent. The downstream-end portion of the de-gassing mass feed line 42 is connected to a substantially center in up-down direction of the desolvation column 51.

The solvent discharge line 55 discharges the inert solvent that was distilled off in the desolvation column 51 and condensed by the condenser 56. The upstream-end portion of the solvent discharge line 55 is connected to the column-top portion of the desolvation column 51. The downstream-end portion of the solvent discharge line 55 is connected to a tank in which the inert solvent is stored, although not shown. The collected inert solvent is reused, preferably as a reaction solvent in the hydrochloride-producing step and isocyanate step.

The condenser 56 is provided along the solvent discharge line 55. The condenser 56 cools and condenses the inert solvent distilled off by the desolvation column 51.

The desolvated mass feed line 52 feeds the reaction mass after desolvation (desolvated mass) from the desolvation column 51 to the tar-removal unit 6. The upstream-end portion of the desolvated mass feed line 52 is connected to the column-bottom portion of the desolvation column 51. The downstream-end portion of the desolvated mass feed line 52 is connected to a substantially center in up-down direction of a tar-remover 61 described later.

The circulation line 53 returns a portion of the desolvated mass fed to the desolvated mass feed line 52 to the desolvation column 51. The upstream-end portion of the circulation line 53 is connected along the desolvated mass feed line 52. The downstream-end portion of the circulation line 53 is connected to the column-bottom portion of the desolvation column 51. Although not shown, the above-described feed pump for feeding the desolvated mass is provided at a downstream or upstream of the connection portion of the circulation line 53 in the desolvated mass feed line 52.

The reboiler 54 is provided along the circulation line 53. The reboiler 54 heats the desolvated mass that passes through the circulation line 53. In this manner, the reboiler 54 regulates the internal temperature of the desolvation column 51. For the reboiler 54, the above-described heat exchanger can be used.

The tar-removal unit 6 is capable of performing the above-described tar-removal step. The tar-removal unit 6 includes a tar-remover 61, a tar discharge line 62, and a tar-removed mass feed line 63.

The tar-remover 61 separates the tar component from the desolvated mass. The tar-remover 61 is composed of, for example, a known thin film evaporator. The tar-remover 61 includes a casing 61A, a wiper 61B, and an internal condenser 61C.

The casing 61A is provided with a jacket for heating inside the casing 61A and a suction pipe (not shown) for reducing the internal pressure of the casing 61A. A wiper 61B is disposed inside the casing 61A. The wiper 61B is disposed in slightly spaced apart relation from the inner periphery of the casing 61A. The wiper 61B is rotatable by a motor, which is not shown. The internal condenser 61C is composed, for example, of a heat exchanger in which a refrigerant is circulated. The internal condenser 61C is provided at the bottom wall of the casing 61A inside the casing 61A.

The tar discharge line 62 discharges the tar component separated by the tar-remover 61. The upstream-end portion of the tar discharge line 62 is connected to the lower side portion of the casing 61A. The downstream-end portion of the tar discharge line 62 is connected to a tank for storing the tar component, although not shown. From the collected tar component, XDI contained in the tar component can be collected by a known method, and can be introduced into any unit in the plant 1. In this manner, the XDI yield can be improved.

The tar-removed mass feed line 63 feeds the desolvated mass from which the tar component is separated (tar-removed mass) from the tar-remover 61 to the low-boiling removal unit 7. The upstream-end portion of the tar-removed mass feed line 63 is connected to the internal condenser 61C. The downstream-end portion of the tar-removed mass feed line 63 is connected to a substantially center in up-down direction of the low-boiling removal tower 71 described later.

The tar-removed mass feed line 63 is provided with a flowmeter 63A and a control valve 63B. The flowmeter 63A is provided along the tar-removed mass feed line 63. The flowmeter 63A measures the flow rate of the tar-removed mass that passes through the tar-removed mass feed line 63. The control valve 63B is provided at a portion between the flowmeter 63A and the low-boiling removal tower 71 of the tar-removed mass feed line 63. The control valve 63B is capable of opening and closing the tar-removed mass feed line 63. The control valve 63B can regulate, based on the measurement results of the flowmeter 63A, the flow rate of the tar-removed mass that passes through the tar-removed mass feed line 63, that is, the amount of the tar-removed mass fed to the low-boiling removal tower 71.

The low-boiling removal unit 7 is capable of performing the above-described low-boiling removal step. The low-boiling removal unit 7 includes a low-boiling removal tower 71, a suction line 72, a condenser 73, a low-boiling discharge line 74, a column-top reflux line 75, a low-boiling removed mass feed line 76, a column-bottom circulation line 77, and a reboiler 78.

The low-boiling removal tower 71 removes the low-boiling component from the tar-removed mass. The low-boiling removal tower 71 is composed of, for example, a distillation column given as examples in the above-described low-boiling removal step, and distills off the low-boiling component. A substantially center in up-down direction of the low-boiling removal tower 71 is connected to the downstream-end portion of the tar-removed mass feed line 63.

The suction line 72 connects a decompressor such as, for example, a vacuum pump to the low-boiling removal tower 71. The decompressor reduces the pressure inside the low-boiling removal tower 71 through the suction line 72 to regulate the internal pressure of the low-boiling removal tower 71. The upstream-end portion of the suction line 72 is connected to the column-top portion of the low-boiling removal tower 71. The downstream-end portion of the suction line 72 is connected to the decompressor.

The condenser 73 is provided along the suction line 72. The condenser 73 cools and condenses the low-boiling component in gas state passing through the suction line 72.

The low-boiling discharge line 74 discharges the low-boiling component condensed in the condenser 73. The upstream-end portion of the low-boiling discharge line 74 is connected to the condenser 73. The downstream-end portion of the low-boiling discharge line 74 is connected to the tank storing the low-boiling component, although not shown. From the collected low-boiling component, XDI contained in the low-boiling component can be collected by a known method and can be introduced into any unit in the plant 1. In this manner, the XDI yield can be improved.

The low-boiling discharge line 74 is provided with a flowmeter 74A, and a control valve 74B. The flowmeter 74A is provided downstream of the connection portion of the column-top reflux line 75 in the low-boiling discharge line 74. The flowmeter 74A measures the flow rate of the low-boiling component that passed through the low-boiling discharge line 74 and discharged. The control valve 74B is provided downstream of the flowmeter 74A in the low-boiling discharge line 74. The control valve 74B is capable of opening and closing the low-boiling discharge line 74. The control valve 74B can regulates the feed amount of the low-boiling component discharged from the low-boiling discharge line 74 based on the measurement results of the flowmeter 74A.

The column-top reflux line 75 returns a portion of the low-boiling component passing through the low-boiling discharge line 74 to the low-boiling removal tower 71. The upstream-end portion of the column-top reflux line 75 is connected to a portion between the low-boiling removal tower 71 and the flowmeter 74A of the low-boiling discharge line 74. The downstream-end portion of the column-top reflux line 75 is connected to the column-top portion of the low-boiling removal tower 71. The column-top reflux line 75 is provided with a flowmeter 75A. The flowmeter 75A measures the flow rate of the low-boiling component that passes through the column-top reflux line 75 and returned to the low-boiling removal tower 71.

The low-boiling removed mass feed line 76 feeds the tar-removed mass from which the low-boiling component is removed (low-boiling removed mass) to the rectification unit 8 from the low-boiling removal tower 71. The upstream-end portion of the low-boiling removed mass feed line 76 is connected to the column-bottom portion of the low-boiling removal tower 71. The downstream-end portion of the low-boiling removed mass feed line 76 is connected to a substantially center in up-down direction of the rectifying column 81 described later.

The column-bottom circulation line 77 returns a portion of low-boiling removed mass fed to the low-boiling removed mass feed line 76 to the low-boiling removal tower 71. The upstream-end portion of the column-bottom circulation line 77 is connected along the low-boiling removed mass feed line 76. The downstream-end portion of the column-bottom circulation line 77 is connected to the column bottom portion of the low-boiling removal tower 71. Although not shown, the above-described feed pump for feeding a low-boiling removed mass is provided at a downstream of the connection portion of the column-bottom circulation line 77 in the low-boiling removed mass feed line 76.

The reboiler 78 is provided along the column-bottom circulation line 77. The reboiler 78 heats the low-boiling removed mass passing through the column-bottom circulation line 77. In this manner, the reboiler 78 regulates the internal temperature of the low-boiling removal tower 71. The reboiler 78 can use the above-described heat exchanger.

The rectification unit 8 is capable of performing the above-described rectification step. The rectification unit 8 includes a rectifying column 81, a tar discharge line 86, a column-bottom circulation line 87, a reboiler 88, a suction line 82, a condenser 83, a XDI take-out line 84, and a column-top reflux line 85.

The rectifying column 81 distills the tar-removed mass and distills off the XDI composition. The rectifying column 81 is composed of, for example, a distillation column given as examples in the above-described rectification step. A substantially center in up-down direction of the rectifying column 81 is connected to the downstream-end portion of the low-boiling removed mass feed line 76.

The tar discharge line 86 discharges the tar component remained in the rectifying column 81 after the distilling off of the XDI composition from the rectifying column 81. The upstream-end portion of the tar discharge line 86 is connected to the column-bottom portion of the rectifying column 81. The downstream-end portion of the tar discharge line 86 is connected to the tank storing the tar component, although not shown. The tar component of the rectifying column 81 can be introduced into a unit upstream of the low-boiling removal unit 7 as is. In this manner, the XDI yield can be improved.

The column-bottom circulation line 87 returns a portion of the tar component passing through the tar discharge line 86 to the rectifying column 81. The upstream-end portion of the column-bottom circulation line 87 is connected along the tar discharge line 86. The downstream-end portion of the column-bottom circulation line 87 is connected to the column-bottom portion of the rectifying column 81.

The reboiler 88 is provided along the column-bottom circulation line 87. The reboiler 88 heats the tar component passing through the column-bottom circulation line 87. In this manner, the reboiler 88 regulates the column-bottom temperature of the rectifying column 81. For the reboiler 88, the above-described heat exchanger can be used.

The suction line 82 connects, for example, a decompressor such as a vacuum pump to the rectifying column 81. The decompressor reduces the pressure inside the rectifying column 81 through the suction line 82 and regulates the internal pressure of the rectifying column 81. The upstream-end portion of the suction line 82 is connected to the column-top portion of the rectifying column 81. The downstream-end portion of the suction line 82 is connected to the decompressor.

The condenser 83 is provided along the suction line 82. The condenser 83 cools and condenses the gas state XDI composition passing through the suction line 82.

The XDI take-out line 84 feeds the XDI composition condensed in the condenser 83. The upstream-end portion of the XDI take-out line 84 is connected to the condenser 83. The downstream-end portion of the XDI take-out line 84 is connected to the tank storing the XDI composition, although not shown.

The XDI take-out line 84 is provided with a flowmeter 84A and a control valve 84B. The flowmeter 84A is provided downstream of the connection portion of the column-top reflux line 85 in the XDI take-out line 84. The flowmeter 84A measures the flow rate of the XDI composition passing through XDI take-out line 84. The control valve 84B is provided downstream of the flowmeter 84A in the XDI take-out line 84. The control valve 84B is capable of opening and closing the XDI take-out line 84. The control valve 84B can regulate the amount of the XDI composition fed based on the measurement results of the flowmeter 84A from the XDI take-out line 84.

The column-top reflux line 85 returns a portion of the XDI composition passing through the XDI take-out line 84 to the rectifying column 81. The upstream-end portion of the column-top reflux line 85 is connected to a portion between the condenser 83 and the flowmeter 84A of the XDI take-out line 84. The downstream-end portion of the column-top reflux line 85 is connected to the column-top portion of the rectifying column 81. The column-top reflux line 85 is provided with a flowmeter 85A. The flowmeter 85A measures the flow rate of the XDI composition passing through the column-top reflux line 85 and returned to the rectifying column 81.

Particularly, although not shown, a feed line between the mixing vessel, reaction tank, column, and tar-remover can be suitably provided with, as necessary, a control valve or a flowmeter to regulate the residence time in each process and to control the feed flow rate, to stabilize the operation.

(3-2) Plant Operation

Next, description is given below of operation in plant 1.

In plant 1, first, an inert solvent is introduced into the mixing vessel 21. Then, hydrogen chloride gas is continuously fed to the bottom portion of the mixing vessel 21 at the above-described feed ratio, through the hydrogen chloride feed line 24. Also, the above-described amine solution in which XDA is dissolved in the inert solvent is continuously fed to the top portion of the mixing vessel 21 through the amine feed line 22. Then, the inside of the mixing vessel 21 is kept to the above-described salt-forming temperature and salt-forming pressure, and the hydrogen chloride gas and amine solution are stirred and mixed with an impeller (hydrochloride-producing step). In this manner, a slurry containing XDA hydrochloride is produced.

Then, the slurry containing XDA hydrochloride is continuously fed to the top portion of the reaction tank 31A through the hydrochloride feed line 26. That is, while continuously feeding the hydrogen chloride gas and amine solution to the mixing vessel 21, the slurry containing XDA hydrochloride is taken out continuously from the mixing vessel 21 and sent to the reaction tank 31A.

Then, carbonyl chloride is continuously fed at the above-described feed ratio to the top portion of the reaction tank 31A and the reaction tank 31B. Then, while keeping the inside the reaction tank 31A to the above-described reaction temperature and the reaction pressure, the slurry and carbonyl chloride are stirred and mixed (1st-stage isocyanate-formation step). In this manner, XDA hydrochloride is allowed to react with carbonyl chloride to produce a main component XDI, and by-products of DCI and CBI.

Then, the reaction solution (primary reaction mass) containing XDI, DCI, CBI, and inert solvent is continuously fed to the top portion of the reaction tank 31B through the reaction mass feed line 32A. That is, while continuously feeding the slurry and carbonyl chloride to the reaction tank 31A, the primary reaction mass is continuously taken out from the reaction tank 31A and sent to the reaction tank 31B.

Then, while keeping the above-described reaction temperature and reaction pressure inside the reaction tank 31B, in the reaction tank 31B, primary reaction mass and carbonyl chloride are stirred and mixed (2nd stage isocyanate-formation step).

In this manner, the hydrochloride-producing step and isocyanate-formation step are continuously performed.

Then, the secondary reaction mass containing XDI, DCI, CBI, and inert solvent is produced. A total of the residence time in the 2-stage isocyanate-formation step is in the above-described range.

Then, the secondary reaction mass is continuously fed to a substantially center in up-down direction of the de-gassing column 41 through the reaction mass feed line 32B. That is, while continuously feeding the primary reaction mass and carbonyl chloride to the reaction tank 31B, the secondary reaction mass is continuously taken out from the reaction tank 31B and sent to the de-gassing column 41.

Then, the secondary reaction mass is separated into gas containing carbonyl chloride and hydrogen chloride, and a liquid state de-gassed mass containing XDI, DCI, and inert solvent in the de-gassing column 41 (de-gassing).

Then, the de-gassed mass was continuously fed to a substantially center in up-down direction of the desolvation column 51 through the de-gassing mass feed line 42. Then, the inert solvent is distilled off from the de-gassed mass by the desolvation column 51 (desolvation).

Then, the desolvated mass is continuously fed to a substantially center in up-down direction of the tar-remover 61 through the desolvated mass feed line 52. Then, the tar component is removed from the desolvated mass by the tar-remover 61 (tar-removal step).

Then, the tar-removed mass is continuously fed to a substantially center in up-down direction of the low-boiling removal tower 71 through the tar-removed mass feed line 63. Then, in the low-boiling removal unit 7, the low-boiling component is distilled off from the tar-removed mass under the above-described conditions for the low-boiling removal step (column-bottom temperature, column-top temperature, column-top pressure, column-bottom reflux ratio, column-top reflux ratio, and residence time).

To be specific, the vapor mixture containing the low-boiling component is discharged from the column-top portion of the low-boiling removal tower 71 through the suction line 72. Then, the vapor mixture is condensed by the condenser 73. Thereafter, a portion of the condensed liquid containing the low-boiling component is continuously returned to the low-boiling removal tower 71 through the column-top reflux line 75 while regulating the flow rate of the column-top reflux ratio to be within the above-described range. The other portion of the condensed liquid is continuously discharged while regulating the flow rate through the low-boiling discharge line 74.

The low-boiling removed mass is discharged from the low-boiling removal tower 71 through the low-boiling removed mass feed line 76. Then, a portion of the low-boiling removed mass is continuously returned to the low-boiling removal tower 71 through the column-bottom circulation line 77 while achieving the above-described column-bottom temperature and column-bottom reflux ratio. The other portion of the low-boiling removed mass is continuously fed to a substantially center in up-down direction of the rectifying column 81 through the low-boiling removed mass feed line 76.

Then, in the rectification unit 8, under the above-described rectification step conditions (column-bottom temperature, column-top temperature, column-top pressure, column-bottom reflux ratio, column-top reflux ratio, and residence time), the XDI composition is continuously taken out as a fraction from the low-boiling removed mass.

To be specific, the gas state XDI composition is discharged from the column-top portion of the rectifying column 81 through the suction line 82. Then, the gas state XDI composition is condensed by the condenser 83. Thereafter, a portion of the XDI composition is continuously returned to the rectifying column 81 through the column-top reflux line 85 while regulating the flow rate so that the column-top reflux ratio is within the above-described range. The other portion of the XDI composition is continuously taken out through the XDI take-out line 84 while regulating the flow rate.

The distillation residue of the rectifying column 81 (tar component) is discharged from the column-bottom portion of the rectifying column 81 through the tar discharge line 86. Then, a portion of the distillation residue (tar component) is continuously returned to the rectifying column 81 while achieving the above-described column-bottom temperature and column-bottom reflux ratio.

In the above-described manner, a XDI composition (purified XDI) as a product is continuously produced in the plant 1.

4. Polyisocyanate Component and Active Hydrogen Group-Containing Component

Such a XDI composition is modified, as necessary, by a known method, and contained in the polyisocyanate component. The polyisocyanate component and active hydrogen group-containing component are suitably used as a polyurethane resin material.

The polyisocyanate component contains a XDI composition and/or a xylylenediisocyanate-modified composition (hereinafter referred to as XDI modified composition), which is a modified XDI composition, and preferably consists of the XDI composition and/or XDI modified composition.

The XDI modified composition is produced by modifying the XDI composition, and contains at least one of the functional group of (a) to (i) below:
(a) isocyanurate group,
(b) allophanate group,
(c) biuret group,
(d) urethane group,
(e) urea group,
(f) iminooxadiazinedione group,
(g) uretdione group,
(h) uretonimine group, and
(i) carbodiimide group.

That is, the XDI modified composition contains a functional group (a) to (i), i.e., modified XDI, and DCI.

To be more specific, the XDI modified composition containing the above-described functional group of (a) (isocyanurate group) contains a XDI trimer, and can be produced by, for example, allowing the XDI composition to react in the presence of a known isocyanurate-forming catalyst to subject the XDI to isocyanurate-formation (for example, trimerization).

The XDI modified composition containing the above-described functional group of (b) (allophanate group) contains an allophanate-modified XDI, and can be produced by, for example, allowing the XDI composition to react with alcohol, and then further allowing them to react in the presence of a known allophanate-formation catalyst.

The XDI modified composition containing the above-described functional group of (c) (biuret group) contains a biuret-modified XDI, and can be produced by, for example, allowing the XDI composition to react with, for example, water, tertiary alcohol (for example, t-butylalcohol, etc.), and secondary amine (for example, dimethylamine, diethylamine, etc.), and then further allowing them to react in the presence of a known biuret-forming catalyst.

The XDI modified composition containing the above-described functional group of (d) (urethane group) contains a polyol-modified XDI, and can be produced by, for example, allowing the XDI composition to react with a polyol component (for example, trimethylolpropane, etc.).

The XDI modified composition containing the above-described functional group of (e) (urea group) contains a polyamine-modified XDI, and can be produced by, for example, allowing the XDI composition to react with water, and a polyamine component (described later).

The XDI modified composition containing the above-described functional group of (f) (iminooxadiazinedione group) contains an iminooxadiazinedione-modified XDI (asymmetric trimer), and can be produced by, for example, allowing the XDI composition to react in the presence of a known iminooxadiazinedione-formation catalyst, and then subjecting XDI to iminooxadiazinedione-formation (for example, trimerization).

The XDI modified composition containing the above-described functional group of (g) (uretdione group) contains a uretdione-modified XDI, and can be produced by, for example, heating the XDI composition to about 90° C. to 200° C., or allowing it to react in the presence of a known uretdione-formation catalyst, and then subjecting the XDI to uretdione-formation (for example, dimerization).

The XDI modified composition containing the above-described functional group of (h) (uretonimine group) contains a uretonimine-modified XDI, and can be produced by, for example, allowing the XDI composition to react in the presence of a known carbodiimide-formation catalyst to form a carbodiimide group, and then adding XDI to the carbodiimide group.

The XDI modified composition containing the above-described functional group of (i) (carbodiimide group) contains a carbodiimide-modified XDI, and can be produced by, for example, allowing the XDI composition to react in the presence of a known carbodiimide-formation catalyst.

The XDI modified composition containing at least one functional group of the above-described (a) to (i) may suffice, or the XDI modified composition may contain two or more of these. Such a XDI modified composition can be produced by suitably combining the above-described reactions. The XDI modified composition can be used singly, or can be used in combination of two or more.

The XDI composition can also be used as a block XDI composition, in which free isocyanate groups contained in the molecule are blocked by a blocking agent. That is, the polyisocyanate component can contain the block XDI composition.

The block XDI composition is produced by, for example, allowing the XDI composition to react with the blocking agent.

Examples of the blocking agent include oxime-based, phenol-based, alcohol-based, imine-based, amine-based, carbamic acid-based, urea-based, imidazole-based, imide-based, mercaptan-based, active methylene-based, acid amide-based (lactam-based), and bisulfites-based blocking agents.

Examples of the oxime-based blocking agent include formaldoxime, acetaldoxime, methylethylketoxime, cyclohexanoneoxime, acetoxime, diacetyl monoxime, benzophenone oxime, 2,2,6,6-tetramethylcyclohexanoneoxime, diisopropylketoneoxime, methyltert-butylketoneoxime, diisobutylketoneoxime, methylisobutylketoneoxime, methylisopropylketoneoxime, methyl 2,4-dimethylpentylketoneoxime, methyl 3-ethylheptylketoneoxime, methylisoamylketoneoxime, n-amylketoneoxime, 2,2,4,4-tetramethyl-1,3-cyclobutanedionemonooxime, 4,4'-dimethoxybenzophenoneoxime, and 2-heptanoneoxime.

Examples of the phenol-based blocking agent include phenol, cresol, ethylphenol, n-propylphenol, isopropylphenol, n-butylphenol, sec-butylphenol, tert-butylphenol, n-hexylphenol, 2-ethylhexylphenol, n-octylphenol, n-nonylphenol, di-n-propylphenol, diisopropylphenol, isopropylcresol, di-n-butylphenol, di-sec-butylphenol, di-tert-butylphenol, di-n-octylphenol, di-2-ethylhexylphenol, di-n-nonylphenol, nitrophenol, bromophenol, chlorophenol, fluorophenol, dimethylphenol, styrenated phenol, methylsalicylate, 4-hydroxybenzoic acidmethyl, 4-hydroxybenzoic acidbenzyl, hydroxybenzoic acid 2-ethylhexyl, 4-[(dimethylamino)methyl] phenol, 4-[(dimethylamino)methyl]nonylphenol, bis (4-hydroxyphenyl)acetic acid, pyridinol, 2- or 8-hydroxyquinoline, 2-chloro-3-pyridinol, and pyridine-2-thiol.

Examples of the alcohol-based blocking agent include methanol, ethanol, 2-propanol, n-butanol, sec-butanol, 2-ethylhexylalcohol, 1- or 2-octanol, cyclohexylalcohol, ethylene glycol, benzylalcohol, 2,2,2-trifluoroethanol, 2,2,2-trichloroethanol, 2-(hydroxymethyl)furan, 2-methoxyethanol, methoxypropanol, 2-ethoxyethanol, n-propoxyethanol, 2-butoxyethanol, 2-ethoxyethoxyethanol, 2-ethoxybutoxyethanol, butoxyethoxyethanol, 2-ethylhexyloxyethanol, 2-butoxyethylethanol, 2-butoxyethoxyethanol, N,N-dibutyl-2-hydroxyacetamide, N-hydroxysuccinimide, N-morpholineethanol, 2,2-dimethyl-1,3-dioxolane-4-methanol, 3-oxazolidineethanol, 2-hydroxymethylpyridine, furfuryl alcohol, 12-hydroxystearic acid, triphenylsilanol, and methacrylic acid 2-hydroxyethyl.

Examples of the imine-based blocking agent include ethylene-imine, polyethylene-imine, 1,4,5,6-tetrahydropyrimidine, and guanidine.

Examples of the amine-based blocking agent include dibutylamine, diphenylamine, aniline, N-methylaniline, carbazole, bis (2,2,6,6-tetramethylpiperidinyl)amine, di-n-propylamine, diisopropylamine, isopropylethylamine, 2,2,4-, or 2,2,5-trimethylhexamethyleneamine, N-isopropylcyclohexylamine, dicyclohexylamine, bis (3,5,5-trimethylcyclohexyl)amine, piperidine, 2,6-dimethylpiperidine, 2,2,6,6-tetramethylpiperidine, (dimethylamino)-2,2,6,6-tetramethylpiperidine, 2,2,6,6-tetramethyl-4-piperidine, 6-methyl-2-piperidine, and 6-aminocaproic acid.

For the carbamic acid-based blocking agent, for example, N-phenylphenyl carbamate is used.

For the urea-based blocking agent, for example, urea, thiourea, and ethylene urea are used.

For the imidazole-based blocking agent, for example, imidazole, 2-methyl imidazole, 2-ethyl-4-methyl imidazole, 2-isopropyl imidazole, 2,4-dimethyl imidazole, 4-methyl imidazole, 2-phenylimidazole, 4-methyl-2-phenylimidazole, pyrazole, 3-methylpyrazole, 3,5-dimethylpyrazole, 1,2,4-triazole, and benzotriazole are used.

For the imide-based blocking agent, for example, succinic acidimide, maleic acidimide, and phthalimide are used.

For the mercaptan-based blocking agent, for example, butylmercaptan, dodecylmercaptan, and hexylmercaptan are used.

Examples of the active methylene-based blocking agent include Meldrum's acid, malonic aciddimethyl, methyl acetoacetate, ethyl acetoacetate, malonic acid di-tert-butyl, malonic acid 1-tert-butyl 3-methyl, malonic aciddiethyl, acetoacetic acidtert-butyl, 2-acetoacetoxyethylmethacrylate, acetylacetone, and cyanoethyl acetate.

Examples of the acid amide (lactam) blocking agent include, acetanilid, N-methylacetamide, acetic acidamide, ε-caprolactam, δ-valerolactam, γ-butyrolactam, pyrrolidone, 2,5-piperazinedione, and laurolactam.

The blocking agent is not limited to the above-described ones, and for example, other blocking agents such as benzoxazolone, isatoic acid anhydride, and tetrabutylphosphonium acetate can also be used. The blocking agent can be used singly, or can be used in combination of two or more.

The XDI composition can be used as a hydrophilic block XDI composition, in which free isocyanate groups contained in the molecule are blocked by the blocking agent, and dispersed or dissolved in water. That is, the polyisocyanate component can contain hydrophilic block XDI composition.

The hydrophilic block XDI composition is produced by, for example, blocking a portion of the free isocyanate groups in the XDI composition by the blocking agent, and then allowing the isocyanate group remained without being blocked by the blocking agent to react with a compound (hereinafter referred to as hydrophilic group-containing active hydrogen compound) containing both a hydrophilic group and an active hydrogen group.

For the blocking agent, for example, the above-described blocking agent is used.

The hydrophilic group-containing active hydrogen compound is a compound containing both at least one hydrophilic group and at least one active hydrogen group. For the hydrophilic group, for example, an anionic group, cationic group, and nonionic group are used. The active hydrogen group is a group that reacts with the isocyanate group, and for example, a hydroxyl group, amino group, carboxyl group, and epoxy group are used.

For the hydrophilic group-containing active hydrogen compound, to be more specific, a carboxylic acid group-containing active hydrogen compound, sulfonic acid group-containing active hydrogen compound, hydroxyl group-containing active hydrogen compound, hydrophilic group-containing polybasic acid, and polyoxyethylene group-containing active hydrogen compound are used. The hydrophilic group-containing active hydrogen compound can be used singly, or can be used in combination of two or more.

For the active hydrogen group-containing component, for example, a polyol component (component mainly containing polyol having two or more hydroxyl groups), polythiol component (component mainly containing polythiol having two or more mercapto groups (thiol group)), and polyamine component (compound mainly containing polyamine having two or more amino groups) are used.

For the polyol component, for example, a low molecular-weight polyol and a high molecular weight polyol are used.

The low molecular-weight polyol is a compound having two or more hydroxyl groups and a number average molecular weight of 60 or more and less than 400. Examples of the low molecular-weight polyol include dihydric alcohols including ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, alkane (7 to 22) diol, diethylene glycol, triethylene glycol, dipropylene glycol, 3-methyl-1,5-pentanediol, alkane-1,2-diol (C (number of carbon atoms, the same applies in the following) 17 to 20), isosorbide, 1,3- or 1,4-cyclohexanedimethanol and a mixture thereof, 1,4-cyclohexanediol, hydrogenated bisphenol A, 1,4-dihydroxy-2-butene, 2,6-dimethyl-1-octene-3,8-diol, and bisphenol A; trihydric alcohols such as glycerine and trimethylolpropane; tetrahydric alcohols such as tetramethylolmethane (pentaerythritol) and diglycerol; pentahydric alcohols such as xylitol; hexahydric alcohols including sorbitol, mannitol, allitol, iditol, dulcitol, altritol, inositol, and dipentaerythritol; heptahydric alcohols such as perseitol; and octahydric alcohols including sucrose.

The low molecular-weight polyol also include polyalkyleneoxide (including random and/or block copolymer of two or more alkylene oxides) having a number average molecular weight of 60 or more and less than 400 produced by adding alkyleneoxide such as ethyleneoxide and propyleneoxide with the above-described alcohol as the initiator.

The high molecular weight polyol is a compound having two or more hydroxyl groups and a number average molecular weight of 400 or more, and for example, 10000 or less, preferably 5000 or less. Examples of the high molecular weight polyol include polyetherpolyol, polyesterpolyol, polycarbonatepolyol, polyurethane polyol, epoxypolyol, vegetable oil polyol, polyolefin polyol, acrylic polyol, silicone polyol, fluorine polyol, and vinyl monomer-modified polyol.

For the polyetherpolyol, for example, polyoxy (C2 to 3) alkylenepolyol, polytetramethylene ether glycol, and polytrimethyleneether glycol are used.

For the polyoxy (C2 to 3) alkylenepolyol, for example, an addition polymerization product (including random and/or block copolymer of two or more alkylene oxides) of C2 to 3 alkylene oxides such as ethyleneoxide and propyleneoxide using the above-described low molecular-weight polyol as the initiator is used. For the polyoxy (C2 to 3) alkylene, to be specific, polyethylene glycol, polypropylene glycol, and polyethylenepolypropylene copolymer are also used.

For the polytetramethylene ether glycol, for example, a ring-opening polymerization product produced by cationic polymerization of tetrahydrofuran (polytetramethylene ether glycol), and noncrystalline polytetramethylene ether glycol produced by copolymerizing a tetrahydrofuran polymerization unit with the above-described dihydric alcohol are used.

Furthermore, plant derived polytetramethylene ether glycol using tetrahydrofuran produced from a plant derived material such as furfural as a starting material can also be used.

Examples of the polytrimethylene ether glycol include polyol produced from polycondensation of plant derived 1,3-propanediol.

Examples of the polyesterpolyol include a polycondensate produced by allowing the above-described low-molecular-weight polyol (preferably, dihydric alcohol) to react with polybasic acid (preferably dibasic acid) under known conditions.

Examples of the polybasic acid include saturated aliphatic dicarboxylic acids (C11 to 13) such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, and sebacic acid; unsaturated aliphatic dicarboxylic acids such as maleic acid, fumaric acid, and itaconic acid; aromatic dicarboxylic acids such as orthophthalic acid, isophthalic acid, terephthalic acid, toluenedicarboxylic acid, and naphthalenedicarboxylic acid; alicyclic dicarboxylic acids such as hexahydrophthalic acid; other carboxylic acids such as dimer acid, hydrogenated dimer acid, and het acid, and acid anhydrides derived from these carboxylic acids such as oxalic anhydride, succinic anhydride, maleic anhydride, phthalic anhydride, 2-alkyl (C12 to C 18) succinic anhydride, tetrahydrophthalic anhydride, trimellitic anhydride, and hallides derived from carboxylic acids thereof such as oxalyl dichloride, adipoyl dichloride, and sebacoyl dichloride.

Examples of the polyester polyol include vegetable oil polyester polyols obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, etc.) with the above-described low-molecular-weight polyol under known conditions.

Examples of the polyester polyol further include lactone-based polyester polyols such as polycaprolactone polyol and polyvalerolactone polyol obtained by ring-opening polymerization of lactones such as ε-caprolactone, γ-valerolactone, etc. using the above-described low-molecular-weight polyols (preferably, dihydric alcohol) as an initiator; and a copolymer of a polycaprolactone polyol or polyvalerolactone polyol with the above-described dihydric alcohol.

Examples of the polycarbonatepolyol include a ring-opening polymerization product of ethylenecarbonate using the above-described low-molecular-weight polyol (preferably, dihydric alcohol) as an initiator, and noncrystalline polycarbonatepolyol produced by copolymerizing a ring-opening polymerization product with the above-described dihydric alcohol.

Examples of the polyurethane polyol include polyesterpolyurethane polyol, polyetherpolyurethane polyol, polycarbonatepolyurethane polyol, and polyesterpolyetherpolyurethane polyol produced by allowing polyesterpolyol, polyetherpolyol and/or polycarbonatepolyol produced as described above to react with the above-described polyisocyanate (including xylylenediisocyanate, the same applies in the following) at the equivalent ratio (OH/NCO) of the hydroxyl group relative to the isocyanate group of more than 1.

Examples of the epoxy polyol include epoxy polyols obtained by reaction of the above-described low-molecular-weight polyols with polyfunctional halohydrin such as epichlorohydrin and β-methylepichlorohydrin.

Examples of the vegetable oil-based polyol include hydroxyl group-containing vegetable oils such as castor oil and coconut oil. For example, castor oil polyol, or ester-modified castor oil polyol produced by reaction of castor oil polyol with polypropylenepolyol.

Examples of the polyolefin polyol include polybutadiene polyol, and a partially saponified ethylene-vinyl acetate copolymer.

Examples of the acrylic polyol include copolymers obtained by copolymerizing hydroxyl group-containing acrylate with a vinyl monomer copolymerizable with the hydroxyl group-containing acrylate.

Examples of the hydroxyl group-containing acrylate include 2-hydroxyethyl (meth)acrylate, hydroxypropyl (meth)acrylate, hydroxybutyl (meth)acrylate, 2,2-dihydroxymethylbutyl (meth)acrylate, polyhydroxyalkyl maleate, and polyhydroxyalkyl fumarate. Preferably 2-hydroxyethyl (meth)acrylate is used.

Examples of the copolymerizable vinyl monomer include alkyl (meth)acrylates (of 1 to 12 carbon atoms) such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, isopentyl (meth)acrylate, hexyl (meth)acrylate, isononyl (meth)acrylate, 2-ethylhexyl (meth)acrylate, cyclohexyl acrylate, and isobornyl (meth)acrylate; aromatic vinyl monomers such as styrene, vinyltoluene, and α-methylstyrene; vinyl cyanides such as (meth) acrylonitrile; vinyl monomers containing carboxyl groups such as (meth)acrylic acid, fumaric acid, maleic acid, and itaconic acid, or alkyl esters thereof; alkane polyol poly (meth)acrylates such as ethylene glycol di(meth)acrylate, butylene glycol di(meth)acrylate, hexanediol di(meth)acrylate, oligo-ethylene glycol di(meth)acrylate, trimethylol propane di(meth)acrylate, and trimethylol propane tri(meth) acrylate; and vinyl monomers containing isocyanate groups such as 3-(2-isocyanato-2-propyl)-α-methylstyrene.

The acrylic polyol can be obtained by copolymerizing these hydroxyl group-containing acrylates and copolymerizable vinyl monomers in the presence of a suitable solvent and a suitable polymerization initiator.

The acrylic polyol include silicone polyol and fluorine polyol.

Examples of the silicone polyol include acrylic polyol in which as the copolymerizable vinyl monomer, for example, a silicone compound containing a vinyl group such as γ-methacryloxypropyltrimethoxysilane is blended in the above-described copolymerization of acrylic polyol.

Examples of the fluorinepolyol include acrylic polyol in which as the copolymerizable vinyl monomer, for example, a fluorine compound containing a vinyl group such as tetrafluoroethylene and chlorotrifluoroethylene is blended in the above-described copolymerization of acrylic polyol.

The vinyl monomer-modified polyol can be obtained by reaction between the above-mentioned high-molecular-weight polyol and a vinyl monomer such as the above-described alkyl (meth)acrylate.

These polyol components may be used singly or in a combination of two or more.

Examples of the polythiol component include aliphatic polythiols, aromatic polythiols, heterocyclic ring-containing polythiols, aliphatic polythiols containing a sulfur atom other than the mercapto group, aromatic polythiols containing a sulfur atom other than the mercapto group, and heterocyclic ring-containing polythiols containing a sulfur atom other than the mercapto group.

Examples of the aliphatic polythiol include methanedithiol, 1,2-ethanedithiol, 1,1-propane dithiol, 1,2-propane dithiol, 1,3-propane dithiol, 1,4-butanedithiol, 1,5-pentanedithiol, 2,2-propane dithiol, 1,6-hexanedithiol, 1,2,3-propane trithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1-methylcyclohexane-2,3-dithiol, bicyclo[2,2,1]hepta-exo-cis-2,3-dithiol, tetrakis (mercaptomethyl) methane, 1,1-bis (mercaptomethyl)cyclohexane, thiomalic acidbis (2-mercaptoethylester), 2,3-dimercaptosuccinic acid (2-mercaptoethylester), 2,3-dimercapto-1-propanol (2-mercaptoacetate), 2,3-dimercapto-1-propanol (3-mercaptopropionate), diethylene glycolbis (2-mercaptoacetate), diethylene glycolbis (3-mercaptopropionate), 1,2-dimercaptopropylmethylether, 2,3-dimercaptopropylmethylether, 2,2-bis (mercaptomethyl)-1,3-propane dithiol, bis (2-mercaptoethyl)ether, ethylene glycolbis (2-mercaptoacetate), ethylene glycolbis (3-mercaptopropionate), trimethylolpropanebis (2-mercaptoacetate), trimethylolpropanebis (3-mercaptopropionate), 3-mercapto-1,2-propanediolbis (2-mercaptoacetate), 3-mercapto-1,2-propanedioldi(3-mercaptopropionate), trimethylolpropanetris (2-mercaptoacetate), trimethylolpropane (3-mercaptopropionate), trimethylolethanetris (2-mercaptoacetate), trimethylolethanetris (3-mercaptopropionate), pentaerythritoltetrakis (2-mercaptoacetate), pentaerythritoltetrakis (3-mercaptopropionate), glycerinetris (2-mercaptoacetate), glycerinetris (3-mercaptopropionate), 1,4-cyclohexanediolbis (2-mercaptoacetate), and 1,4-cyclohexanediolbis (3-mercaptopropionate).

Examples of the aromatic polythiol include 1,2-dimercaptobenzene, 1,3-dimercaptobenzene, 1,4-dimercaptobenzene, 1,2-bis (mercaptomethyl)benzene, 1,3-bis (mercaptomethyl) benzene, 1,4-bis (mercaptomethyl)benzene, 1,2-bis (mercaptoethyl)benzene, 1,3-bis (mercaptoethyl)benzene, 1,4-bis (mercaptoethyl)benzene, 1,2-bis (mercaptomethyleneoxy)benzene, 1,3-bis (mercaptomethyleneoxy)benzene, 1,4-bis (mercaptomethyleneoxy)benzene, 1,2-bis (mercaptoethyleneoxy)benzene, 1,3-bis (mercaptoethyleneoxy)benzene, 1,4-bis (mercaptoethyleneoxy)benzene, 1,2,3-trimercaptobenzene, 1,2,4-trimercaptobenzene, 1,3,5-trimercaptobenzene, 1,2,3-tris (mercaptomethyl)benzene, 1,2,4-tris (mercaptomethyl)benzene, 1,3,5-tris (mercaptomethyl)benzene, 1,2,3-tris (mercaptoethyl)benzene, 1,2,4-tris (mercaptoethyl)benzene, 1,3,5-tris (mercaptoethyl)benzene, 1,2,3-tris (mercaptomethyleneoxy)benzene, 1,2,4-tris (mercaptomethyleneoxy)benzene, 1,3,5-tris (mercaptomethyleneoxy)benzene, 1,2,3-tris (mercaptoethyleneoxy) benzene, 1,2,4-tris (mercaptoethyleneoxy)benzene, 1,3,5-tris (mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis (mercaptomethyl) benzene, 1,2,3,5-tetrakis (mercaptomethyl)benzene, 1,2,4,5-tetrakis (mercaptomethyl)benzene, 1,2,3,4-tetrakis (mercaptoethyl)benzene, 1,2,3,5-tetrakis (mercaptoethyl) benzene, 1,2,4,5-tetrakis (mercaptoethyl)benzene, 1,2,3,4-tetrakis (mercaptomethyleneoxy)benzene, 1,2,3,5-tetrakis (mercaptomethyleneoxy)benzene, 1,2,4,5-tetrakis (mercaptoethyleneoxy)benzene, 1,2,3,4-tetrakis (mercaptoethyleneoxy)benzene, 1,2,3,5-tetrakis (mercaptoethyleneoxy)benzene, 1,2,4,5-tetrakis (mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl)propane-2,2-dithiol, 1,3-diphenylpropane-2,2-dithiol, phenylmethane-1,1-dithiol, and 2,4-di(p-mercaptophenyl) pentane.

Examples of the heterocyclic ring-containing polythiol include 2-methylamino-4,6-dithiol-sym-triazine, 2-ethylamino-4,6-dithiol-sym-triazine, 2-amino-4,6-dithiol-sym-triazine, 2-molpholino-4,6-dithiol-sym-triazine, 2-cyclohexylamino-4,6-dithiol-sym-triazine, 2-methoxy-4,6- dithiol-sym-triazine, 2-phenoxy-4,6-dithiol-sym-triazine, 2-thiobenzeneoxy-4,6-dithiol-sym-triazine, and 2-thiobutyloxy-4,6-dithiol-sym-triazine.

Examples of the aliphatic polythiols containing a sulfur atom other than the mercapto group include bis (mercaptomethyl)sulfide, bis (mercaptoethyl)sulfide, bis (mercaptopropyl)sulfide, bis (mercaptomethylthio)methane, bis (2-mercaptoethylthio)methane, bis (3-mercaptopropylthio) methane, 1,2-bis (mercaptomethylthio)ethane, 1,2-bis (2-mercaptoethylthio)ethane, 1,2-bis (3-mercaptopropyl) ethane, 1,3-bis (mercaptomethylthio)propane, 1,3-bis (2-mercaptoethylthio)propane, 1,3-bis (3-mercaptopropylthio)propane, 1,2,3-tris (mercaptomethylthio)propane, 1,2,3-tris (2-mercaptoethylthio)propane, 1,2,3-tris (3-mercaptopropylthio)propane, tetrakis (mercaptomethylthiomethyl) methane, tetrakis (2-mercaptoethylthiomethyl)methane, tetrakis (3-mercaptopropylthiomethyl)methane, bis (2,3-dimercaptopropyl)sulfide, 2,5-dimercapto-1,4-dithiane, 2,5-dimercaptomethyl-1,4-dithiane, bis (mercaptomethyl)disulfide, bis (mercaptoethyl)disulfide, bis (mercaptopropyl) disulfide, and thioglycolic acid and mercaptopropionic acid esters of the above-mentioned compounds, hydroxymethylsulfidebis (2-mercaptoacetate), hydroxymethylsulfidebis (3-mercaptopropionate), hydroxyethylsulfidebis (2-mercaptoacetate), hydroxyethylsulfidebis (3-mercaptopropionate), hydroxypropylsulfidebis (2-mercaptoacetate), hydroxypropylsulfidebis (3-mercaptopropionate), hydroxymethyldisulfidebis (2-mercaptoacetate), hydroxymethyldisulfidebis (3-mercaptopropionate), hydroxyethyldisulfidebis (2-mercaptoacetate), hydroxyethyldisulfidebis (3-mercaptopropionate), hydroxypropyldisulfidebis (2-mercaptoacetate), hydroxypropyldisulfidebis (3-mercaptopropionate), 2-mercaptoethylether bis (2-mercaptoacetate), 2-mercaptoethylether bis (3-mercaptopropionate), 1,2-bis[(2-mercaptoethyl)thio]-3-mercaptopropane, 1,4-dithiane-2,5-diolbis (2-mercaptoacetate), 1,4-dithiane-2,5-diolbis (3-mercaptopropionate), thiodiglycollic acidbis (2-mercaptoethylester), thiodipropionic acidbis (2-mercaptoethylester), 4,4-thiodibutyric acid bis (2-mercaptoethylester), dithiodiglycollic acidbis (2-mercaptoethylester), dithiodipropionic acidbis (2-mercaptoethylester), 4,4-di thiodibutyric acid bis (2-mercaptoethylester), thioglycolic acidbis (2,3-dimercaptopropylester), thiodipropionic acidbis (2,3-dimercaptopropylester), dithioglycolic acidbis (2,3-dimercaptopropylester), dithiodipropionic acidbis (2,3-dimercaptopropylester), 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis (mercaptomethylthio)propane, 4,6-bis (mercaptomethylthio)-1,3-dithiane, and 2-(2,2-bis (mercaptomethylthio)ethyl)-1,3-dithietane.

Examples of the aromatic polythiol containing a sulfur atom other than the mercapto group include 1,2-bis (mercaptomethylthio)benzene, 1,3-bis (mercaptomethylthio)benzene, 1,4-bis (mercaptomethylthio)benzene, 1,2-bis (mercaptoethylthio)benzene, 1,3-bis (mercaptoethylthio) benzene, 1,4-bis (mercaptoethylthio)benzene, 1,2,3-tris (mercaptomethylthio)benzene, 1,2,4-tris (mercaptomethylthio)benzene, 1,3,5-tris (mercaptomethylthio)benzene, 1,2,3-tris (mercaptoethylthio)benzene, 1,2,4-tris (mercaptoethylthio)benzene, 1,3,5-tris (mercaptoethylthio)benzene, 1,2,3,4-tetrakis (mercaptomethylthio)benzene, 1,2,3,5-tetrakis (mercaptomethylthio)benzene, 1,2,4,5-tetrakis (mercaptomethylthio)benzene, 1,2,3,4-tetrakis (mercaptoethylthio)benzene, 1,2,3,5-tetrakis (mercaptoethylthio)benzene, 1,2,4,5-tetrakis (mercaptoethylthio)benzene, and nuclear alkylated products of the above.

Examples of the heterocyclic ring-containing polythiol containing a sulfur atom other than the mercapto group include 3,4-thiophenedithiol and 2,5-dimercapto-1,3,4-thiadiazole, and thioglycolic acid esters and mercaptopropionic acid esters of the above-mentioned compounds.

Further examples of the polythiol component include halogen substituted compound of these polythiols, such as chlorine-substituted compound and bromine-substituted compound of the polythiol components.

These polythiol components may be used singly or in a combination of two or more.

For the polyamine component, for example, a low molecular-weight polyamine and a high molecular weight polyamine are used.

The low molecular-weight polyamine is a compound having two or more amino groups and a number average molecular weight of 60 or more and less than 350. For the low molecular-weight polyamine, for example, a low molecular-weight diamine, low molecular-weight triamine, and low molecular-weight polyamine having four or more amino groups are used.

Examples of the low molecular-weight diamine include aliphatic diamines such as ethylene diamine, 1,3-propane diamine, 1,3- or 1,4-butanediamine, 1,5-pentamethylenediamine, and 1,6-hexamethylenediamine; alicyclic diamines including 1,4-cyclohexanediamine, 3-aminomethyl-3,5,5-trimethylcyclohexylamine (isophoronediamine), 4,4'-dicyclohexylmethanediamine, 2,5(2,6)-bis (aminomethyl)bicyclo[2.2.1]heptane, and 1,3-bis (aminomethyl)cyclohexane; aromatic diamines including o, m or p-tolylenediamine (TDA, OTD), 3,5-diethyltoluene-2,4-diamine, 3,5-diethyltoluene-2,6-diamine, a mixture of 3,5-diethyltoluene-2,4-diamine and 3,5-diethyltoluene-2,6-diamine (trade name: ETHACURE®100, manufactured by ALBEMARLE JAPAN CORPORATION), and dimethylthiotoluenediamine (trade name: ETHACURE®300 manufactured by ALBEMARLE JAPAN CORPORATION).

For the low molecular-weight triamine, for example, diethylene triamine is used. For the low molecular-weight polyamine having four or more amino groups, for example, triethylenetetramine and tetraethylenepentamine are used.

The high molecular weight polyamine is a compound having two or more amino groups and a number average molecular weight of 350 or more, and for example, 10000 or less, preferably 5000 or less. For the high molecular weight polyamine, for example, polyetherpolyamine such as polyoxyalkyleneether diamine is used. Polyetherpolyamine can be obtained as a commercially available product, to be more specific, for example, PEG #1000 diamine manufactured by NOF CORPORATION, JEFFAMINE series manufactured by Huntsman International LLC., and Baxxodur series manufactured by BASF are used.

These polyamine components may be used singly or in a combination of two or more.

Of these active hydrogen group-containing components, preferably, the polyol component and the polythiol component are used.

To the active hydrogen group-containing component, as necessary, for example, a known polyamine, a known monol, a known monoamine can be blended at a suitable ratio.

5. Use of Resin

The resin (polyurethane resin), which is a reaction product of the polyisocyanate component containing the XDI composition and/or XDI modified composition with the active hydrogen group-containing component can be used in all applications where polyurethane resin is used.

In the reaction of the polyisocyanate component with the active hydrogen group-containing component, when the equivalent ratio of the active hydrogen group relative to the isocyanate group is less than 1, an isocyanate group-terminated polymer having an isocyanate group at its molecular terminal is produced, and when the equivalent ratio of the active hydrogen group relative to the isocyanate group is more than 1, an active hydrogen group-terminated polymer having an active hydrogen group at its molecular terminal is produced. The isocyanate group-terminated polymer and the active hydrogen group-terminated polymer are contained in the resin (polyurethane resin). The isocyanate group-terminated polymer is a one component curable resin.

The resin can be used in the following: to be specific, ink, transfer foil, pressure-sensitive adhesive, binder, gel, elastomer, foam, adhesive, one-component curable sealant, RIM molded article, microcellular polyurethane, various microcapsules, optical material, aqueous resin, thermosetting resin, active energy ray (for example, electron beam, ultraviolet ray, etc.) curable resin, artificial and synthetic leather, slush powder, robot member, mobility members, health care materials, substrate resin for carbon-fiber reinforced plastic (CFRP), transparent rubber, transparent hard resin, waterproof material, film, sheet, tube, blade, speaker, sensors, organic EL members, solar cell members, android members, wearable members, sporting goods, leisure goods, medical products, nursing care goods, housing materials, acoustic material, lighting members, chandelier, street light, gasket, vibration proofing and damping/base isolation members, sound insulation material, daily use articles, miscellaneous goods, cushion, bedding, stress absorbing material, stress relieving material, automobile interior and exterior members, transportation members, OA device members, surface protection members for miscellaneous goods, self-repairing material, and healthcare products.

Such polyurethane resin can be used for an elastomer, foam, one-component curable sealant, and optical material, which are described in detail in the following.

(5-1) Elastomer

Examples of the elastomer include thermoplastic urethane elastomer (TPU), thermosetting urethane elastomer (TSU), and millable polyurethane elastomer.

The elastomer includes a soft segment formed by reaction between XDI and the high molecular weight polyol, and a hard segment formed by reaction between XDI and the low molecular-weight polyol and/or low molecular-weight polyamine.

Such an elastomer is produced by reaction of, for example, the polyisocyanate component, high molecular weight polyol (active hydrogen group-containing component), and low molecular-weight polyol and/or low molecular-weight polyamine (active hydrogen group-containing component). That is, the polyisocyanate component, high molecular weight polyol, low molecular-weight polyol and/or low molecular-weight polyamine are elastomer ingredients.

The polyisocyanate component as the elastomer ingredient contains, for example, the XDI composition (hereinafter referred to as elastomer-use XDI composition). The polyisocyanate component may contain other aromatic isocyanate, aliphatic isocyanate, and araliphatic isocyanate as necessary. The polyisocyanate component as the elastomer ingredient consists of, preferably, the elastomer-use XDI composition.

The DCI content in the elastomer-use XDI composition is 0.6 ppm or more, preferably 1.0 ppm or more, and 60 ppm or less, preferably 50 ppm or less, more preferably 30 ppm or less, particularly preferably 20 ppm or less.

When the DCI content in the elastomer-use XDI composition is the above-described lower limit or more, cloudiness and discoloration of the elastomer can be suppressed, and mechanical properties (elongation and strength) of the elastomer can be improved. When the DCI content in the elastomer-use XDI composition is the above-described upper limit or less, discoloration of the elastomer can be suppressed, and mechanical properties (elongation and strength) of the elastomer can be improved.

Examples of the high molecular weight polyol as the elastomer ingredient include the above-described polyesterpolyol (for example, polycaprolactone polyol, adipate polyesterpolyol (polyesterpolyol in which adipic acid is used as polybasic acid)), the above-described polycarbonatepolyol, and the above-described polytetramethylene ether glycol (for example, polytetramethylene ether glycol), and preferably, adipate polyesterpolyol is used.

Examples of the low molecular-weight polyol as the elastomer ingredient include ethylene glycol and 1,4-butyleneglycol, and preferably 1,4-butyleneglycol is used.

For the low molecular-weight polyamine as the elastomer ingredient, for example, the above-described low molecular-weight polyamine is used.

The elastomer can be produced by, for example, a known methods such as one shot process or prepolymer process.

In one shot process, for example, the polyisocyanate component, high molecular weight polyol, and low molecular-weight polyol and/or low molecular-weight polyamine are allowed to react all at once to produce the elastomer.

In prepolymer process, for example, first, the polyisocyanate component is allowed to react with the high molecular weight polyol to synthesize an isocyanate group-terminated prepolymer having an isocyanate group at its molecular terminal. Then, the produced isocyanate group-terminated prepolymer is allowed to react with the low molecular-weight polyol and/or low molecular-weight polyamine to produce the elastomer.

For the method for producing the elastomer, for example, bulk polymerization and solution polymerization can be used.

In the method for producing the elastomer, as necessary, for example, a known urethane-forming catalyst such as amines and organometallic compounds (for example, organic tin compound, preferably, dibutyltindichloride, etc.) can be added to the elastomer ingredient. Furthermore, to the elastomer, as necessary, a plasticizer, anti-blocking agent, heat-resistant stabilizer, light stabilizer, ultraviolet absorber, NOx yellowing inhibitor, antioxidant, release agent, pigment, dye, lubricant, nucleating agent, filler, and hydrolysis inhibitor can be blended at a suitable ratio.

In the above-described manner, the elastomer is produced. Such an elastomer has suppressed cloudiness, excellent resistance to discoloration, and mechanical properties (elongation and strength).

In the xenon irradiation test (240 hours), the elastomer has a color difference ($\Delta b$) of, for example, 1.0 or more, and for example, less than 3.9, preferably 3.5 or less, more preferably 3.0 or less. The elastomer color difference in the xenon irradiation test can be measured in accordance with the method described in Examples described later.

The elastomer has a tensile strength of, for example, 30.0 MPa or more, preferably 40.0 MPa or more, more preferably 55.0 MPa or more, and for example, 80.0 MPa or less. The elastomer tensile strength can be measured in accordance with the method described in Examples described later.

The elastomer has an elongation of, for example, 550% or more, preferably 600% or more, more preferably 650% or more, and for example, 1000% or less. The elastomer elongation can be measured in accordance with the method described in Examples described later.

(5-2) Foam

Examples of the foam include a soft foam and a hard foam. The soft foam has a hardness (25% CLD) of, for example, less than 40.6N/100 cm$^2$, and the hard foam has a hardness (25% CLD) of, for example, 40.6N/100 cm$^2$ or more. The hardness (25% CLD) can be measured in accordance with the method described in Examples described later.

The foam is produced by, for example, allowing the mixture of the polyisocyanate component, high molecular weight polyol (active hydrogen group-containing component), and blowing agent to react and foam. That is, the polyisocyanate component, high molecular weight polyol, and blowing agent are foam ingredients.

The polyisocyanate component as the foam ingredient contains, for example, the XDI composition (hereinafter referred to as foam-use XDI composition). The polyisocyanate component may contain other aromatic isocyanate, aliphatic isocyanate, and araliphatic isocyanate as necessary. The polyisocyanate component as the foam ingredient consists of, preferably, the foam-use XDI composition.

The DCI content in the foam-use XDI composition is 0.6 ppm or more, preferably 1.0 ppm or more, 60 ppm or less, preferably 50 ppm or less, more preferably 30 ppm or less, particularly preferably 20 ppm or less.

When the DCI content in the foam-use XDI composition is within the above-described range, discoloration of the foam can be suppressed, and mechanical properties (elongation and strength) of the foam can be improved.

For the high molecular weight polyol as the foam ingredient (hereinafter referred to as foam-use high molecular weight polyol), for example, the above-described polyetherpolyol is used.

For the blowing agent, for example, chemical blowing agent (for example, water) and physical blowing agent (for example, methylenechlorides, chlorofluorocarbons, hydroxychlorofluorocarbons, carbon dioxide, organic blowing agent, inorganic blowing agent, etc.) are used.

The foam can be produced by, for example, a known foaming method.

To be specific, the components (that is, high molecular weight polyol and blowing agent as essential components) other than the polyisocyanate component are blended in advance to prepare a resin premix. Then, the polyisocyanate component is blended with the resin premix to foam and mold to produce foam.

For the foam molding, for example, known methods such as a slab foaming process and a mold foaming process can be used. The foaming can also be performed by mechanical froth foam molding.

In the method for producing foam, as necessary, the above-described urethane-forming catalyst, cross-linking agent, and foam stabilizer can be added to the resin premix. Furthermore, to the foam, as necessary, a heat-resistant stabilizer (antioxidant), light stabilizer, multifunctional stabilizer can be blended at a suitable ratio.

In the above-described manner, foam is produced. Such foam has excellent resistance to discoloration, and mechanical properties (elongation and strength).

In the UV irradiation test (24 hours), the foam has a color difference ($\Delta$b) of, for example, 2.0 or more, and for example, 13.0 or less, preferably 12.5 or less, more preferably 12.0 or less. The foam color difference in the UV irradiation test can be measured in accordance with the method described in Examples described later.

The foam has a tensile strength of, for example, 30 kPa or more, preferably 50 kPa or more, and for example, 300 kPa or less. The foam tensile strength can be measured in accordance with the method described in Examples described later.

The foam has an elongation at break of, for example, 50% or more, preferably 80% or more, more preferably 90% or more, and for example, 500% or less. The foam elongation at break can be measured in accordance with the method described in Examples described later.

(5-3) One-Component Curable Sealant

The one-component curable sealant is a moisture curable sealant, and contained in the resin (polyurethane resin). The one-component curable sealant has an isocyanate group at its molecular terminal, and is cured by reaction with moisture in the air.

The one-component curable sealant is produced by reaction of, for example, the polyisocyanate component and high molecular weight polyol (active hydrogen group-containing component). That is, the polyisocyanate component and high molecular weight polyol are one component curable sealing materials.

The polyisocyanate component as the one component curable sealing material contains, for example, the XDI composition (hereinafter referred to as one component curable sealing-use XDI composition). The polyisocyanate component may contain other aromatic isocyanate, aliphatic isocyanate, and araliphatic isocyanate as necessary. The polyisocyanate component as the one component curable sealing material consists of, preferably, the sealing-use XDI composition.

The DCI content in the one component curable sealing-use XDI composition is 0.6 ppm or more, preferably 1.0 ppm or more, more preferably 3.0 ppm or more, particularly preferably 4.3 ppm or more, 60 ppm or less, preferably 50 ppm or less, more preferably 30 ppm or less, particularly preferably 20 ppm or less.

When the DCI content in the one component curable sealing-use XDI composition is within the above-described range, discoloration of the sealant can be suppressed, and mechanical properties (elongation and strength) of the sealant can be improved.

Examples of the high molecular weight polyol as the one component curable sealing material include the above-described polyetherpolyol, and preferably, polyoxy (C2 to C3)alkylenepolyol is used.

The one-component curable sealant can be produced by, for example, the above-described prepolymer process.

In the method for producing the one-component curable sealant, as necessary, the above-described urethane-forming catalyst can be added to the one component curable sealing material. Furthermore, to the one-component curable sealant, as necessary, a latent curing agent (for example, oxazolidine compound, etc.), filler (for example, silica, calcium carbonate, titanium oxide, etc.), antioxidant, and ultraviolet absorber can be blended at a suitable ratio.

In the above-described manner, the one-component curable sealant is produced. Such a one-component curable sealant has excellent resistance to discoloration, and mechanical properties (elongation and strength).

In the UV irradiation test (240 hours), the one-component curable sealant has a color difference ($\Delta$b) of, for example, 0.5 or more, and for example, 5.0 or less, preferably 3.0 or less, even more preferably 2.0 or less. The sealant color difference in the UV irradiation test can be measured in accordance with the method described in Examples described later.

The one-component curable sealant has a tensile strength of, for example, 5 MPa or more, preferably 10 MPa or more, even more preferably 12 MPa or more, and for example, 50 MPa or less, preferably 45 MPa or less. The sealant tensile strength can be measured in accordance with the method described in Examples described later.

The one-component curable sealant has an elongation at break of, for example, 300% or more, preferably 320% or more, even more preferably 330%, particularly preferably 400% or more, and for example, 1500% or less, preferably 1000% or less. The elongation at break of the sealant can be measured in accordance with the method described in Examples described later.

(5-4) Optical Material

Examples of the optical material include optical lenses including transparent lens, sunglass lens, polarizing lens, eyeglass lens, camera lens, pick-up lens, and contact lens; vehicle lighting panel, headlight lens, covers of headlight, and rear light; optical members for optical elements, optical disc, organic EL and LED; illumination for signboard; optical fiber, glass alternatives, intermediate film for laminated glass, windproof materials for aircrafts, large water tank walls, transparent roof materials, glazing materials, transparent members for daily use articles, protection glasses, hood, protective shields, automotive safety components, lighting components, and optical products such as smartphones and tablets.

Of these examples of the optical material, optical lens application is preferable.

The optical material is produced, particularly, the optical lens is produced by reaction of the polyisocyanate component with polythiol component. That is, the polyisocyanate component and polythiol component are optical material ingredients.

The polyisocyanate component for the ingredient of the optical material contains, for example, the XDI composition (hereinafter referred to as optical material-use XDI composition). The polyisocyanate component may contain other aromatic isocyanate, aliphatic isocyanate, and araliphatic isocyanate as necessary. The polyisocyanate component for the ingredient of the optical material preferably consists of the optical material-use XDI composition.

The DCI content in the optical material-use XDI composition is 0.6 ppm or more, and 60 ppm or less, preferably 50 ppm or less, more preferably 30 ppm or less, particularly preferably 20 ppm or less.

When the DCI content in the optical material-use XDI composition is the above-described lower limit or more, the optical material can be stably produced from the optical material-use XDI composition. When the DCI content in the optical material-use XDI composition is the above-described upper limit or less, discoloration of the optical material can be suppressed.

When the optical material-use XDI composition contains CBI, the optical material-use XDI composition has a CBI content of, for example, 0.2 ppm or more, preferably 1.0 ppm or more, more preferably 5.0 ppm or more, even more preferably 10 ppm or more, particularly preferably 50 ppm or more, especially preferably 100 ppm or more, and for example, 4000 ppm or less, preferably 3000 ppm or less, more preferably 1600 ppm or less, even more preferably 600 ppm or less, particularly preferably 500 ppm or less, especially preferably 400 ppm or less, most preferably 300 ppm or less.

When the CBI content in the optical material-use XDI composition is the above-described lower limit or more, the optical material can be stably produced from the optical material-use XDI composition. When the CBI content in the optical material-use XDI composition is the above-described upper limit or less, discoloration of the optical material can be reliably suppressed.

Particularly, when the DCI content in the optical material-use XDI composition is in the above-described range, and the CBI content in the optical material-use XDI composition is in the above-described range, the optical material can be produced from the optical material-use XDI composition even more stably, and discoloration of the optical material can be reliably suppressed.

Examples of the polythiol component as an ingredient for the optical material (hereinafter referred to as optical material-use polythiol component) include the above-described aliphatic polythiol containing a sulfur atom other than the mercapto group, and preferably 1,2-bis[(2-mercaptoethyl)thio]-3-mercaptopropane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, and a mixture thereof are used.

The optical material can be produced by, for example, the above-described one shot process.

In the optical material production, as necessary, the above-described urethane-forming catalyst, an internal release agent (for example, phosphoric acid ester release agent, alkyl phosphate release agent, fatty acid ester release agent, etc.), and ultraviolet absorber (for example, benzotriazole compound, formamidine compound, etc.) can be added to the polyisocyanate component. Furthermore, to the optical material, as necessary, a blueing agent, plasticizer, antifoaming agent, leveling agent, delusterant, fire retardant, thixotropic agent, tackifier, thickening agent, lubricant, antistatic agent, surfactant, reaction retardant, dehydrator, antioxidant, hydrolysis inhibitor, and weathering stabilizer can be blended at a suitable ratio.

In the above-described manner, the optical material is produced. Such an optical material has excellent resistance to discoloration.

The optical material has a yellow index value (Y.I. value) of, for example, 3.5 or more, and for example, 4.6 or less, preferably 4.3 or less. The yellow index value (Y.I. value) of the optical material can be measured in accordance with the method described in Examples described later.

6. Use of Two-Component Resin Material

The two-component resin material containing component A, i.e., an isocyanate component containing a XDI composition and/or XDI-modified composition, and component B, i.e., an active hydrogen group-containing component, can be suitably used for coating materials for paints and adhesives, a two-component curable sealing material, and a potting agent. Such a two-component resin material is used by blending component A (curing agent) and component B (main component), which are separately prepared, immediately before use. In the following, a method for producing a resin ingredient suitable for these applications is described.

As examples of use of such a two-component resin material, use as a coating material and a two-component curable sealing material is described in detail in the following.

(6-1) Coating Material

The coating material is a two-component curable resin material for forming a coating, and includes component A (curing agent) and component B (main component). The coating includes paints and adhesives.

When the coating material used as a paint, it is used for, for example, a paint for plastics, automobile exterior, automobile interior, electric and electronic materials, optical materials (lens, etc.), building materials, glass coating, woodwork, film coating, ink coating, artificial leather (coating agent), and cans (coating agent).

Examples of the plastic paint include a paint for housings (mobile phone, smartphone, personal computer, tablet, etc.), automobile parts (automobile interior and headlight, etc.), household appliances, robot materials, furniture, stationery, eyewear materials (lens, etc.), sports members (golf ball, etc.), bands (wrist watch bands, etc.), and optical lenses for electronic devices (surface coat agent).

Examples of the automobile exterior paint include a paint for new cars, automobile maintenance, and exterior parts (aluminum wheel, bumper, etc.).

Examples of the film coating paint include a paint for optical members (optical film, optical sheet, etc.), optical coating material, fiber, electric and electronic materials, food packaging, medical films, cosmetics packaging, film decoration, and release films.

When the coating material is used as adhesives, it is used for, for example, industrial adhesives, packaging adhesives (laminate adhesive), and hot melt adhesives.

Examples of the industrial adhesive include adhesives for electrical devices, liquid crystal displays (LCD), EL displays, EL lightings, display devices (electronic paper and plasma display, etc.), automobiles, household appliances, solar battery back sheets, and various batteries (lithium ion battery, etc.).

Examples of the packaging adhesives include adhesives for food packaging and packages for refillable household goods.

Such a coating material is provided as a product in the form of, for example, a solvent-based product, hydrophilic product, solventless product, and powder.

The component A contains, for example, as the polyisocyanate component, for example, a XDI-modified composition (hereinafter referred to as coating-use XDI-modified composition), and preferably, the XDI modified composition containing the above-described functional group of (a) (isocyanurate group), and/or, the XDI modified composition containing the above-described functional group of (d) (urethane group). The component A may contain other aromatic isocyanate, aliphatic isocyanate, and araliphatic isocyanate as necessary.

The DCI content in the coating-use XDI composition used for XDI-modified composition before modification is 0.6 ppm or more, preferably 2.0 ppm or more, and 60 ppm or less.

When the DCI content in the coating-use XDI composition is within the above-described range, discoloration of the coating can be suppressed.

When the coating material is used as paint, the DCI content in the coating-use XDI composition used for the XDI-modified composition before modification is 0.6 ppm or more, preferably 1.0 ppm or more, more preferably 4.0 ppm or more, and 60 ppm or less, preferably 50 ppm or less, more preferably 40 ppm or less, even more preferably 30 ppm or less, particularly preferably 20 ppm or less.

When the DCI content in the coating-use XDI composition used for paint is within the above-described range, discoloration of the cured coating can be suppressed, and adherence of the cured coating can be improved.

When the coating material is used as an adhesive, the DCI content in the XDI coating-use composition used for the XDI-modified composition before modification is 0.6 ppm or more, preferably 1.0 ppm or more, and 60 ppm or less, preferably 50 ppm or less, more preferably 40 ppm or less, even more preferably 20 ppm or less.

The DCI content in the coating-use XDI composition used for the adhesive is the above-described lower limit or more, discoloration of the cured adhesive can be suppressed, and appearance of an adherend to be adhered with the adhesive (for example, laminate film, etc.) can be improved.

When the DCI content in the coating-use XDI composition used for the adhesive is the above-described upper limit or less, discoloration of the cured adhesive can be suppressed, and adhesive strength of the adhesive can be improved.

The component B contains, for example, the above-described high molecular weight polyol as the active hydrogen group-containing component. Examples of the high molecular weight polyol as the coating material (hereinafter referred to as coating-use high molecular weight polyol) include the above-described acrylic polyol, the above-described polyesterpolyol, and the above-described fluorinepolyol.

To the component B, as necessary, a urethane-forming catalyst, hydrolysis inhibitor, antifoaming agent, surfactant, sliding agent, surface conditioner, antioxidant, weathering stabilizer, pigment, dye, filler, and resin powder can be blended at a suitable ratio.

The coating can be formed by, for example, blending the component A and component B, applying the mixture to a coating object by a known method, and then curing.

In the above-described manner, a coating is formed. Such a coating has excellent resistance to discoloration.

The coating has a color difference (Δb) in the damp heat endurance test (2000 hours) of, for example, 0.5 or more, and for example, 2.4 or less, preferably 2.2 or less, more preferably 2.0 or less, even more preferably 1.9 or less. The coating color difference in the damp heat endurance test can be measured in accordance with the method described in Examples described later.

(6-2) Two-Component Curable Sealing Material

The two-component curable sealing material is a two-component curable resin material for forming a two-component curable sealant, and contains the component A (curing agent) and component B (main component). The two-component curable sealing material is suitably used for sealing material for industrial, housing, and construction use.

The component A contains, for example, the XDI composition (hereinafter referred to as two-component curable sealing-use XDI composition) and/or XDI-modified composition (hereinafter referred to as two-component curable sealing-use XDI-modified composition), and preferably, the XDI modified composition containing the above-described functional group of (d) (urethane group). The component A may contain other aromatic isocyanate, aliphatic isocyanate, and araliphatic isocyanate as necessary. The component A consists of, preferably, the two-component curable sealing-use XDI composition and/or XDI-modified composition.

The DCI content in the two-component curable sealing-use XDI composition is, for example, 0.6 ppm or more, preferably 1.0 ppm or more, more preferably 3.0 ppm or more, particularly preferably 4.3 ppm or more, 60 ppm or less, preferably 50 ppm or less, more preferably 30 ppm or less.

When the DCI content in the two-component curable sealing-use XDI composition is within the above-described range, discoloration of the sealant can be suppressed, and mechanical properties (elongation at break and strength) of the sealant can be improved.

To the two-component curable sealing-use XDI composition, as necessary, the above-described urethane-forming catalyst, hydrolysis inhibitor, antifoaming agent, surfactant, sliding agent, surface conditioner, antioxidant, weathering stabilizer, pigment, dye, filler, resin powder, the above-described low molecular-weight polyol, and the above-described filler can be blended at a suitable ratio.

The component B contains, as the active hydrogen group-containing component, the isocyanate group-terminated prepolymer, i.e., a reaction product of the above-described high molecular weight polyol and polyisocyanate component. For the high molecular weight polyol for the two-component curable sealing material, for example, the above-described polyetherpolyol is used, and preferably, polyoxy (C2 to 3)alkylenepolyol is used.

Then, the two-component curable sealant is formed by, for example, blending the component A and component B, applying the mixture on a sealing object by a known method, and curing.

In the above-described manner, the two-component curable sealant is formed. Such a two-component curable sealant has excellent resistance to discoloration and mechanical properties (elongation at break and strength).

The two-component curable sealant has a color difference (Δb) in the UV irradiation test (240 hours) of, for example, 1.3 or more, and for example, 2.0 or less, preferably 1.8 or less. The color difference of the two-component curable sealant in the UV irradiation test can be measured in accordance with the method described in Examples described later.

The two-component curable sealant has an elongation at break of, for example, 1200% or more, preferably 1250% or more, more preferably 1300% or more, and for example, 1400% or less. The elongation at break of the two-component curable sealant can be measured in accordance with the method described in Examples described later.

7. Operations and Effects

As described above, the XDI composition contains XDI and DCI represented by the above-described Chemical Formula (1). The DCI content relative to a total mass of the XDI composition is 0.6 ppm or more and 60 ppm or less.

When the DCI content is within the above-described range, as is clear from Examples described later, irrespective of the CBI content, resistance to discoloration of the produced resin can be improved.

As a result, the resin of a reaction product of the polyisocyanate component containing the XDI composition and the active hydrogen group-containing component, and the resin material containing the polyisocyanate component (component A) and the active hydrogen group-containing component (component B) are suitably used in various industrial products, particularly as an elastomer, microcellular polyurethane, gel, polyurethane solution, foam, sealant, active energy ray (for example, electron beam, ultraviolet ray, etc.) curable resin, optical material, coating, pressure-sensitive adhesive, binder, microcapsule, ink, transfer foil, and potting material.

EXAMPLES

The present invention is further described in detail based on EXAMPLES below. However, the present invention is not limited to Examples. The specific numerical values of mixing ratio (content), physical property value, and parameter used in the description below can be replaced with the upper limit values (numerical values defined with "or less" or "below") or lower limit values (numerical values defined with "or more" or "more than") of the corresponding numerical values of mixing ratio (content), physical property value, and parameter described in "DESCRIPTION OF EMBODIMENTS" above. The "part(s)" and "%" are by mass, unless otherwise noted.

The measurements methods for the physical properties described below are shown in the following.

1. Measurement Method (Content of the Compound (DCI) Represented by Chemical Formula (1) Above)

First, DCI having a purity of 99 mol % synthesized in Preparation Example 1 described later was used as a standard substance, analyzed with gas chromatography with the conditions below, and a calibration curve was made from the area value of the obtained gas chromatogram (absolute calibration method).

Then, the XDI composition (or tar-removed mass) of Examples and Comparative Examples described later was analyzed with gas chromatography with the conditions below, and DCI amount by mole was obtained. The amount by mole was converted to mass, and the DCI content of the XDI composition of Examples and Comparative Examples described later was calculated. The DCI retention time was 16.6 minutes.

Device; HP-6890/5873 (manufactured by Hewlett-Packard Company)
Column; HP-50+, internal diameter 0.25 mm×length 30 m×film thickness 0.25 μm (manufactured by Hewlett-Packard Company)
Oven temperature; temperature increased at 10° C./min from 50° C. to 280° C., held for 6 min after reaching 280° C.
Split ratio; pulsed splitless method
Inlet temperature; 200° C.
Detector temperature; 280° C.
Carrier gas; He
Carrier gas flow rate; 1.0 ml/min (constant flow rate regulation)
Sample concentration: 1.0 mass % dichloromethane solution
Injection amount; 1.0 μL
Detection method; SIM (monitoring ion: m/z 180, 215)

(Xylylenediisocyanate (XDI) Content)

XDI having a purity of 99 mol % prepared in Preparation Example 2 described later was used as the standard substance, and analyzed with gas chromatography with the conditions below by internal standard method, and a calibration curve was made from the area value of the obtained gas chromatogram.

Then, the XDI composition (or tar-removed mass) of Examples and Comparative Examples described later was analyzed with gas chromatography with the conditions below, and the amount by mole of XDI was determined. This was converted to mass to calculate XDI content (purity) of the XDI composition of Examples and Comparative Examples described later. The internal standard substance had a retention time of 8.8 minutes, and the XDI retention time was 13.8 minutes.

Device; SHIMADZU 2014 (manufactured by Shimadzu Corporation)
Filler; DB-1 (film thickness) 1.5 μm,
Column; internal diameter 0.53 mm×length 60 m (manufactured by Shimadzu Corporation)

Oven temperature; temperature increased at 3° C./min from 130° C. to 220° C., temperature increased at 10° C./min after reaching 220° C. to 300° C.
Split ratio; pulsed splitless method
Inlet temperature; 280° C.
Detector temperature; 300° C.
Carrier gas; $N_2$ 158 kPa, $H_2$ 55 kPa, Air 45 kPa (constant pressure regulation)
Internal standard substance; 100 mg of 1,2,4,5-tetrachlorobenzene added to each sample
Solvent; chloroform
Sample concentration: 2.0 mass % chloroform solution
Injection amount; 2 μL
Detection method; FID
(Chloromethyl Benzyl Isocyanate (CBI) Content)

The XDI composition (or tar-removed mass) of Examples and Comparative Examples described later was analyzed with gas chromatography in the same manner as in the above-described XDI content measurement, except that CBI having a purity of 95 mol % (commercially available product) was used as the standard substance, and the CBI content of the XDI composition of Examples and Comparative Examples described later was calculated. The CBI retention time was 10.3 minutes.

(Cyanobenzylisocyanate (MCN) Content)

The XDI composition (or tar-removed mass) of Examples and Comparative Examples described later was analyzed with gas chromatography in the same manner as in the above-described XDI content measurement, except that MCN having a purity of 95 mol % (commercially available product) was used as the standard substance, and the MCN content of the XDI composition was calculated. The MCN retention time was 11.5 minutes.

(Calculation of Yellow Index Value (Y.I. Value) of Optical Material)

The optical material of Examples and Comparative Examples described later was formed into a circular flat plate plastic lens having a thickness of 9 mm and a diameter of 75 mm, and chromaticity coordinates x, y were measured using a chroma meter CT-210 manufactured by Minolta Co., Ltd. The Y.I. was calculated based on the values of x and y based on the formula (2) below.

It showed correlations that the smaller Y.I. value showed better hue in plastic lens, and the larger Y.I. value showed bad coloring.

$$\text{Y.I. value}=(234\times x+106\times y+106)/y \quad (2)$$

(Elastomer Cloudiness) The cloudiness of the elastomer of Examples and Comparative Examples described later was evaluated based on the criteria below visually.
3: transparent
2: slightly cloudy
1: cloudy
(Elastomer Weather Resistance Test)

The elastomer of Examples and Comparative Examples described later was cut into dice with a bale cutter, and ground with a crusher. The ground pellets were dried under nitrogen flow at 80° C. for 24 hours. The strand was extruded with a uniaxial extruder (type: SZW 40-28MG, manufactured by TECHNOVEL) in the cylinder temperature range of 150 to 245° C., and cut, thereby producing pellets of the elastomer of Examples and Comparative Examples described later. The pellets were dried further under nitrogen flow at 80° C. for 24 hours.

Then, using an injection molding device (type: NEX-140, manufactured by NISSEI PLASTIC INDUSTRIAL CO., LTD.), injection molding was performed under conditions of a screw number of revolution of 80 rpm, a barrel temperature of 150 to 235° C., a mold temperature of 20° C., an injection time of 10 seconds, injection speed of 60 mm/s, and cooling time of 45 seconds.

The produced sheet (thickness 2 mm) was aged under constant temperature and constant humidity conditions of 23° C. and relative humidity of 55% for 7 days, thereby producing an elastomer sheet of Examples and Comparative Examples described later.

Then, b value (b1, initial value) of the elastomer sheet was measured with a chroma meter (CR-200 manufactured by Minolta Co., Ltd.), and then xenon irradiation test was performed.

After an elapse of 240 hours, b value (b2) of the elastomer sheet was measured in the same manner as in the above. The color difference Δb (=|b2−b1|) of the elastomer sheet in the xenon irradiation test (240 hours) was calculated.

The xenon irradiation test was performed using a super xenon weather meter (SX75-AP manufactured by Suga Test Instruments Co., Ltd.) with conditions of a black panel temperature of 89° C., relative humidity of 50%, and xenon lamp irradiance of 100 W/m$^2$ (irradiation wavelength 300 to 400 nm).

(Elastomer Tensile Physical Properties)

The produced sheet was subjected to tensile test in accordance with the method described in JIS K-7311 Testing Methods for Thermoplastic Polyurethane Elastomers. The test piece (elastomer sheet) was stamped out with a JIS-No. 3 dumbbell, and the tensile strength (unit: MPa) and elongation (unit: %) were measured using a tensile tester (TYPE: AE-CT manufactured by Toyo Seiki Seisaku-sho, Ltd., full-automatic rubber tension tester) under the conditions of a gauge length of 20 mm and a tensile speed of 300 mm/min.

(Color Difference in UV Irradiation Test of the Foam)

A rectangular parallelepiped having a size of 30×40×10 mm was cut out from the foam of Examples and Comparative Examples described later to make a measurement sample, and then the b value (b1, initial value) of the measurement sample was measured using a color difference meter (Color Ace MODEL TC-1 manufactured by Tokyo Denshoku CO., LTD.).

Thereafter, the measurement sample was irradiated with ultraviolet ray with a short wavelength (wavelength 270 to 720 nm) using a QUV weathering tester equipped with a ultraviolet ray fluorescent lamp for 24 hours. The b value (b2) of the measurement sample after an elapse of 24 hours was measured in the same manner as described above. The color difference Δb (=|b2−b1|) of the foam in the UV irradiation test (24 hours) was calculated.

(Foam Apparent Density)

A rectangular parallelepiped having a size of 10×10×5 cm was cut out from the foam of Examples and Comparative Examples described later to make a measurement sample, and then the apparent density (unit:kg/m$^3$) of the measurement sample was measured in accordance with JIS K7222 (2005).

(Foam Hardness 25% CLD)

The hardness (unit:N/100 cm$^2$) of the foam of Examples and Comparative Examples described later was measured in accordance with the method D described in JIS K-6400-2 (2012).

(Foam Impact Resilience)

A rectangular parallelepiped having a size of 10×10×5 cm was cut out from the foam of Examples and Comparative Examples described later to make a measurement sample, and then the impact resilience (JIS:resilience by ball rebound)(unit:%) of the measurement sample was measured in accordance with JIS K6400-3(2004).

(Foam Tensile Physical Properties)

The tensile strength (unit:kPa) and the elongation at break (unit:%) of the foam of Examples and Comparative Examples described later were measured in accordance with JIS K6400-5(2004).

(Color Difference in UV Irradiation Test of Two-Component Curable Sealant)

A measurement sample was made from the two-component curable sealant of Examples and Comparative Examples described later, and then the b value (b1, initial value) of the measurement sample was measured using a color difference meter (Color Ace MODEL TC-1 manufactured by Tokyo Denshoku CO., LTD.).

Thereafter, the measurement sample was irradiated with ultraviolet ray with a short wavelength (wavelength 270 to 720 nm) using a QUV weathering tester equipped with a ultraviolet ray fluorescent lamp for 240 hours. The b value (b2) of the measurement sample after an elapse of 240 hours was measured in the same manner as described above. The color difference Δb (=|b2−b1|) of the two-component curable sealant in the UV irradiation test (240 hours) was calculated.

(Tensile Physical Properties of Two-Component Curable Sealant)

The two-component curable sealant of Examples and Comparative Examples described later was subjected to tensile test in accordance with the method described in JIS K-6301. The test piece (two-component curable sealant) was stamped out with a JIS-No. 2 dumbbell, and the tensile strength (unit:MPa) and elongation at break (unit:%) were measured using a tensile tester (TENSILON manufactured by A&D Company, Limited) under the conditions of a tensile speed of 500 mm/min.

(Color Difference (Discoloration and Stain) in Coating in Damp Heat Endurance Test)

The b value (b1, initial value) of the coating of Examples and Comparative Examples described later which was formed on the polyethylene terephthalate base (hereinafter referred to as sample) was measured using a color difference meter (SM-T JIS Z8722, manufactured by Suga Test Instruments Co., Ltd., under condition d, reflection conditions).

Then, the sample was held in a constant temperature and constant humidity container (THN 042PB manufactured by TOYO SEISAKUSHO) at 85° C. and a relative humidity of 85% for 2000 hours. The b value (b2) of the sample after an elapse of 2000 hours was measured in the same manner as described above. The color difference Δb (=|b2−b1|) of the coating in the damp heat test was calculated.

(Coating Adherence)

The sample after the above-described damp heat endurance test was subjected to adherence test by grid method (in accordance with JIS K5400-8.5).

(Appearance and Adhesive Strength of the Laminate Film in which Laminate Adhesive was Used)

A laminate adhesive (blending ratio of main component to curing agent (main component/curing agent)=10/6) of Examples and Comparative Examples described later was applied to a print surface of a white print polyethylene terephthalate film (thickness 12 μm) (white print ink; manufactured by SAKATA INX CORPORATION. Belle Color R white 115 1 component, polyethylene terephthalate film; manufactured by TOYOBO CO., LTD., ester film E5102) at a speed of 100 m/min and at 80° C. with a solventless laminator, and a dull surface of aluminum foil (AL, thickness 9 μm, manufactured by TOYO ALUMINIUM K.K., soft aluminum foil C) was laminated to the adhesive-applied surface of the white print polyethylene terephthalate film.

Then, the laminate adhesive of Examples and Comparative Examples described later was applied to the other surface of the aluminum foil (shiny side) at a speed of 100 m/min at 80° C. with a solventless laminator, and the applied surface was laminated to a corona treated surface of a cast polypropylene film (CPP, thickness 60 μm, manufactured by Mitsui Chemicals Tohcello.Inc. CP RXC-22).

The application of the adhesive was performed so that the application amount was about 3.0 g/m². Thereafter, the produced 3-layer laminate composite film (laminate film) was aged under conditions of 40° C. for 8 hours.

Then, the adhesive strength between the aluminum foil/cast polypropylene film was measured in accordance with JIS K 6854-3(1999) under the conditions of 24° C., 15 mm width, and a tensile speed of 300 mm/min.

The laminate film was aged at 40° C. for 4 days, thereby curing the laminate adhesive of Examples and Comparative Examples described later.

Then, appearance of the laminate was observed visually at the white print polyethylene terephthalate film side of the produced laminate film under criteria below.

Laminate Appearance;
GOOD: homogenous wetting and good appearance.
MEDIOCRE: homogenous wetting but slight presence of dots indicative of non-wetting.
BAD: presence of many dots indicative of non-wetting.

Then, the produced laminate film was used to make a bag with a size of 9 cm×13 cm, and the bag was charged with 150 g of a mixture of vinegar, salad oil, and ketchup with a volume ratio of 1/1/1. The bag was placed on a tray with a size of 210×520×105 mm, and subjected to hot water sterilization at 121° C. for 30 minutes under pressure of 0.20 MPa, then stored for 2 weeks at 50° C.

The adhesive strength between the aluminum foil/cast polypropylene film before and after the hot water sterilization, and after storage at 50° C. for 2 weeks was measured in accordance with JIS K 6854-3(1999) under the conditions of 24° C., a 15 mm width, and a tensile speed of 300 mm/min.

(Color Difference in UV Irradiation Test of Laminate Adhesive)

The laminate adhesive of Examples and Comparative Examples described later was applied to a polyethylene terephthalate sheet (Lumirror X 10S, manufactured by Toray Industries, Inc., 50 micron) so that the amount applied was 4.0 g/m² in the same manner as described above, and laminated to a polyethylene terephthalate sheet (Lumirror X 10S, manufactured by Toray Industries, Inc., 50 micron). It was aged at 40° C. for 4 days, thereby producing a laminate film.

The b value of the produced laminate film (b1, initial value) was measured with a colorimeter (SE-2000 manufactured by Nippon Denshoku Industries Co., Ltd., spectroscopic colorimeter) by transmittance method.

Then, the laminate film was irradiated continuously for 300 hours with a QUV device (Dewpanel Light Control Weather Meter FDP, manufactured by Suga Test Instruments Co., Ltd., continuous irradiation, 70° C., 10% RH, irradiance setting 28 W/m²), and after taken out from the device, the b value was measured with a colorimeter. The difference between the b value before irradiation (initial value) and the b value after irradiation was regarded as Δb value, and the degree of yellowing of the cured laminate adhesive was evaluated. The results are shown in Table 3.

(Color Difference in UV Irradiation Test of One-Component Curable Sealant)

The color difference Δb (=|b2−b1|) of the one-component curable sealant of Examples and Comparative Examples described later in UV irradiation test (240 hours) was calculated in the same manner as in the UV irradiation test of the above-described two-component curable sealant.

(Tensile Physical Properties of One-Component Curable Sealant)

The tensile strength (unit: MPa) and elongation at break (unit: %) of the one-component curable sealant of Examples and Comparative Examples described later was measured in accordance with the method described in JIS K-6301 in the same manner as in the above-described tensile test for the two-component curable sealant.

2. Preparation of Standard Substances

Preparation Example 1

DCI represented by the above-described Chemical Formula (1) was synthesized by the scheme shown in Chemical Formula (4) below.

[Chemical Formula 4]

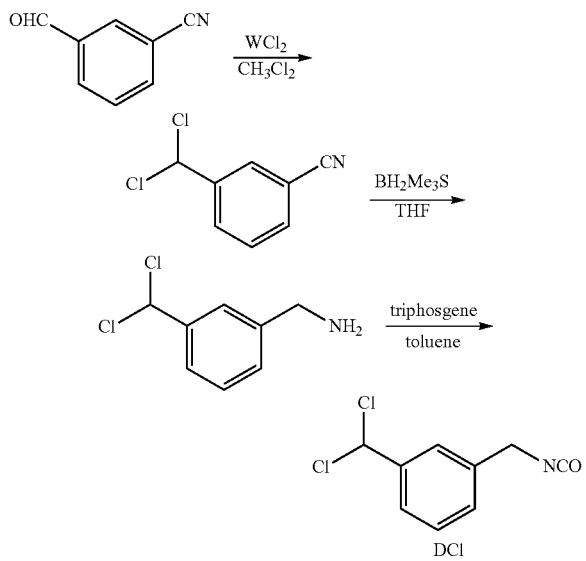

To a mixture solution of 250.4 mg (1.91 mmol) of 3-cyanobenzaldehyde and 15.0 ml of dichloromethane, 1.89 g (4.77 mmol) of tungsten chloride was added, and reaction was performed under dichloromethane reflux for 3 hours, and then cooled to room temperature. Then, the reaction solution was gradually dropped to a mixture liquid of 5 ml of aqueous solution of sodium hydrogen carbonate and 28 ml of 1N aqueous solution of sodium hydroxide while keeping the temperature of 10° C. or less.

After separating the dichloromethane layer, the water layer was subjected to extraction twice with 15 ml of dichloromethane. The dichloromethane layer produced through the separation was mixed with the dichloromethane layer produced through extraction, and the dichloromethane layer was washed with 20 ml of saturated sodium chloride solution, and then dried with magnesium sulfate.

After the drying, magnesium sulfate was filtered from the dichloromethane layer, and then dichloromethane was distilled off, thereby producing a concentrate. Then, 331.1 mg (1.78 mmol) of 3-(dichloromethyl)benzonitrile was produced from the concentrate by silica gel column chromatography. Then, the produced 3-(dichloromethyl)benzonitrile was analyzed with $^1$H-NMR (270 MHz, CDCl$_3$).

3-(dichloromethyl)benzonitrile: $^1$H-NMR (270 MHz, CDCl$_3$) δ7.89-7.81 (2H, m), 7.71-67 (1H, m), 7.58-7.53 (1H, m), 6.71(1H, s).

Then, to a mixture solution of 715.4 mg (3.85 mmol) of 3-(dichloromethyl)benzonitrile and 14.0 ml of tetrahydrofuran, 10.1 ml (19.2 mmol) of tetrahydrofuran solution of borane-dimethylsulfide complex was dropped at room temperature, and then the mixture was stirred for 23 hours to react.

After the reaction, 10 ml of water was dropped to the reaction solution while cooling the reaction solution with ice, then 2.5 ml (5.0 mmol) of 2M hydrochloric acid was added. Then, 20 ml of ethyl acetate was added to the reaction solution and the reaction solution was washed while stirring.

After separating and removing the ethyl acetate layer, 6 ml of 1M sodium hydroxide was added to the reaction solution, and the reaction solution was subjected to extraction with 15 ml of dichloromethane 4 times, and the produced dichloromethane layer was dried with magnesium sulfate.

After the drying, magnesium sulfate was filtered from dichloromethane layer, and then dichloromethane was distilled off, thereby producing 434.0 mg (2.28 mmol) of 3-(dichloromethyl)benzylamine. Then, the produced 3-(dichloromethyl)benzylamine was analyzed by $^1$H-NMR (270 MHz, CDCl$_3$).

3-(dichloromethyl)benzylamine: $^1$H-NMR (270 MHz, CDCl$_3$) δ7.79-7.33 (4H, m), 6.71(1H, s), 3.92 (2H, s).

Then, to a mixture solution of 263.4 mg (0.888 mmol) of triphosgene and 7.0 ml of toluene, a mixture solution of 337.4 mg (1.78 mmol) of 3-(dichloromethyl)benzylamine produced as described above and 7.0 ml of toluene was dropped, and reaction was performed at 120° C. for 3 hours.

After the reaction, cooling to room temperature was performed, and toluene was distilled off, thereby producing a concentrate. Then, 3 ml of chloroform was added to the concentrate to remove the insoluble matter by membrane filter, and then chloroform was distilled off, thereby producing 278.0 mg (1.29 mmol) of 3-(dichloromethyl)benzylisocyanate (DCI). Then, the produced 3-(dichloromethyl)benzylisocyanate (DCI) was analyzed with $^1$H-NMR (270 MHz, CDCl$_3$), $^{13}$C-NMR (100 MHz, CDCl$_3$), FT-IR, and MS.

3-(dichloromethyl)benzylisocyanate (DCI):
$^1$H-NMR (400 MHz, CDCl$_3$) δ7.64-7.33 (4H, m), 6.71 (1H, s), 4.56 (2H, s),
$^{13}$C-NMR (100 MHz, CDCl$_3$) δ46.0, 71.3, 123.3, 124.4, 125.7, 128.1, 129.3, 137.6, 141.0, FT-IR: 2256 cm$^{-1}$
MS: m/z=215 (M$^+$)

The produced 3-(dichloromethyl)benzylisocyanate (DCI) was analyzed by gas chromatography with the same conditions for the above-described DCI content measurement, except that the detection method was changed to FID.

Then, it was confirmed that in the obtained gas chromatogram, the ratio of the peak area (retention time 16.6 minutes) corresponding to DCI relative to a total peak area was 99 area % or more.

Based on the result, the synthesized 3-(dichloromethyl) benzylisocyanate (DCI) had a purity of 99 mol %, and regarded as DCI standard substance.

Preparation Example 2

The XDI composition produced in Example 1 described later was analyzed by, $^1$H-NMR (270 MHz, CDCl$_3$), $^{13}$C-

NMR (100 MHz, CDCl$_3$), FT-IR, and MS. The XDI composition was analyzed by gas chromatography under the conditions for the above-described measurement of the XDI content.

Then, it was confirmed that in the obtained gas chromatogram, the ratio of the peak area (retention time 13.8 minutes) corresponding to XDI relative to a total peak area was 99 area % or more.

Based on the result, the XDI content (purity) of the XDI composition was 99 mol %, and regarded as XDI standard substance.

3. Production of Xylylenediisocyanate Composition

Examples 1 to 7 and Example 10

A XDI composition was produced in the plant 1 shown in FIG. 1. To be specific, 600 parts by mass of orthodichlorobenzene (ODCB) was introduced into a mixing vessel 21 shown in FIG. 1. Then, the salt-forming temperature in the mixing vessel 21 was adjusted to 100° C., and the salt-forming pressure (gauge pressure) in the mixing vessel 21 was adjusted to 0.1 MPaG. Thereafter, 128 parts by mass of HCl gas was introduced into the mixing vessel 21 from the hydrogen chloride feed line 24, and a mixture solution (amine solution) of 160 parts by mass of m-XDA and 1240 parts by mass of ODCB was introduced into the mixing vessel 21 taking 2 hours from the amine feed line 22. In this manner, a slurry having a XDA hydrochloride concentration of 12.5 mass % was prepared.

Then, while HCl gas was introduced continuously into the mixing vessel 21 from the hydrogen chloride feed line 24 at a feeding speed of 64 parts by mass/hr, and an amine solution having a m-XDA concentration of 8 mass % was continuously introduced to the mixing vessel 21 from the amine feed line 22 at a feeding speed of 1000 parts by mass/hr, the slurry containing XDA hydrochloride was fed to the reaction tank 31A from the hydrochloride feed line 26.

Then, carbonyl chloride was continuously introduced from the carbonyl chloride feed line 30 at a feeding speed shown in Table 1 to the reaction tank 31A and the reaction tank 31B. Table 1 shows the reaction temperature and reaction pressure (gauge pressure) in the reaction tank 31A and reaction tank 31B, and the average residence time in the isocyanate-formation unit 3, and the amount of carbonyl chloride fed relative to 1 mol of XDA hydrochloride.

In this manner, XDA hydrochloride was allowed to react with carbonyl chloride to produce XDI, thereby preparing a reaction mass containing XDI. A portion of unreacted carbonyl chloride was condensed in the condenser 35A and condenser 35B, and returned to the reaction tank 31A and reaction tank 31B from the reflux line 34A and the reflux line 34B as a mixture liquid of liquefied carbonyl chloride and ODCB (reflux solution).

The unreacted carbonyl chloride not condensed by the condenser and by-produced HCl gas were fed to a carbonyl chloride collector, which is not shown, from a purge line 33A and a purge line 33B. Thereafter, in the carbonyl chloride collector, the liquefied carbonyl chloride and HCl gas were separated, and the liquefied carbonyl chloride was collected to a carbonyl chloride reservoir.

Then, the reaction mass was discharged from the reaction tank 31B to the reaction mass feed line 32B, and continuously fed to the de-gassing column 41. Thereafter, the reaction mass was subjected to de-gassing in a de-gassing column 41. Then, the de-gassed mass was discharged from the de-gassing column 41 to the de-gassing mass feed line 42, and continuously fed to the desolvation column 51. In this manner, 120 parts by mass of desolvated mass having a m-XDI concentration of 92 mass % was prepared.

Then, the desolvated mass was discharged from the desolvation column 51 by the desolvated mass feed line 52, and continuously fed to the tar-remover 61. Thereafter, the desolvated mass was subjected to tar-removal in the tar-remover 61, thereby preparing a tar-removed mass. Table 1 shows the ODCB content, XDI content, CBI content, and DCI content in the tar-removed mass.

Then, the tar-removed mass was continuously fed to the low-boiling removal tower 71 at a feeding speed of 100 parts by mass/hr by the tar-removed mass feed line 63. The low-boiling removal tower 71 was packed with a packed material corresponding to a theoretical plate number of 10 stages. Thereafter, the low-boiling component was removed from the tar-removed mass in the low-boiling removal tower 71, thereby preparing a low-boiling removed mass.

To be specific, the vapor mixture from the low-boiling removal tower 71 was condensed by the condenser 73, and a portion of the condensate including the low-boiling component was returned to the low-boiling removal tower 71 by the column-top reflux line 75. The other portion of the condensate was discharged by the low-boiling discharge line 74. The low-boiling removed mass was continuously fed to the rectifying column 81 by the low-boiling removed mass feed line 76.

The low-boiling removal conditions in the low-boiling removal tower are shown below.

Column-bottom temperature: 160 to 170° C.
Column-top temperature: 115 to 125° C.
Column-top pressure: 0.5 to 1.0 kPa
Column-top reflux amount: shown in Table 1.
Amount of low-boiling component distilled off from low-boiling discharge line: shown in Table 1.
Column-top reflux ratio: shown in Table 1.
Residence time: 0.3 to 3 hr Thereafter, the XDI composition was prepared as fraction from the low-boiling removed mass in the rectifying column 81. The rectifying column 81 was packed with a packed material corresponding to a theoretical plate number of 3 stages.

To be specific, the fraction (XDI composition) from the rectifying column 81 was condensed by the condenser 83, and a portion of the fraction (XDI composition) was returned to the rectifying column 81 by the column-top reflux line 85. The other portion of the fraction (XDI composition) was taken out from the XDI take-out line 84.

Rectification conditions in the rectifying column are shown below.

Column-bottom temperature: 150 to 160° C.
Column-top temperature: 140 to 150° C.
Column-top pressure: 0.5 to 0.8 kPa
Amount of the XDI composition distilled off from XDI distill off line: shown in Table 1.
Column-top reflux ratio: 1
Residence time: 1 to 10 hr In the above-described manner, the XDI composition was produced. Table 1 shows the XDI content, CBI content, DCI content, and hydrolysable chlorine content in the XDI composition.

Examples 8, 9 and Comparative Example 1

A XDI composition was produced in the same manner as in Example 1, except that the amount of ODCB, HCl gas, and m-XDA used was changed to ½ of Examples 1 to 7, the feeding speed of carbonyl chloride, reaction pressure (gauge pressure), average residence time, column-top reflux amount, amount of the low-boiling component distilled off, column-top reflux ratio, and amount of XDI composition distilled off were changed as shown in Table 1. Table 1 shows the XDI content, CBI content, DCI content, and hydrolysable chlorine content in the XDI composition.

Comparative Example 2

2000 g of the XDI composition produced in Example 2 was introduced into a four-neck round-bottom flask having an internal volume of 3 L. The four-neck flask was equipped with a 25 mmφ rectifying column packed with McMahon packing for 70 cm, a capillary tube for N₂ introduction, and a thermometer. To the column-top of the rectifying column, a magnetic switch, a condenser, and a 500 ml eggplant flask that receives the condensate from the condenser were attached.

Then, the column-top pressure of the rectifying column was adjusted to 0.2 to 0.3 kPa, the temperature in the four neck round-bottom flask was controlled to 150 to 165° C., and while refluxing by the magnetic switch with a column-top reflux ratio of 10, the distillate was taken out as the XDI composition to the 500 ml eggplant flask. Then, the 500 ml eggplant flask was changed for every 200 g of distillate, and together with distillate with distillation percentage (distillation percentage=distillate amount/amount of charged liquid×100) of 20 to 60%, 800 g of the XDI composition was fractionated. Table 1 shows the XDI, CBI, and DCI contents in the XDI composition.

Comparative Example 3

600 g of XDI composition was produced together with distillate of distillation percentage 50 to 80% in the same manner as in Comparative Example 2, except that the distillate was distilled off with a column-top reflux ratio of 20 until reaching distillation percentage of 50%, and thereafter, the distillate was distilled off with a column-top reflux ratio of 5. Table 1 shows the XDI, CBI, and DCI contents of the XDI composition.

TABLE 1

| | no. | | Ex. 1 | Ex. 2 | Ex. 3 | Ex. 4 | Ex. 5 | Ex. 6 | Ex. 7 |
|---|---|---|---|---|---|---|---|---|---|
| Iso-cyanate-formation step | Feeding speed (carbonyl chloride) | [Parts/hr] | 1450 | 1450 | 1750 | 1750 | 1750 | 1750 | 1750 |
| | Carbonyl chloride/XDA hydrochloride | [Molar ratio] | 12 | 12 | 15.2 | 15.2 | 15.2 | 15.2 | 15.2 |
| | Reaction temperature | [° C.] | 150 | 150 | 150 | 150 | 150 | 150 | 150 |
| | Reaction pressure | [MPaG] | 0.03 | 0.03 | 0.07 | 0.07 | 0.07 | 0.07 | 0.12 |
| | Average residence time | [hr] | 9 | 9 | 9 | 9 | 9 | 9 | 9 |
| Tar-removed mass | ODCB | [%] | 2.3 | 2.3 | 2.2 | 2.2 | 2.2 | 2.2 | 2.2 |
| | XDI | [%] | 97 | 97 | 97 | 97 | 97 | 97 | 97 |
| | CBI | [%] | 0.6 | 0.6 | 0.8 | 0.8 | 0.8 | 0.8 | 0.9 |
| | DCI | [ppm] | 2 | 2 | 5 | 5 | 5 | 5 | 20 |
| Low-boiling removal step | Column-top reflux amount | [Parts/hr] | 150 | 100 | 71 | 100 | 44 | 150 | 100 |
| | Distilled off amount (low-boiling) | | 3.1 | 3.1 | 3.3 | 3.4 | 3.1 | 3.4 | 3.5 |
| | Column-top reflux ratio | [—] | 48 | 32 | 22 | 29 | 14 | 44 | 29 |
| Rectification step | Distilled off amount (XDI composition) | [Parts/hr] | 94.0 | 93.7 | 93.8 | 93.8 | 93.8 | 93.7 | 94.0 |
| | Column-top reflux ratio | [—] | 1 | 1 | 1 | 1 | 1 | 1 | 1 |
| XDI composition | XDI | [%] | 99.9 | 99.9 | 99.8 | 99.9 | 99.7 | 99.9 | 99.9 |
| | CBI | [ppm] | 100 | 600 | 1600 | 600 | 3000 | 100 | 600 |
| | DCI | [ppm] | 0.7 | 1.2 | 4.2 | 4.4 | 4.5 | 4.5 | 18 |
| | MCN | [ppm] | <300 | <300 | <300 | <300 | <300 | <300 | <300 |
| | Hydrolysable chlorine | [ppm] | 70 | 160 | 380 | 210 | 640 | 100 | 210 |

| | no. | | Ex. 8 | Ex. 9 | Ex. 10 | Comp. Ex. 1 | Comp. Ex. 2 | Comp. Ex. 3 |
|---|---|---|---|---|---|---|---|---|
| Iso-cyanate-formation step | Feeding speed (carbonyl chloride) | [Parts/hr] | 1750 | 1750 | 1750 | 2350 | — | — |
| | Carbonyl chloride/XDA hydrochloride | [Molar ratio] | 30 | 30 | 15.2 | 40 | — | — |
| | Reaction temperature | [° C.] | 150 | 150 | 150 | 150 | — | — |
| | Reaction pressure | [MPaG] | 0.2 | 0.3 | 0.07 | 0.4 | — | — |
| | Average residence time | [hr] | 18 | 23 | 9 | 23 | — | — |
| Tar-removed mass | ODCB | [%] | 2.2 | 2.2 | 2.2 | 2.2 | — | — |
| | XDI | [%] | 96.5 | 96.3 | 97 | 96.2 | — | — |
| | CBI | [%] | 1.3 | 1.5 | 0.8 | 1.6 | — | — |
| | DCI | [ppm] | 45 | 60 | 5 | 70 | — | — |
| Low-boiling removal step | Column-top reflux amount | [Parts/hr] | 50 | 50 | 30 | 50 | — | — |
| | Distilled off amount (low-boiling) | | 1.9 | 1.9 | 3.0 | 2.0 | — | — |

TABLE 1-continued

|  |  |  |  |  |  |  |  |  |
|---|---|---|---|---|---|---|---|---|
| | Column-top reflux ratio | [—] | 26 | 26 | 10 | 25 | — | — |
| Rectification step | Distilled off amount (XDI composition) | [Parts/hr] | 46.9 | 46.8 | 93.8 | 46.7 | — | — |
| | Column-top reflux ratio | [—] | 1 | 1 | 1 | 1 | — | — |
| XDI composition | XDI | [%] | 99.8 | 99.8 | 99.6 | 99.8 | 99.9 | 99.9 |
| | CBI | [ppm] | 1100 | 1600 | 4100 | 1600 | 100 | 8 |
| | DCI | [ppm] | 40 | 58 | 4.5 | 65 | 0.5 | 0.5 |
| | MCN | [ppm] | <300 | <300 | <300 | <300 | <300 | <300 |
| | Hydrolysable chlorine | [ppm] | 300 | 380 | 880 | 380 | 60 | 40 |

4. Elastomer (TPU)

A four-neck flask equipped with a mixer, thermometer, reflux pipe, and nitrogen feed line was charged with 198 parts by mass of XDI composition (polyisocyanate component) of Examples 1, 2, 4, 6 to 9, and Comparative Examples 1 and 2, and 531.2 parts by mass of adipate polyesterpolyol (TAKELAC™ U-2024 manufactured by Mitsui Chemicals, Inc., active hydrogen group-containing component) having a number average molecular weight of 2000, and reaction was performed at 80° C. until the NCO group content reached 9.1 mass % in a nitrogen atmosphere, thereby producing an isocyanate group-terminated prepolymer.

Then, 3.9 parts by mass of a heat-resistant stabilizer (IRGANOX 245 manufactured by Ciba Specialty Chemicals), and 0.07 parts by mass of a solution in which a catalyst (Stanoct manufactured by API Corporation, stannous octoate) was diluted to diisononyladipate (DINA manufactured by J-PLUS Co., Ltd.) to be 4 mass % was added to the isocyanate group-terminated prepolymer, and the mixture was stirred using a three-one motor (HEIDON FBL 3000 manufactured by SHINTO Scientific Co., Ltd.) with 600 rpm for about 1 minute. Then, 131.9 parts by mass of 1,4-butanediol (manufactured by Wako Pure Chemical Industries, Ltd.) as the chain extender with its temperature pre-adjusted to 80° C. was added to the isocyanate group-terminated prepolymer. Furthermore, the mixture liquid of the isocyanate group-terminated prepolymer and the chain extender was sufficiently stirred for about 2 minutes until the entire mixture was homogenous.

Then, the mixture liquid was poured onto a stainless steel pad with its temperature pre-adjusted to 150° C., and reaction was performed at 150° C. for 1 hour, and then, at 100° C. for 23 hours, thereby producing an elastomer.

Thereafter, the elastomer was taken out from the pad, and aged for 7 days under conditions of constant temperature and constant humidity of the room temperature of 23° C. and the relative humidity of 55%.

(Evaluation of Elastomer)

The cloudiness, color difference in xenon irradiation test, and tensile physical properties (tensile strength and elongation) of the produced elastomer (TPU) were measured. The results are shown in Table 2. Correlation between the DCI content in the XDI composition (lower horizontal axis) and color difference in xenon irradiation test (vertical axis), and correlation between the CBI content in the XDI composition (upper horizontal axis) and color difference in xenon irradiation test (vertical axis) are shown in FIG. 2.

Figure 2:
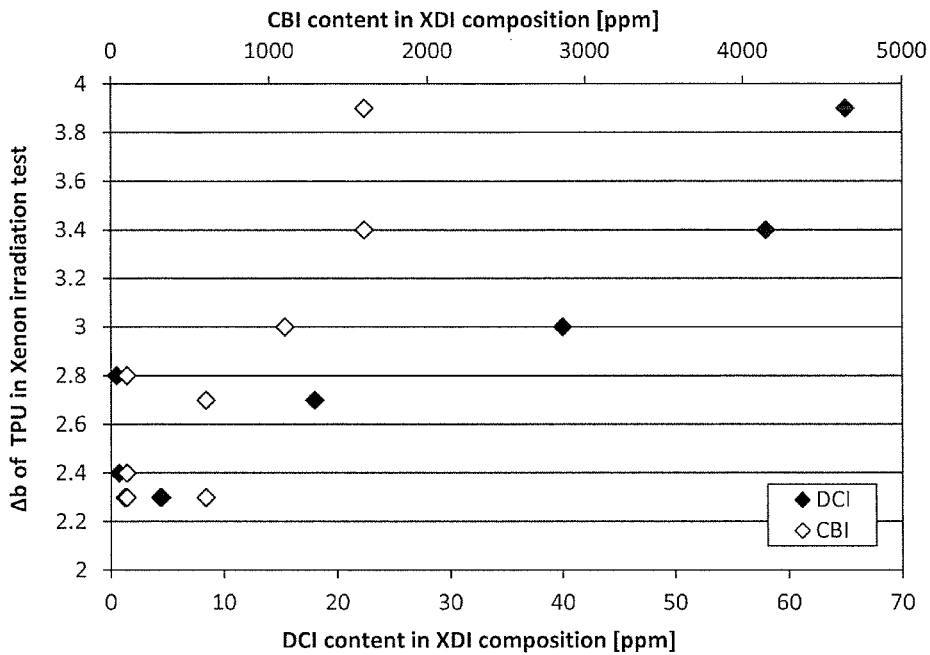
FIG. 2 is a graph illustrating correlation between the DCI content and the CBI content in the xylylenediisocyanate composition, and color difference in xenon irradiation test of the elastomer.

As shown in Table 2 and FIG. 2, when the DCI content relative to a total mass of the XDI composition was 0.6 ppm or more, elastomer (TPU) cloudiness was suppressed. When the DCI content relative to a total mass of the XDI composition was 60 ppm or less, irrespective of the CBI content, resistance to discoloration of the elastomer (TPU) improved.

This is clear from the comparison between Comparative Example 1 and Example 9. Comparative Example 1 and Example 9 both had a CBI content of 1600 ppm, but in Example 9 having a DCI content of 58 ppm, compared with Comparative Example 1 having a DCI content of 65 ppm, discoloration in xenon irradiation test (increase in Δb) was significantly suppressed.

When the DCI content relative to a total mass of the XDI composition is 0.6 ppm or more and 60 ppm or less, mechanical properties (elongation and strength) of the elastomer (TPU) improved. This is clear from the comparison between Comparative Example 2 and Example 1, and Comparative Example 1 and Example 9.

In Example 1 having a DCI content of 0.7 ppm, compared with Comparative Example 2 having a DCI content of 0.5 ppm, mechanical properties (elongation and strength) of the elastomer (TPU) significantly improved. In Example 9 having a DCI content of 58 ppm, compared with Comparative Example 1 having a DCI content of 65 ppm, mechanical properties (elongation and strength) of the elastomer (TPU) significantly improved.

5. Foam 60 parts by mass of polyetherpolyol having a number average molecular weight of 700 (ACTCOL G-250 manufactured by Mitsui Chemicals, Inc.), 40 parts by mass of polyetherpolyol having a number average molecular weight of 5000 (ACTCOL T-5000 manufactured by Mitsui Chemicals, Inc.), 5 parts by mass of triethanol amine, 3 parts by mass of water, 1 part by mass of amine catalyst (33LV manufactured by Momentive), 1 part by mass of dibutyltin dilaurate, 1 part by mass of foam stabilizer (BYK-9001 manufactured by BYK Japan KK), and 4 parts by mass of dipropylene glycol were stirred and mixed at a temperature of 23° C. and a relative humidity of 55% to be homogenous, thereby preparing a premix.

Thereafter, to the premix, 70.7 parts by mass of the XDI composition of Examples 1 to 10 and Comparative Examples 1 and 2 was added, and the mixture was stirred with a hand-mixer (number of revolution 5000 rpm) for 15 seconds, thereby producing a foam composition. Immediately thereafter, it was put into a wooden box and foamed. In this manner, foam was produced.

(Evaluation of Foam)

Color difference in UV irradiation test, tensile physical properties (tensile strength and elongation at break), apparent density, and hardness and impact resilience of the produced foam were measured. The results are shown in Table 2. Correlation between the DCI content in the XDI composition (lower horizontal axis) and color difference in UV irradiation test (vertical axis), and correlation between the CBI content of the XDI composition (upper horizontal axis) and color difference in UV irradiation test (vertical axis) are shown in FIG. 3.

Figure 3:
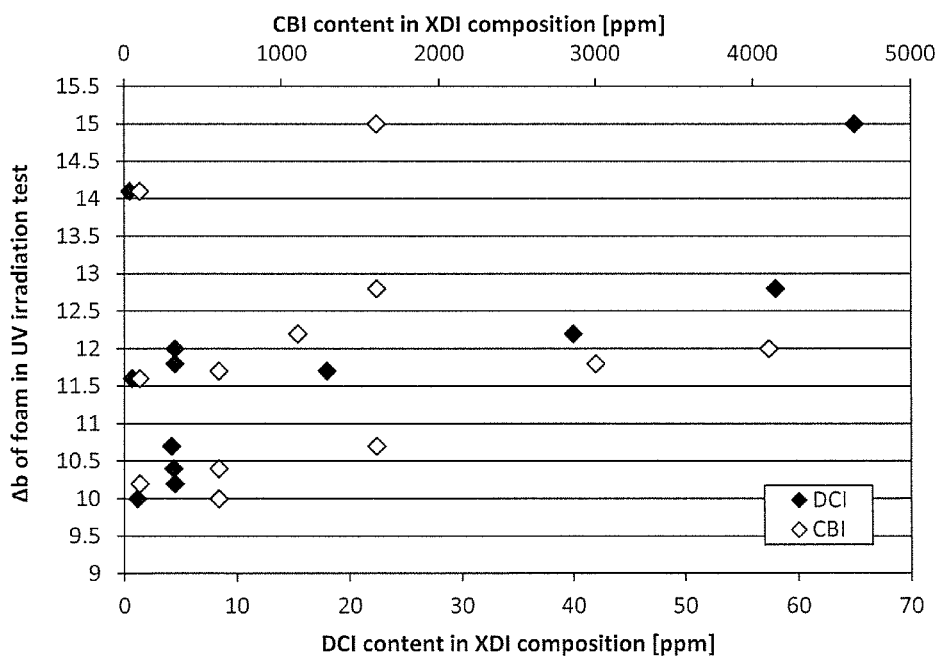
FIG. 3 is a graph illustrating correlation between the DCI content and the CBI content in the xylylenediisocyanate composition, and color difference in UV irradiation test of the foam.

As shown in Table 2 and FIG. 3, when the DCI content relative to a total mass of the XDI composition was 0.6 ppm or more and 60 ppm or less, irrespective of the CBI content, resistance to discoloration of the foam improved. This is clear from the comparison between Comparative Example 1 and Example 9. Comparative Example 1 and Example 9 both had a CBI content of 1600 ppm, but in Example 9 having a DCI content of 58 ppm, compared with Comparative Example 1 having a DCI content of 65 ppm, discoloration (increase in Δb) in UV irradiation test was significantly suppressed.

When the DCI content relative to a total mass of the XDI composition was 0.6 ppm or more and 60 ppm or less, mechanical properties (elongation and strength) of the foam improved. This is clear from the comparison between Comparative Example 2 and Example 1, and Comparative Example 1 and Example 9.

In Example 1 having a DCI content of 0.7 ppm, compared with Comparative Example 2 having a DCI content of 0.5 ppm, mechanical properties (elongation and strength) of the foam significantly improved. In Example 9 having a DCI content of 58 ppm, compared with Comparative Example 1 having a DCI content of 65 ppm, mechanical properties (elongation and strength) of the foam significantly improved.

When the CBI content relative to a total mass of the XDI composition was 3000 ppm or less, mechanical properties (elongation and strength) of the foam improved. This is clear from the comparison between Example 5 and Example 10.

In Example 5 having a CBI content of 3000 ppm, compared with Example 10 having a CBI content of 4100 ppm, mechanical properties (elongation and strength) of the foam improved.

6. Optical Material (Plastic Lens)

(Preparation of Plastic Lens A)

A flask was charged with 0.001 parts by mass of dibutyltindichloride, 0.07 parts by mass of an internal release agent (ZELEC UN manufactured by Stepan Company, acidic phosphate), 0.05 parts by mass of ultraviolet absorber (Viosorb 583 manufactured by SAKAI CHEMICAL INDUSTRY CO., LTD.), and 36.4 parts by mass of the XDI composition of Examples 1, 2, 4, 6 to 9, and Comparative Examples 1 and 3. Then, the mixture was stirred at 25° C. for 1 hour to be dissolved, thereby preparing a polyisocyanate component.

The XDI composition of Comparative Example 3 did not dissolve with dibutyltindichloride, internal release agent, and ultraviolet absorber well, and cloudiness and gellation occurred in the polyisocyanate component, and plastic lens was not produced.

Thereafter, 33.6 parts by mass of 1,2-bis[(2-mercaptoethyl)thio]-3-mercaptopropane (polythiol component) was introduced and mixed to the polyisocyanate component, thereby preparing a polymerizable composition.

The polymerizable composition was defoamed at 600 Pa for 1 hour, and then filtered with a 3 μm PTFE filter. Thereafter, the mixture was introduced into a mold composed of a glass mold and a tape. The mold was put into an oven, and the temperature was increased gradually from 10° C. to 120° C., performing polymerization for 18 hours. After the completion of polymerization, the mold was taken out from the oven, and it was released therefrom, thereby producing an optical material (plastic lens A).

(Plastic Lens B)

A flask was charged with 0.01 parts by mass of dibutyltindichloride, 0.1 parts by mass of internal release agent (ZELEC UN manufactured by Stepan Company, acidic phosphate), 0.05 parts by mass of ultraviolet absorber (Viosorb 583 manufactured by SAKAI CHEMICAL INDUSTRY CO., LTD.), and 50.7 parts by mass of the XDI composition of Examples 1, 2, 4, 6 to 9, and Comparative Examples 1 and 3. Then, the mixture was stirred at 25° C. for 1 hour to be dissolved, thereby preparing a polyisocyanate component.

The XDI composition of Comparative Example 3 did not dissolve with dibutyltindichloride, internal release agent, and ultraviolet absorber well, and cloudiness and gellation occurred in the polyisocyanate component, and plastic lens was not produced.

Thereafter, to the polyisocyanate component, 49.3 parts by mass of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane (polythiol component) was added and mixed, thereby preparing a polymerizable composition. The polymerizable composition was polymerized in the same manner as in the preparation of the plastic lens A, thereby preparing an optical material (plastic lens B).

(Evaluation of Optical Material)

Figure 4A:
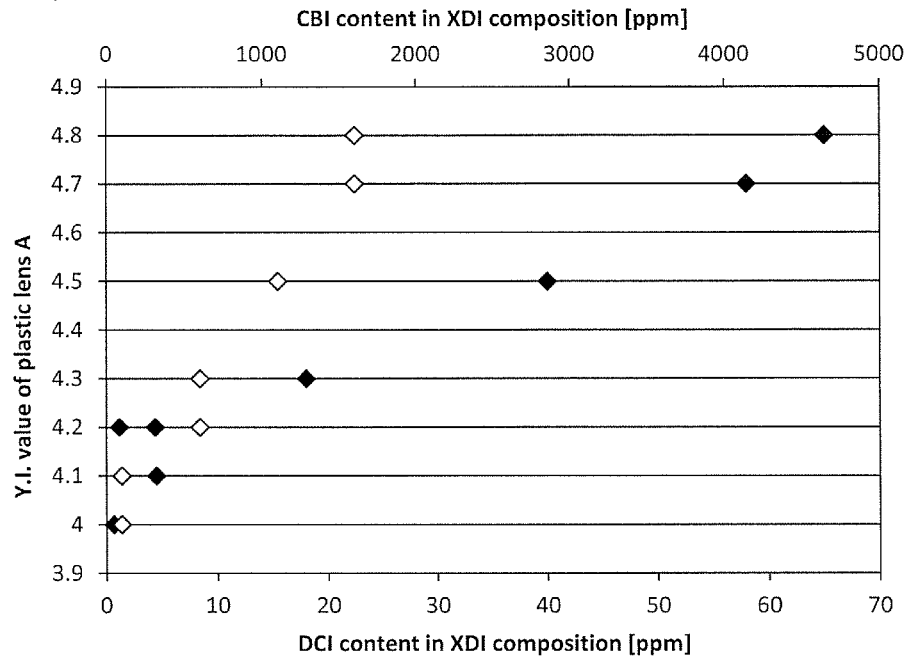
FIG. 4A is a graph illustrating correlation between the DCI content and the CBI content in the xylylenediisocyanate composition and the yellow index value of plastic lens A.

The Y.I. value of the produced plastic lenses A and B were measured. The results are shown in Table 2. Correlation between the DCI content in the XDI composition (lower horizontal axis) and the Y.I. value of the plastic lens A (vertical axis), and correlation between the CBI content of the XDI composition (upper horizontal axis) and the Y.I. value of the plastic lens A (vertical axis) are shown in FIG. 4A. Correlation between the DCI content in the XDI composition (lower horizontal axis) and the Y.I. value of the plastic lens B (vertical axis), and correlation between the CBI content of the XDI composition (upper horizontal axis) and the Y.I. value of the plastic lens B (vertical axis) are shown in FIG. 4B.

Figure 4B:
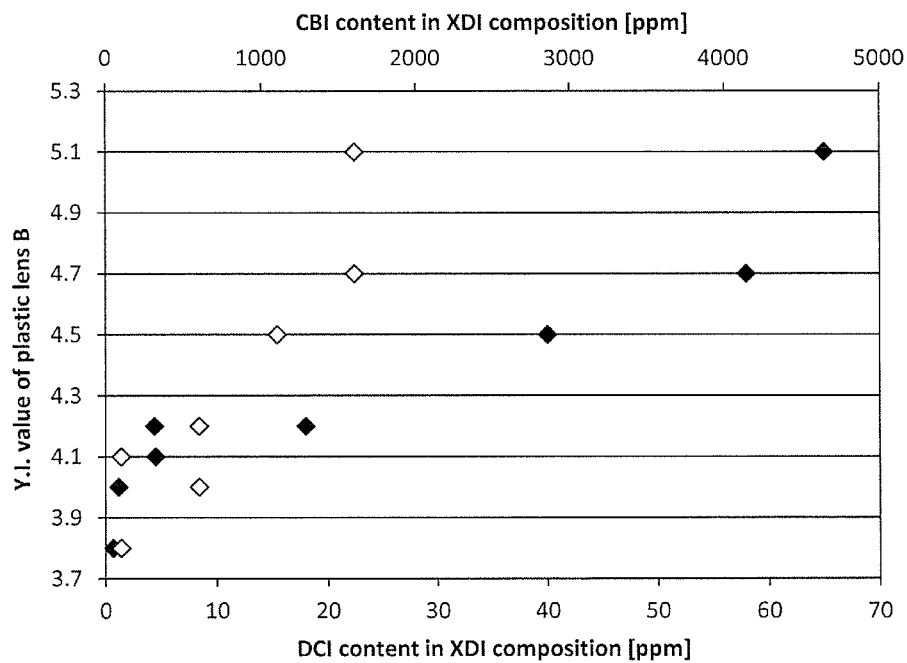
FIG. 4B is a graph illustrating correlation between the DCI content and the CBI content in the xylylenediisocyanate composition and the yellow index value of plastic lens B.

As is shown in Table 2, FIG. 4A, and FIG. 4B, when the DCI content relative to a total mass of the XDI composition was 0.6 ppm or more, cloudiness and gellation of the polyisocyanate component can be suppressed, and plastic lens can be stably produced. When the DCI content relative to a total mass of the XDI composition was 60 ppm or less, irrespective of the CBI content, resistance to discoloration of the plastic lens improved. This is clear from the comparison between Comparative Example 1 and Example 9. Comparative Example 1 and Example 9 both had a CBI content of 1600 ppm, but in Example 9 having a DCI content of 58 ppm, compared with Comparative Example 1 having a DCI content of 65 ppm, increase in the Y.I. value was significantly suppressed.

7. Two-Component Curable Sealant

A separable flask equipped with a mixer was charged with 170.0 parts by mass of the XDI composition (polyisocyanate component) of Examples 1 to 4, 7 to 9, and Comparative Examples 1 and 2, 553.3 parts by mass of polyoxypropylenediol having a number average molecular weight of 2000 (Diol-2000 manufactured by Mitsui Chemicals, Inc.), and 276.7 parts by mass of polyoxypropylenetriol having a number average molecular weight of 3000 (MN-3050 manufactured by Mitsui Chemicals, Inc.). The mixture was allowed to react in a nitrogen atmosphere at 80° C. for 5 hours. Thereafter, it was aged further at 25° C. for 24 hours, thereby producing component A (curing agent: isocyanate group-terminated prepolymer).

A planetary mixer was gradually charged with 20.1 parts by mass of 1,4-butanediol, 223.8 parts by mass of polyoxyethyleneoxypropylenediol having a number average molecular weight of 2000 (ED-56 manufactured by Mitsui Chemicals, Inc.), 223.8 parts by mass of polyoxyethyleneoxypropylenetriol having a number average molecular weight of 2000 (EP-550N manufactured by Mitsui Chemicals, Inc.), 1.0 part by mass of dibutyltin dilaurate, 35 parts by mass of diisononyladipate, 450 parts by mass of calcium carbonate, and 40 parts by mass of fumed silica (AEROSIL #200), and the mixture was stirred in a nitrogen atmosphere for 1 hour, thereby producing a component B (main component: active hydrogen group-containing component).

Then, 100 parts by mass of component A and 100 parts by mass of component B were stirred under the conditions of a temperature of 20° C. and a relative humidity of 50% for 3 minutes. The mixture liquid was applied homogenously to a steel plate, and then subjected to thermosetting at 100° C. for 1 hour, and aged under conditions of a temperature of 23° C. and a relative humidity of 50% for 7 days, thereby producing a two-component curable sealant.

(Evaluation of Two-Component Curable Sealant)

The color difference in UV irradiation test and tensile physical properties (tensile strength and elongation at break) of the produced two-component curable sealant were measured. The results are shown in Table 2. Correlation between the DCI content in the XDI composition (lower horizontal axis) and color difference in UV irradiation test (vertical axis), and correlation between the CBI content of the XDI composition (upper horizontal axis) and color difference in UV irradiation test (vertical axis) are shown in FIG. 5.

Figure 5:
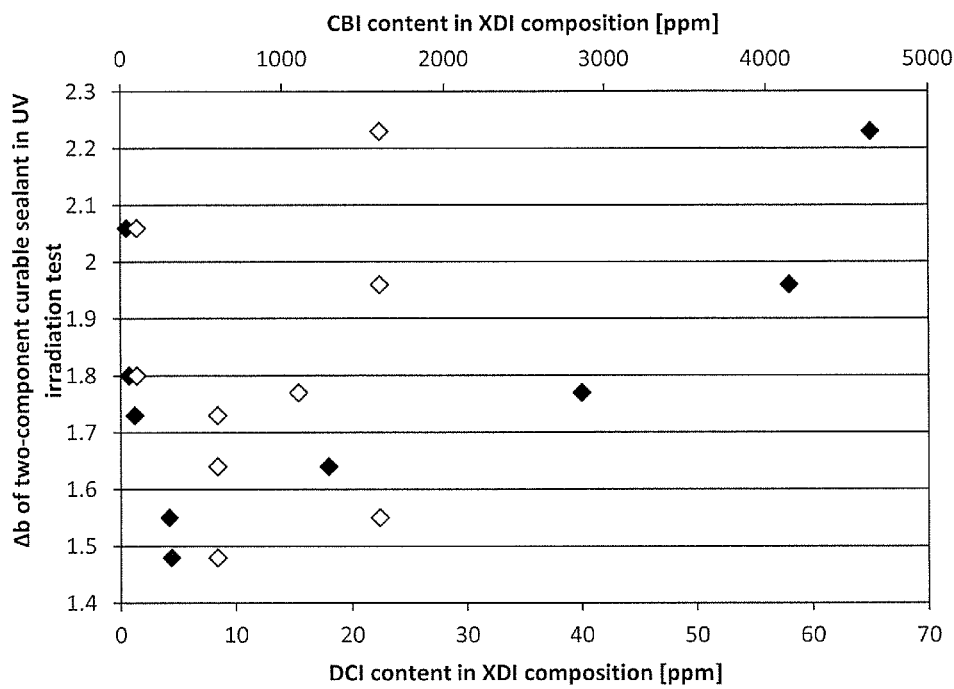
FIG. 5 is a graph illustrating correlation between the DCI content and the CBI content in the xylylenediisocyanate composition and the color difference in UV irradiation test of the two-component curable sealant.

As shown in Table 2 and FIG. 5, when the DCI content relative to a total mass of the XDI composition was 0.6 ppm or more and 60 ppm or less, irrespective of the CBI content, resistance to discoloration of the two-component curable sealant improved. This is clear from the comparison between Comparative Example 1 and Example 9. Comparative Example 1 and Example 9 both had a CBI content of 1600 ppm, but in Example 9 having a DCI content of 58 ppm, compared with Comparative Example 1 having a DCI content of 65 ppm, discoloration (increase in Δb) in UV irradiation test was significantly suppressed.

When the DCI content relative to a total mass of the XDI composition was 0.6 ppm or more and 60 ppm or less, mechanical properties (elongation and strength) of the two-component curable sealant improved. This is clear from the comparison between Comparative Example 2 and Example 1, and Comparative Example 1 and Example 9.

In Example 1 having a DCI content of 0.7 ppm, compared with Comparative Example 2 having a DCI content of 0.5 ppm, elongation of the two-component curable sealant significantly improved. In Example 9 having a DCI content of 58 ppm, compared with Comparative Example 1 having a DCI content of 65 ppm, elongation and strength of the two-component curable sealant significantly improved.

TABLE 2

| | no. | | Comp. Ex. 3 | Comp. Ex. 2 | Ex. 1 | Ex. 2 | Ex. 3 | Ex. 4 | Ex. 5 |
|---|---|---|---|---|---|---|---|---|---|
| XDI composition | XDI | [%] | 99.9 | 99.9 | 99.9 | 99.9 | 99.8 | 99.9 | 99.7 |
| | CBI | [ppm] | 8 | 100 | 100 | 600 | 1600 | 600 | 3000 |
| | DCI | [ppm] | 0.5 | 0.5 | 0.7 | 1.2 | 4.2 | 4.4 | 4.5 |
| | Hydrolysable chlorine | [ppm] | 40 | 60 | 70 | 160 | 380 | 210 | 640 |
| Lens | Lens A: Y.I-2 | | Gel | — | 4.0 | 4.2 | — | 4.2 | — |
| | Lens B: Y.I-2 | | Gel | — | 3.8 | 4.0 | — | 4.2 | — |
| TPU | Cloudiness | [—] | — | 2 | 3 | 3 | — | 3 | — |
| | Xenon irradiation test (240 h) | b1 | — | 0.62 | 0.60 | 0.60 | — | 0.61 | — |
| | | b2 | — | 3.4 | 3.0 | 2.9 | — | 2.9 | — |
| | | Δb | — | 2.8 | 2.4 | 2.3 | — | 2.3 | — |
| | 100% stress | [MPa] | — | 7.0 | 6.9 | 6.8 | — | 6.9 | — |
| | Tensile strength | [MPa] | — | 50.2 | 55.0 | 56.3 | — | 54.3 | — |
| | Elongation | [%] | — | 580 | 650 | 660 | — | 660 | — |
| Foam | UV irradiation test (24 h) | b1 | — | 1.36 | 1.28 | 1.20 | 1.25 | 1.21 | 1.38 |
| | | b2 | — | 15.5 | 12.9 | 11.2 | 11.9 | 11.6 | 13.2 |
| | | Δb | — | 14.1 | 11.6 | 10.0 | 10.7 | 10.4 | 11.8 |
| | Apparent density | [kg/m$^3$] | — | 42.5 | 41.8 | 41.1 | 41.3 | 41.2 | 42 |
| | 25% CLD | [N/100 cm$^2$] | — | 32.0 | 35.9 | 37.5 | 37.6 | 37.6 | 35.2 |
| | Impact resilience | [%] | — | 10.6 | 11.4 | 12.0 | 12.1 | 12.3 | 11.5 |
| | Tensile strength | [kPa] | — | 83 | 87 | 90 | 88 | 89 | 86 |
| | Elongation at break | [%] | — | 85 | 90 | 92 | 91 | 92 | 89 |
| Two-component curable sealant | UV irradiation test (240 h) | b1 | — | 1.02 | 0.98 | 0.96 | 0.98 | 0.92 | — |
| | | b2 | — | 3.08 | 2.78 | 2.69 | 2.53 | 2.4 | — |
| | | Δb | — | 2.06 | 1.8 | 1.73 | 1.55 | 1.48 | — |
| | Tensile strength | [MPa] | — | 21.2 | 21.0 | 21.3 | 21.2 | 22.0 | — |
| | Elongation at break | [%] | — | 1190 | 1250 | 1260 | 1320 | 1300 | — |

| | no. | | Ex. 6 | Ex. 7 | Ex. 8 | Ex. 9 | Ex. 10 | Comp. Ex. 1 |
|---|---|---|---|---|---|---|---|---|
| XDI composition | XDI | [%] | 99.9 | 99.9 | 99.8 | 99.8 | 99.6 | 99.8 |
| | CBI | [ppm] | 100 | 600 | 1100 | 1600 | 4100 | 1600 |
| | DCI | [ppm] | 4.5 | 18 | 40 | 58 | 4.5 | 65 |
| | Hydrolysable chlorine | [ppm] | 100 | 210 | 360 | 380 | 880 | 380 |

TABLE 2-continued

| | | | | | | | | |
|---|---|---|---|---|---|---|---|---|
| Lens | Lens A: Y.I-2 | | 4.1 | 4.3 | 4.5 | 4.7 | — | 4.8 |
| | Lens B: Y.I-2 | | 4.1 | 4.2 | 4.5 | 4.7 | — | 5.1 |
| TPU | Cloudiness | [—] | 3 | 3 | 3 | 3 | — | 3 |
| | Xenon irradiation test (240 h) | b1 | 0.58 | 0.60 | 0.65 | 0.72 | — | 0.80 |
| | | b2 | 2.9 | 3.3 | 3.6 | 4.1 | — | 4.7 |
| | | Δb | 2.3 | 2.7 | 3.0 | 3.4 | — | 3.9 |
| | 100% stress | [MPa] | 6.9 | 6.8 | 6.8 | 6.9 | — | 6.4 |
| | Tensile strength | [MPa] | 54.8 | 54.1 | 53.2 | 53.0 | — | 49.2 |
| | Elongation | [%] | 660 | 660 | 650 | 640 | — | 540 |
| Foam | UV irradiation test (24 h) | b1 | 1.20 | 1.29 | 1.33 | 1.38 | 1.41 | 1.48 |
| | | b2 | 11.4 | 13 | 13.5 | 14.2 | 13.4 | 16.5 |
| | | Δb | 10.2 | 11.7 | 12.2 | 12.8 | 12.0 | 15.0 |
| | Apparent density | [kg/m$^3$] | 41.3 | 41.8 | 42.0 | 42.0 | 42.0 | 42.8 |
| | 25% CLD | [N/100 cm$^2$] | 37.4 | 37.5 | 37.6 | 37.8 | 34.7 | 32.1 |
| | Impact resilience | [%] | 12.2 | 12.3 | 12.0 | 12.0 | 10.8 | 10.1 |
| | Tensile strength | [kPa] | 90 | 89 | 88 | 88 | 79 | 81 |
| | Elongation at break | [%] | 93 | 91 | 90 | 90 | 74 | 78 |
| Two-component curable sealant | UV irradiation test (240 h) | b1 | — | 0.98 | 1.05 | 1.09 | — | 1.15 |
| | | b2 | — | 2.62 | 2.82 | 3.05 | — | 3.38 |
| | | Δb | — | 1.64 | 1.77 | 1.96 | — | 2.23 |
| | Tensile strength | [MPa] | — | 21.3 | 21.0 | 20.2 | — | 19.2 |
| | Elongation at break | [%] | — | 1280 | 1230 | 1200 | — | 1120 |

8. Coating Material (Component A 1: TMP Adduct of XDI)

463.3 parts by mass of the XDI composition of Examples 1, 3, 4, 7 to 9, and Comparative Examples 1, 2, and 36.7 parts by mass of trimethylolpropane were mixed, and the mixture was allowed to react in a nitrogen atmosphere at 70° C. for 6 hours. The unreacted XDI was distilled off from the reaction solution using a thin film distillation device, thereby producing a XDI-modified composition. The XDI-modified composition contained a urethane group, a reaction product of XDI and trimethylolpropane.

Ethyl acetate was added to the XDI-modified composition so that the solid content was 75 mass %, thereby producing a polyisocyanate component (component A 1). The polyisocyanate component had a NCO group content of 11.8 mass %.

(Component A 2: Isocyanurate-Modified XDI)

2 parts by mass of 1,3-butanediol was added to 100 parts by mass of the XDI composition of Examples 1, 3, 4, 7 to 9 and Comparative Examples 1, 2, and the temperature was increased to 75° C. in a nitrogen atmosphere, thereby performing urethane-forming reaction for 2 hours. The equivalent ratio (NCO/OH) of the isocyanate group of XDI relative to the hydroxy group of 1,3-butanediol was 24. Then, at the same temperature, 0.1 phr (solid content-based 0.037 phr) of tetrabutylammonium hydroxide solution (37% methanol solution) as the isocyanurate-forming catalyst was blended, and the isocyanurate-forming reaction was terminated after 4 hours from the start of the reaction. The produced reaction solution was passed through a thin film distillation device (temperature 150° C., degree of vacuum 50 Pa) to remove the unreacted XDI (distillation yield 60 mass %), thereby producing a XDI modified composition. The XDI-modified composition contained an isocyanurate group, trimer of XDI. Ethyl acetate was added to the XDI-modified composition so that the solid content was 75 mass %, thereby producing a polyisocyanate component (component A2).

(Component B)

40 parts by mass of fluorinepolyol (ZEFFLE™ GK-570 manufactured by DAIKIN INDUSTRIES, LTD., hydroxyl number (solid content): 64 mgKOH/g, solvent: butyl acetate), 52.5 parts by mass of titanium oxide (CR93 manufactured by ISHIHARA SANGYO KAISHA, LTD.), 33.8 parts by mass of butyl acetate, and 110 parts by mass of 2 mm diameter glass beads were mixed with a paint shaker for 2 hours. Thereafter, the glass beads were removed from the mixture liquid by filtration. Then, a solvent was added so that the solid content concentration was 58 mass %, thereby producing an active hydrogen group-containing component (component B). The active hydrogen group-containing component had a titanium oxide content of 45 mass %.

(Evaluation of Coating)

The produced polyisocyanate component (component A 1 and component A 2) and the active hydrogen group-containing component (component B) were mixed so that the equivalent ratio of the isocyanate group relative to the hydroxyl group (NCO/OH) was 1.0, thereby preparing a mixture liquid. Then, butyl acetate was added to the mixture liquid so that the NV value (mass of coating) was 60%. Thereafter, the mixture liquid was applied to the surface of a polyethylene terephthalate (hereinafter referred to as PET) base, and subjected to thermosetting at 120° C. for 2 minutes. Then, the PET base to which the mixture liquid was applied was aged at 60° C. for 2 days. In this manner, a coating having a thickness of about 15 μm was formed on the PET base.

The weather resistance (the color difference Δb (=|b2−b1|) of the coating in the damp heat test) and adherence (grid test) of the coating were measured. The results are shown in Table 3. Correlation between the DCI content in the XDI composition (lower horizontal axis) and color difference in the damp heat test (vertical axis), and correlation between the CBI content of the XDI composition (upper horizontal axis) and color difference in the damp heat test (vertical axis) are shown in FIG. 6 and FIG. 7.

Figure 6:
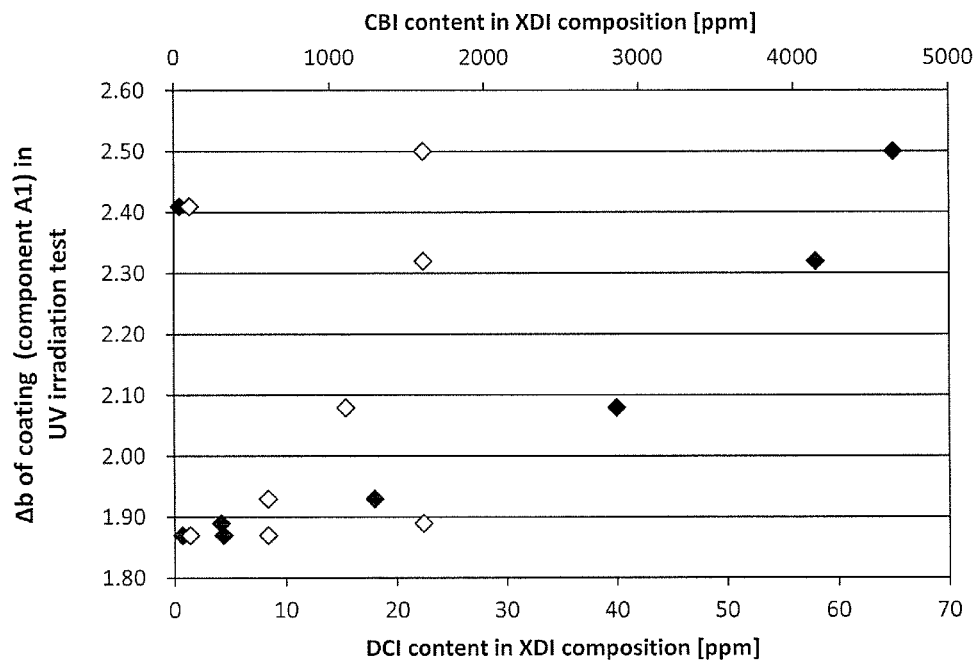
FIG. 6 is a graph illustrating correlation between the DCI content and the CBI content in the xylylenediisocyanate composition and the color difference in UV irradiation test of the coating (component A 1).
Figure 7:
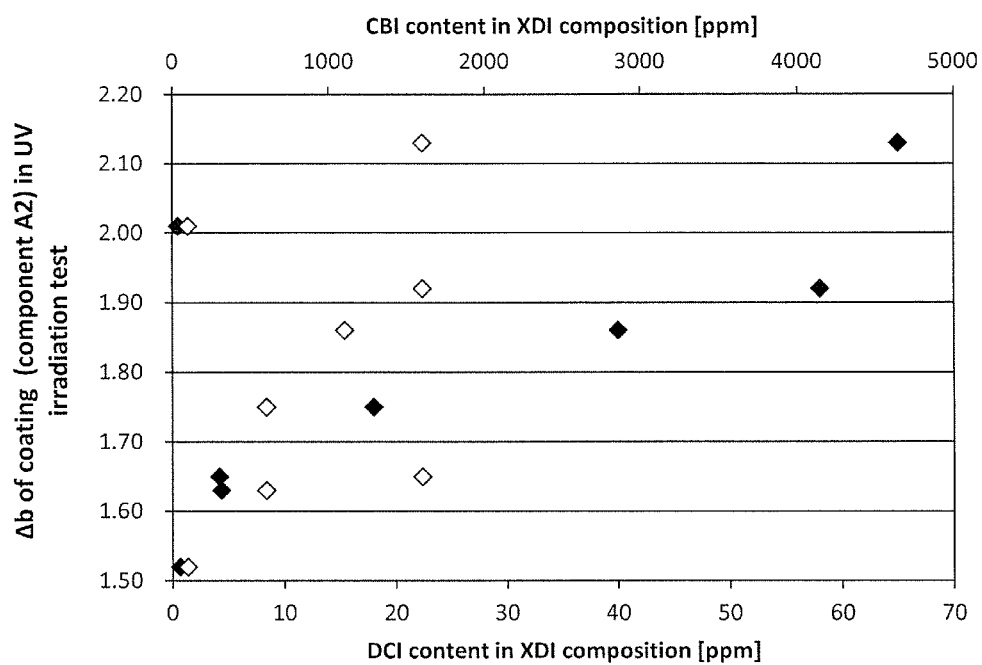
FIG. 7 is a graph illustrating correlation between the DCI content and the CBI content in the xylylenediisocyanate composition and the color difference in UV irradiation test of the coating (component A 2).

As shown in Table 3, FIG. 6, and FIG. 7, when the DCI content relative to a total mass of the XDI composition was 0.6 ppm or more and 60 ppm or less, irrespective of the CBI content, resistance to discoloration of the coating improved. This is clear from the comparison between Comparative Example 1 and Example 3. Comparative Example 1 and Example 3 both had a CBI content of 1600 ppm, but in Example 3 having a DCI content of 4.2 ppm, compared with Comparative Example 1 having a DCI content of 65 ppm, discoloration (increase in Δb) in the damp heat test was significantly suppressed.

When the DCI content relative to a total mass of the XDI composition was 0.6 ppm or more and 60 ppm or less, coating adherence improved. This is clear from the comparison between Comparative Example 2 and Example 1, and Comparative Example 1 and Example 9.

In Example 1 having a DCI content of 0.7 ppm, compared with Comparative Example 2 having a DCI content of 0.5 ppm, coating adherence significantly improved. In Example 9 having a DCI content of 58 ppm, compared with Comparative Example 1 having a DCI content of 65 ppm, coating adherence significantly improved.

9. Laminate Adhesive

A reactor equipped with a thermometer, mixer, nitrogen inlet tube, and condenser tube was charged with 100 parts by mass of the XDI composition of Examples 1 to 4, 7 to 9, and Comparative Examples 1 and 2, 0.025 parts by mass of 2,6-di(tert-butyl)-4-methylphenol (also called: dibutylhydroxytoluene, BHT, hindered phenol antioxidant), and 0.05 parts by mass of tetraphenyl.dipropylene glycol.diphosphite (JPP-100(trade name, manufactured by Johoku Chemical Co. Ltd.) organic phosphite, promoter) in a nitrogen atmosphere, and thereafter, 1.96 parts by mass of 1,3-butanediol was added to the charged liquid. The temperature of the charged liquid was increased to 75° C., thereby performing urethane-forming reaction. The equivalent ratio (NCO/OH) of the isocyanate group of m-xylylenediisocyanate relative to the hydroxy group of 1,3-butanediol was 24.

Then, reaction was performed at the same temperature for 120 minutes, and thereafter the temperature was decreased to 60° C. Then, as the isocyanurate-forming catalyst, 0.04 parts by mass (solid content-based 0.015 parts by mass) of tetrabutylammonium hydroxide (TBAOH) solution (37% methanol solution) was blended, thereby causing isocyanurate-forming reaction. The isocyanurate-forming reaction was terminated after 390 minutes from the reaction start. The highest temperature reached during the reaction was 71° C.

Then, the produced reaction mixture liquid was passed through a thin film distillation device (temperature 150° C., degree of vacuum 50 Pa) to remove the unreacted xylylenediisocyanate. The distillation yield was 60.0 mass %.

The alcohol modification percentage in this reaction was, in the reaction mixture liquid (before distillation), 1.96 mass %, and in isocyanurate derivative (after distillation), 3.27 mass %, and the isocyanate group conversion rate was 34.2 mass %, the urethane conversion rate was 5.3 mass %, and the isocyanurate conversion rate was 28.9 mass %.

The produced reaction mixture liquid was diluted with ethyl acetate so that the solid content was 75%, thereby producing a curing agent for laminate adhesive (component A).

588.1 parts by mass of isophthalic acid, 752.24 parts by mass of 1,3-butanediol, and 440.22 parts by mass of neopentyl glycol were subjected to esterification reaction under nitrogen flow at 180 to 220° C., and after distilling a predetermined amount of water, 258.66 parts by mass of adipic acid, 357.98 parts by mass of sebacic acid, and 0.08 parts by mass of titaniumtetrabutoxide were added, and esterification reaction was performed at 180 to 220° C., thereby producing polyesterpolyol having a number average molecular weight of about 500.

Then, 750 parts by mass of polyesterpolyol and 57.6 parts by mass of trimellitic anhydride were allowed to react under nitrogen flow at 120 to 150° C. for 3 hours, and after cooling to 60° C., 171.4 parts by mass of ACTCOLT-700 (polypropylenepolyol, manufactured by Mitsui Chemicals SKC polyurethane), 1.0 part by mass of phosphoric acid and 20.0 parts by mass of epoxysilane were added. The mixture was sufficiently mixed, thereby producing a main component (component B) of resin having a solid content of 100%.

Then, the main component and the curing agent were blended at a mass ratio of 10/6, thereby producing a laminate adhesive.

(Evaluation of Laminate Adhesive)

Appearance, adhesive strength, and color difference in UV irradiation test of the laminate film in which the produced laminate adhesive was used was measured. The results are shown in Table 3. Correlation between the DCI content in the XDI composition (lower horizontal axis) and color difference in UV irradiation test (vertical axis), and correlation between the CBI content of the XDI composition (upper horizontal axis) and color difference in UV irradiation test (vertical axis) are shown in FIG. 8.

Figure 8:
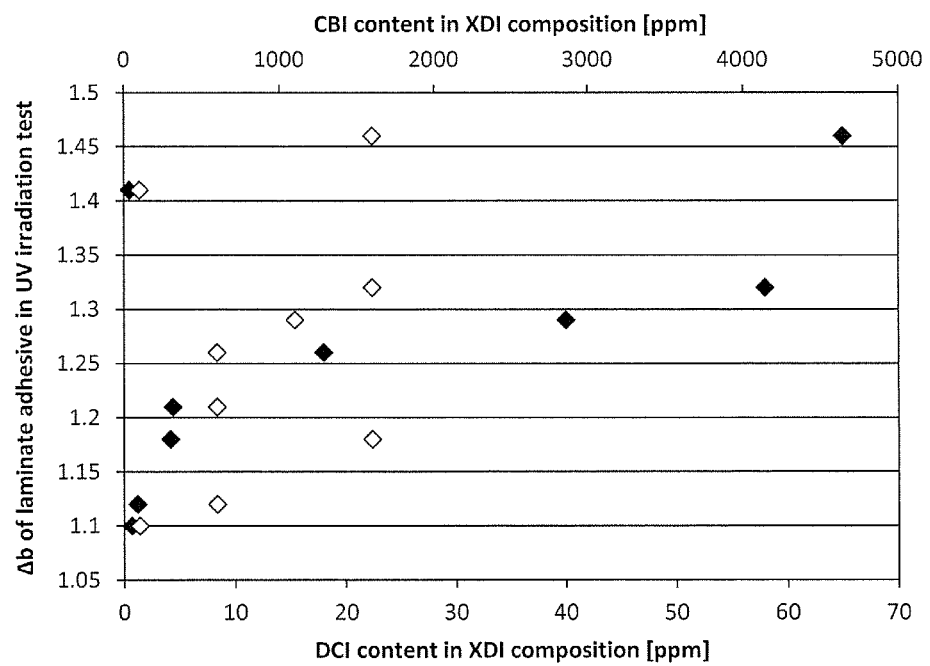
FIG. 8 is a graph illustrating correlation between the DCI content and the CBI content in the xylylenediisocyanate composition and the color difference in UV irradiation test of the laminate adhesive.

As shown in Table 3 and FIG. 8, when the DCI content relative to a total mass of the XDI composition is 0.6 ppm or more and 60 ppm or less, irrespective of the CBI content, resistance to discoloration of the laminate adhesive improved. This is clear from the comparison between Comparative Example 2 and Example 1, and Comparative Example 1 and Example 9.

Comparative Example 2 and Example 1 both had a CBI content of 100 ppm, but in Example 1 having a DCI content of 0.7 ppm, compared with Comparative Example 2 having a DCI content of 0.5 ppm, discoloration (increase in Δb) in UV irradiation test was significantly suppressed. Comparative Example 1 and Example 9 both had a CBI content of 1600 ppm, but in Example 9 having a DCI content of 58 ppm, compared with Comparative Example 1 having a DCI content of 65 ppm, discoloration (increase in Δb) in UV irradiation test was significantly suppressed.

When the DCI content relative to a total mass of the XDI composition was 0.6 ppm or more and 60 ppm or less, appearance of the laminate film improved. This is clear from the comparison between Comparative Example 2 and Example 1, and Comparative Example 1 and Example 9.

In Example 1 having a DCI content of 0.7 ppm, compared with Comparative Example 2 having a DCI content of 0.5 ppm, appearance of the laminate film significantly improved. In Example 9 having a DCI content of 58 ppm, compared with Comparative Example 1 having a DCI content of 65 ppm, appearance of the laminate film significantly improved.

10. One-Component Curable Sealant

A separable flask equipped with a mixer was charged with, in a nitrogen atmosphere, 91.67 parts by mass of the XDI composition (polyisocyanate component) of Examples 1 to 4, 7 to 9, and Comparative Examples 1, 2, and 229.78 parts by mass of polyoxypropylenediol subjected to reduced pressure dehydration treatment in advance and having a number average molecular weight of 3000 (D-3000 manufactured by Mitsui Chemicals SKC polyurethane) and 199.57 parts by mass of polyoxypropylenetriol having a number average molecular weight of 5000 (T-5000 manufactured by Mitsui Chemicals SKC polyurethane). The mixture was allowed to react in a nitrogen atmosphere at 90° C. for 6 hours. Thereafter, 83.90 parts by mass of polyesterpolyol (TAKELAC™ U-7020 manufactured by Mitsui Chemicals, Inc.) having a number average molecular weight of 2000 was added, and the mixture was allowed to react at 90° C. for 5 hours. Then, it was cooled to 60° C., 105 parts by mass of propylene glycol monomethyletheracetate was added, and the mixture was stirred and mixed at the same temperature for 1 hour, thereby producing a polyurethane prepolymer.

A mixer equipped with a nitrogen inlet line was charged with 2-(2-propyl-1,3-oxazolidine-3-yl)-ethanol (manufactured by Wako Pure Chemical Industries, Ltd.) and norbornanediisocyanate (manufactured by Mitsui Chemicals, Inc., NBDI) at a molar ratio of 2:1, and reaction was performed at 100° C. for 6 hours, thereby preparing an oxazolidine compound.

105.58 parts by mass of the oxazolidine compound was added to the above-described polyurethane prepolymer, and the mixture was stirred at 50° C. for 1 hour, thereby producing a one component curable sealing-use polyurethane.

Thereafter, a planetary mixer was charged with 811.6 parts by mass of one component curable sealing-use polyurethane with its temperature adjusted to 50° C., 56.7 parts by mass fumed silica (AEROSIL #200), 79.6 parts by mass of gray colored DRY COLOR (manufactured by TOYO-COLOR CO., LTD.), 17.5 parts by mass of an antioxidant (IRGANOX 1076 manufactured by BASF), 7 parts by mass of a ultraviolet absorber (TINUVIN 213 manufactured by BASF), and 27.0 parts by mass of isoparaffin solvent (ISOPAR M manufactured by SHOWA SHELL SEKIYU K. K.), and the mixture was stirred under vacuum, thereby producing a one component curable sealing composition.

Then, the one component curable sealing composition was aged under conditions of a temperature of 23° C. and a relative humidity of 50% for 7 days, thereby producing a one-component curable sealant.

(Evaluation of One-Component Curable Sealant)

The color difference in UV irradiation test and tensile physical properties (tensile strength and elongation at break) of the produced one-component curable sealant were measured. The results are shown in Table 3. Correlation between the DCI content in the XDI composition (lower horizontal axis) and color difference in UV irradiation test (vertical axis), and correlation between the CBI content of the XDI composition (upper horizontal axis) and color difference in UV irradiation test (vertical axis) are shown in FIG. 9.

Figure 9:
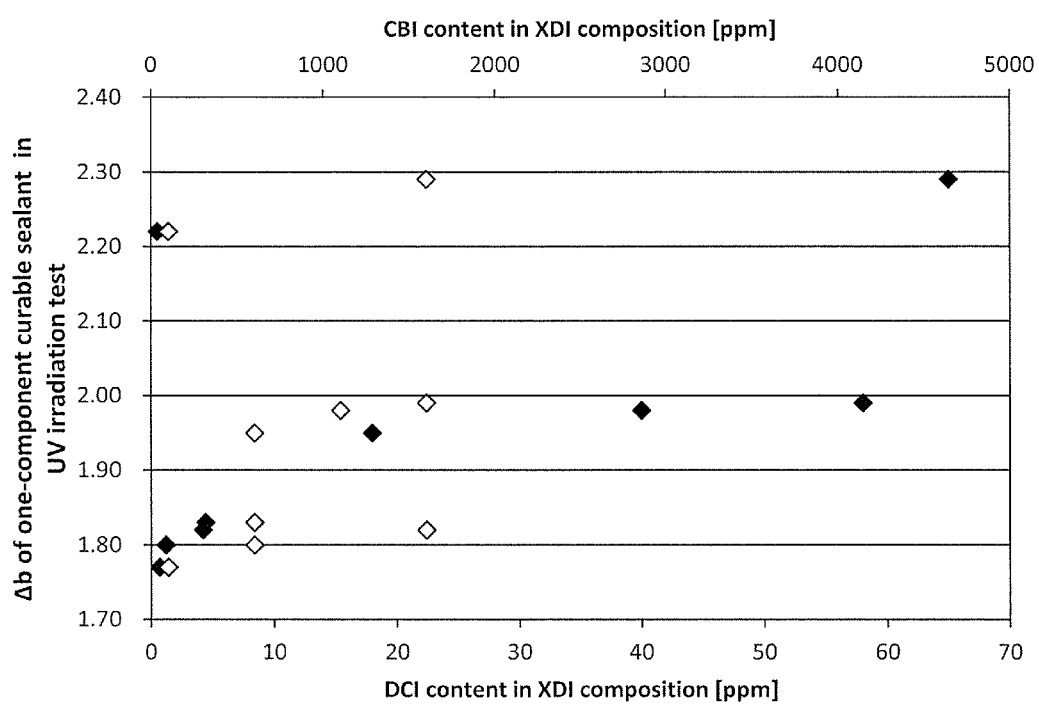
FIG. 9 is a graph illustrating correlation between the DCI content and the CBI content in the xylylenediisocyanate composition and the color difference in UV irradiation test of the one-component curable sealant.

As shown in Table 3 and FIG. 9, when the DCI content relative to a total mass of the XDI composition was 0.6 ppm or more and 60 ppm or less, irrespective of the CBI content, resistance to discoloration of the one-component curable sealant improved. This is clear from the comparison between Comparative Example 2 and Example 1, and Comparative Example 1 and Example 9.

Comparative Example 2 and Example 1 both had a CBI content of 100 ppm, but in Example 1 having a DCI content of 0.7 ppm, compared with Comparative Example 2 having a DCI content of 0.5 ppm, discoloration (increase in Δb) in UV irradiation test was significantly suppressed. Comparative Example 1 and Example 9 both had a CBI content of 1600 ppm, but in Example 9 having a DCI content of 58 ppm, compared with Comparative Example 1 having a DCI content of 65 ppm, discoloration (increase in Δb) in UV irradiation test was significantly suppressed.

When the DCI content relative to a total mass of the XDI composition was 60 ppm or less, mechanical properties (elongation and strength) of the one-component curable sealant improved. This is clear from the comparison between Comparative Example 1 and Example 9.

In Example 9 having a DCI content of 58 ppm, compared with Comparative Example 1 having a DCI content of 65 ppm, tensile strength and elongation at break of the one-component curable sealant significantly improved.

TABLE 3

| | no. | | | Comp. Ex. 2 | Ex. 1 | Ex. 2 | Ex. 3 | Ex. 4 | Ex. 5 | Ex. 6 | Ex. 7 | Ex. 8 | Ex. 9 | Comp. Ex. 1 |
|---|---|---|---|---|---|---|---|---|---|---|---|---|---|---|
| XDI composition | XDI | | [%] | 99.9 | 99.9 | 99.9 | 99.8 | 99.9 | 99.7 | 99.9 | 99.9 | 99.8 | 99.8 | 99.8 |
| | CBI | | [ppm] | 100 | 100 | 600 | 1600 | 600 | 3000 | 100 | 600 | 1100 | 1600 | 1600 |
| | DCI | | [ppm] | 0.5 | 0.7 | 1.2 | 4.2 | 4.4 | 4.5 | 4.5 | 18 | 40 | 58 | 65 |
| | Hydrolysable chlorine | | [ppm] | 60 | 70 | 160 | 380 | 210 | 640 | 100 | 210 | 360 | 380 | 380 |
| Coating material | | | | | | | | | | | | | | |
| Component A 1 | Coating discoloration and stain | Dis-color-ation 0 hr | b1 | 0.41 | 0.40 | — | 0.42 | 0.40 | — | — | 0.38 | 0.46 | 0.40 | 0.34 |
| | damp heat test | 1250 hr | Δb | 1.78 | 1.49 | — | 1.58 | 1.58 | — | — | 1.72 | 1.77 | 1.92 | 2.07 |
| | | 2000 hr | Δb | 2.41 | 1.87 | — | 1.89 | 1.87 | — | — | 1.93 | 2.08 | 2.32 | 2.50 |
| | Adherence | 2000 hr | Points | 4 | 6 | — | 10 | 10 | — | — | 10 | 10 | 6 | 4 |
| Component A 2 | Coating discoloration and stain | Dis-color-ation 0 hr | b1 | 0.54 | 0.58 | — | 0.57 | 0.55 | — | — | 0.51 | 0.59 | 0.56 | 0.52 |
| | damp heat test | 1250 hr | Δb | 1.41 | 1.26 | — | 1.38 | 1.34 | — | — | 1.44 | 1.52 | 1.58 | 1.61 |
| | | 2000 hr | Δb | 2.01 | 1.52 | — | 1.65 | 1.63 | — | — | 1.75 | 1.86 | 1.92 | 2.13 |
| | Adherence | 2000 hr | Points | 8 | 10 | — | 10 | 10 | — | — | 10 | 10 | 10 | 8 |
| Laminate adhesive | Main component/ curing agent | | Blending ratio | 10/6 | 10/6 | 10/6 | 10/6 | 10/6 | — | — | 10/6 | 10/6 | 10/6 | 10/6 |
| | Appearance | | [—] | BAD | GOOD | GOOD | GOOD | GOOD | — | — | GOOD | GOOD | GOOD | MEDIOCRE |

TABLE 3-continued

| | no. | | Comp. Ex. 2 | Ex. 1 | Ex. 2 | Ex. 3 | Ex. 4 | Ex. 5 | Ex. 6 | Ex. 7 | Ex. 8 | Ex. 9 | Comp. Ex. 1 |
|---|---|---|---|---|---|---|---|---|---|---|---|---|---|
| | Strength between AL/CPP After 40° C. 8 hr | [N] | 3.2 | 3.0 | 3.1 | 2.8 | 2.7 | — | — | 2.5 | 2.1 | 1.8 | 1.8 |
| | Strength between AL/CPP Before hot water sterilization test | [N] | 4.3 | 4.3 | 4.3 | 4.3 | 4.3 | — | — | 4.3 | 4.0 | 3.8 | 3.8 |
| | Strength between AL/CPP After hot water sterilization test | [N] | 4.2 | 4.2 | 4.2 | 4.2 | 4.2 | — | — | 4.2 | 3.9 | 3.7 | 3.6 |
| | Strength between AL/CPP After 50° C. 2 weeks storage | [N] | 4.1 | 4.1 | 4.1 | 4.1 | 4.1 | — | — | 4.1 | 3.8 | 3.7 | 3.7 |
| | UV irradiation test | $\Delta b$ | 1.41 | 1.10 | 1.12 | 1.18 | 1.21 | — | — | 1.26 | 1.29 | 1.32 | 1.46 |
| One- | UV irradiation test | b1 | 0.99 | 0.99 | 0.98 | 0.98 | 0.98 | — | — | 0.98 | 1.05 | 1.15 | 1.16 |
| component | (240 h) | b2 | 3.21 | 2.76 | 2.78 | 2.80 | 2.81 | — | — | 2.93 | 3.03 | 3.14 | 3.45 |
| curable | | $\Delta b$ | 2.22 | 1.77 | 1.80 | 1.82 | 1.83 | — | — | 1.95 | 1.98 | 1.99 | 2.29 |
| sealant | Tensile strength | [MPa] | 13.4 | 13.6 | 13.4 | 13.3 | 13.2 | — | — | 12.9 | 12.4 | 12.1 | 9.8 |
| | Elongation at break | [%] | 340 | 340 | 335 | 332 | 333 | — | — | 330 | 325 | 320 | 280 |

INDUSTRIAL APPLICABILITY

The xylylenediisocyanate composition, xylylenediisocyanate-modified composition, resin, and two-component resin material of the present invention are suitably used in various industrial products including, for example, elastomer, microcellular polyurethane, gel, polyurethane solution, foam, sealant, active energy ray curable resin, optical material, coating material, pressure-sensitive adhesive, binder, microcapsule, ink, transfer foil, and potting material.

DESCRIPTION OF REFERENCE NUMERALS

1 plant
2 salt-forming unit
3 isocyanate-formation unit
4 de-gassing unit
5 desolvation unit
6 tar-removal unit
7 low-boiling removal unit
8 rectification unit

The invention claimed is:

1. A polymerizable composition comprising:
an optical material-use xylylenediisocyanate composition comprising xylylenediisocyanate and a compound represented by Chemical Formula (1) below, wherein 0.6 ppm or more and 60 ppm or less of the compound represented by Chemical Formula (1) below is contained; and
an active hydrogen compound:

[Chemical Formula 1]

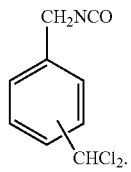

Chemical Formula (1)

2. A method for producing a polymerizable composition by mixing:
an optical material-use xylylenediisocyanate composition comprising xylylenediisocyanate and a compound represented by Chemical Formula (1) below, wherein 0.6 ppm or more and 60 ppm or less of the compound represented by Chemical Formula (1) below is contained; and
an active hydrogen compound:

[Chemical Formula 1]

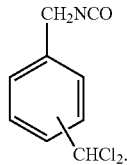

Chemical Formula (1)

3. A method for producing a plastic lens by copolymerizing the polymerizable composition according to claim 1 after introducing the polymerizable composition into a mold.

* * * * *